(12) United States Patent
Bush et al.

(10) Patent No.: US 11,299,523 B2
(45) Date of Patent: Apr. 12, 2022

(54) MODULATION OF RICE MPG1 ACTIVITY TO INCREASE BIOMASS ACCUMULATION, GRAIN YIELD, AND STRESS TOLERANCE IN PLANTS

(71) Applicant: Colorado State University Research Foundation, Fort Collins, CO (US)

(72) Inventors: Daniel R. Bush, Fort Collins, CO (US); Amanda K. Broz, Fort Collins, CO (US); Bettina E. Broeckling, Fort Collins, CO (US); Michael M. Friedman, Fort Collins, CO (US)

(73) Assignee: Colorado State University Research Foundation, Fort Collins, CO (US)

( * ) Notice: Subject to any disclaimer, the term of this patent is extended or adjusted under 35 U.S.C. 154(b) by 61 days.

(21) Appl. No.: 16/315,258

(22) PCT Filed: Jul. 6, 2017

(86) PCT No.: PCT/US2017/040815
§ 371 (c)(1),
(2) Date: Jan. 4, 2019

(87) PCT Pub. No.: WO2018/009600
PCT Pub. Date: Jan. 11, 2018

(65) Prior Publication Data
US 2019/0233480 A1 Aug. 1, 2019

Related U.S. Application Data

(60) Provisional application No. 62/359,016, filed on Jul. 6, 2016.

(51) Int. Cl.
*C07K 14/415* (2006.01)
*C12N 15/82* (2006.01)

(52) U.S. Cl.
CPC .......... *C07K 14/415* (2013.01); *C12N 15/827* (2013.01); *C12N 15/8223* (2013.01); *C12N 15/8271* (2013.01)

(58) Field of Classification Search
None
See application file for complete search history.

(56) References Cited

U.S. PATENT DOCUMENTS

2006/0123505 A1* 6/2006 Kikuchi ............... C07K 14/415
800/278
2013/0185826 A1 7/2013 Mirkov et al.

FOREIGN PATENT DOCUMENTS

WO WO2009127441 * 10/2009 ............. C12N 15/82

OTHER PUBLICATIONS

Lee et al. DREB2C Interacts with ABF2, a bZIP Protein Regulating Abscisic Acid-Responsive Gene Expression, and Its Overexpression Affects Abscisic Acid Sensitivity. Plant Physiology. 2010. 153: 716-727.*
Rahmaningsih, Miranti, "Phenotypic and Gene Expression Analysis of Diverse Rice Genotypes in Response to Drought" (2016). Theses and Dissertations. Table 2-2. pp. 1, 49.*
Gen Bank Accession AK108208. *Oryza sativa Japonica* Group cDNA clone:002-140-D07, full insert sequence. Published Dec. 4, 2008. pp. 1-2.*
Gen Bank Accession BAF24190. Os08g0521600 [*Oryza sativa Japonica* Group], Published Aug. 11, 2012. pp. 1-2.*
Leach et al. An Integrated Approach to Improving Plant Biomass Production. Final Report: DOE-CSU-5338170. Published Jan. 15, 2016. pp. 1-15. Obtained from https://www.osti.gov/servlets/purl/1234910.*
Gan et al. Transcriptional characteristics of Xa21-mediated defense responses in rice. Journal of Integrative Plant Biology. 2011. 53(4):300-311.*
Pegoraro et al. Ethylene response factors gene regulation and expression profiles under different stresses in rice. Theoretical and Experimental Plant Physiology. 2013. 25(4): 261-274.*
Colorado State University Research Foundation, PCT/US17/40815 filed Jul. 6, 2017, The International Search Report and the Written Opinion of the International Searching Authority, or the Declaration, 20 pages, dated Jan. 5, 2018.
25th Western Photosynthesis Conference Brochure with abstract articles, https://conferencereg.colostate.edu/WPM2016, 53 pages, Jan. 3, 2016.
Jisha et al., "Overexpression of an AP2/ERF Type Transcription Factor OsEREBP1 Confers Biotic and Abiotic Stress Tolerance in Rice", PLOS One, 24 pages, Jun. 2, 2015.
Rashid et al., "AP2/ERF Transcription Factor in Rice: Genome-Wide Canvas and Syntenic Relationships between Monocots and Eudicots", Evolutionary Bioinformatics, vol. 8, pp. 321-355, 2012.
"*Oryza sativa Japonica* Group ethylene-responsive transcription factor ERF015 (LOC4346073), mRNA", NCBI Reference Sequence: XM_015793965 1, 2 pages, Mar. 10, 2016.
"Ethylene-responsive transcription factor ERF015 [*Oryza sataive Japonica* Group]", NCBI Reference Sequence: XP_015649451.1, 1 page, Mar. 1, 2016.

* cited by examiner

*Primary Examiner* — Brent T Page
(74) *Attorney, Agent, or Firm* — McKee, Voorhees & Sease, PLC

(57) ABSTRACT

The invention provides methods for improving plant yield, biomass accumulation and stress tolerance. A novel AP2-like transcription factor MPG1, which when modulated impacts grain yield, biomass and abiotic and biotic stress tolerance when compared to non-modulated plants. The invention further provides methods using recombinant expression cassettes, host cells, transgenic plants and breeding methods using the same.

9 Claims, 41 Drawing Sheets

Specification includes a Sequence Listing.

A. HM *mpg1*                WT

B.

HM *mpg1*                WT ial Patent Application Ser. No. 62/359,016 filed Jul. 6, 2016, herein incorporated by reference in its entirety.

SEQUENCE LISTING

<160> NUMBER OF SEQ ID NOS: 3

<210> SEQ ID NO 1
<211> LENGTH: 570
<212> TYPE: DNA
<213> ORGANISM: Oryza sativa

<400> SEQUENCE: 1
atggtgccgc cggcggcgca cgcgccgaag aacctggggc tgaggggggt gcggcgccgg    60

```
ctgtggggca ggtgggcggc ggagatccgc gtgccgcggg gccaccgcgc ggccgcgagg    120
ctgtggatcg gcacgttccc gtccccggcg gcggcggcgc tcgcctacga cgccgcgctc    180
tactgcttcc acggcggcgc gccgccgggg aaccgcgcct tcaacttccc gcacgcgccg    240
cgcctccgca tcgacgaccg ccgccgccac gcgctcacgc cgggccacgt cagggccatc    300
gccgagaggt acgcccacga cgtcggctcc gtcctgttcc gcccgctccc tccgccgccg    360
ccgcccgtcg ccgccgccgc cgtccccgtg ttcgccgcac tgcaccgcc catggcgccg    420 gcgccggcca accatgctgc cgatccttac tactgcaacg agcctgacac caccacagac    480
gaggacgtca tggctgcggc tgaccgcctc ctctccatgg acatcgaaga ggtcgccgct    540
ttgatcgcca ttgttcagca aggagagtga                                     570
```

<210> SEQ ID NO 2
<211> LENGTH: 189
<212> TYPE: PRT
<213> ORGANISM: Oryza sativa

<400> SEQUENCE: 2

```
Met Val Pro Pro Ala Ala His Ala Pro Lys Asn Leu Gly Leu Arg Gly
1               5                   10                  15

Val Arg Arg Arg Leu Trp Gly Arg Trp Ala Ala Glu Ile Arg Val Pro
            20                  25                  30

Arg Gly His Arg Ala Ala Ala Arg Leu Trp Ile Gly Thr Phe Pro Ser
        35                  40                  45

Pro Ala Ala Ala Leu Ala Tyr Asp Ala Ala Leu Tyr Cys Phe His
    50                  55                  60

Gly Gly Ala Pro Pro Gly Asn Arg Ala Phe Asn Phe Pro His Ala Pro
65                  70                  75                  80

Arg Leu Arg Ile Asp Asp Arg Arg His Ala Leu Thr Pro Gly His
            85                  90                  95

Val Arg Ala Ile Ala Glu Arg Tyr Ala His Asp Val Gly Ser Val Leu
            100                 105                 110

Phe Arg Pro Leu Pro Pro Pro Pro Pro Val Ala Ala Ala Val
        115                 120                 125

Pro Val Phe Ala Ala Pro Ala Pro Met Ala Pro Ala Asn
    130                 135                 140

His Ala Ala Asp Pro Tyr Tyr Cys Asn Glu Pro Asp Thr Thr Thr Asp
145                 150                 155                 160

Glu Asp Val Met Ala Ala Asp Arg Leu Leu Ser Met Asp Ile Glu
                165                 170                 175

Glu Val Ala Ala Leu Ile Ala Ile Val Gln Gln Gly Glu
            180                 185
```

<210> SEQ ID NO 3
<211> LENGTH: 909
<212> TYPE: DNA
<213> ORGANISM: Oryza sativa

<400> SEQUENCE: 3

```
accatctcct cctcgtcatc gtcatcgtct tcctcctcgc gtcgccgatc acctcgccat     60
ggtgccgccg gcggcgcacg cgccgaagaa cctggggctg agggggggtgc ggcgccggct    120 gtggggcagg tggcggcgg agatccgcgt gccgcggggc caccgcgcgg ccgcgaggct    180
gtggatcggc acgttcccgt ccccggcggc ggcggcgctc gcctacgacg ccgcgctcta    240
```

-continued

```
ctgcttccac ggcggcgcgc cgccggggaa ccgcgccttc aacttccgc acgcgccgcg      300 cctccgcatc gacgaccgcc gccgccacgc gctcacgccg ggccacgtca gggccatcgc      360
cgagaggtac gcccacgacg tcggctccgt cctgttccgc ccgctccctc cgccgccgcc      420
gcccgtcgcc gccgccgccg tcccgtgtt cgccgcacct gcaccgccca tggcgccggc      480
gccggccaac catgctgccg atccttacta ctgcaacgag cctgacacca ccacagacga      540
ggacgtcatg gctgcggctg accgcctcct ctccatggac atcgaagagg tcgccgcttt      600
gatcgccatt gttcagcaag gagagtgacc atatctacaa cttcttagct agctagttac      660
accttctatg tagcatgtgt actatgcact tttgtggttg tgttgtgctg tcctaatggt      720
gtaactagcc atatcaagga agacatgcat gatctagagt ctagagtact ctagccatgg      780
aataaattaa cttagtctgt acttggtcat gcaccttgtg tatgatcctt gtgtaagaga      840
agtgtaataa tcggttcttg aaaaggaact gttgttatat atgagatgga tgttgtcatg      900
aaatggaaa                                                              909
```

MODULATION OF RICE MPG1 ACTIVITY TO INCREASE BIOMASS ACCUMULATION, GRAIN YIELD, AND STRESS TOLERANCE IN PLANTS

CROSS-REFERENCE TO RELATED APPLICATIONS

This application claims priority under 35 U.S.C § 119 to Provisional Patent Application Ser. No. 62/359,016 filed Jul. 6, 2016, herein incorporated by reference in its entirety.

GRANT REFERENCE

This invention was made with government support under grant 2008-35504-04852 awarded by USDA National Institute of Food and Agriculture and grant DE-FG02-08ER64629 awarded by Department of Energy. The government has certain rights in the invention.

FIELD OF THE INVENTION

The invention relates generally to the field of molecular biology and plant genetics.

BACKGROUND OF THE INVENTION

The domestication of many plants has correlated with dramatic increases in yield. Yield is one of the most complex agronomic traits and is determined by the interaction of specific genetics within the crops with environmental factors. Seed yield is a particularly important trait, since the seeds of many plants are important for human and animal nutrition. Crops such as corn, rice, wheat, canola and soybean account for over half the total human caloric intake, whether through direct consumption of the seeds themselves or through consumption of meat products raised on processed seeds. They are also a source of sugars, oils and many kinds of metabolites used in industrial processes. Seeds contain an embryo (the source of new shoots and roots) and an endosperm (the source of nutrients for embryo growth during germination and during early growth of seedlings). The development of a seed involves many genes, and requires the transfer of metabolites from the roots, leaves and stems into the growing seed. The endosperm, in particular, assimilates the metabolic precursors of carbohydrates, oils and proteins and synthesizes them into storage macromolecules to fill out the grain.

There are three general approaches to increasing yield potential: 1) increasing overall plant productivity to increase harvestable yield, 2) increasing the allocation of resources (carbohydrates and amino acids) to harvested tissues (seed, storage organs, etc.) and 3) overcoming the negative consequences of any stresses on growth (whether abiotic or biotic). Abiotic stress is the primary cause of crop loss worldwide, causing average yield losses more than 50% for major crops (Boyer, (1982) Science 218:443-448; Bray, et al., (2000) In Biochemistry and Molecular Biology of Plants, edited by Buchannan, et al., Amer. Soc. Plant Biol., pp. 1158-1249). For example, exposure of plants to a water-limiting environment during various developmental stages appears to activate various physiological and developmental changes that decrease yield. Tolerance to these sorts of stresses remains a primary goal of increasing yield and production.

Traditional methods of improving yield have centered around breeding techniques. Breeders have long used conventional breeding techniques to improve yield. While significant improvements have been achieved, breeding techniques are laborious and slow because of the time required to breed and grow successive plant generations. Furthermore, for many crops, yield increases have significantly slowed as much of the genetic potential for increases have already been exploited. Thus, grain yield improvements by conventional breeding have nearly reached a plateau in crop plants.

Technologic developments have helped address the need to increase plant productivity in order to feed the expanding world population. The identification of novel genes (or gene) that can have a dramatic impact on yield in domesticated plants, has become an important focus of agricultural research. Biotechnology is playing an increasingly important role in this effort by providing, for example, plants having increased resistance to drought and insect infestation. Thus there is a continuing need to understand and manipulate biochemical and molecular mechanisms contributing to yield, biomass production, and stress tolerance.

SUMMARY OF THE INVENTION

The present invention presents methods to alter the genetic composition of crop plants, especially monocots such as maize or rice, so that such crops can have improved biomass accumulation, grain yield, and stress tolerance (to both abiotic and biotic stresses). The invention in one embodiment relates to modulation (increased expression) of novel identified MPG1 sequences and/or activity in plants. Applicants have identified a gene, termed MPG1, which is likely a member of the AP2/ERF transcription factor superfamily of genes. When MPG1 is overexpressed, it has a beneficial increase in plant biomass (leaf length, leaf width, height, tiller number, girth), increase in seed yield (panicle number, spikelet number, grain filling), improved tolerance to abiotic/biotic stress, increased generation of awns, and delayed flowering time. Plants with MPG1 are resistant to abiotic stress and maintain yield under suboptimal growth conditions. This is perhaps the most agriculturally significant impact of MPG1 over expression on yield, stress tolerance and biomass accumulation.

Applicants have surprisingly found that modulation of MPG1 improves plant biomass accumulation, stress tolerance and grain yield and these changes have no deleterious effect on plant performance. The invention provides methods for improving plant performance by modulating the activity of at least one MPG1 gene (and plants produced by such methods).

According to the invention a method of modulating the MPG1 pathway comprises modulating the activity of one or more MPG1 genes in the plant, wherein the one or more MPG1 genes encode one or more MPG1 (AP2/ERF-like genes), wherein at least one of the one or more MPG1 genes comprises, e.g., at least about 70%, at least about 75%, at least about 80%, at least about 85%, at least about 90%, at least about 95%, at least about 99%, at least about 99.5% or more sequence identity to SEQ ID NO:1 or 3 (OS08G41030). Many AP2 transcription factor genes are known to those of skill in the art and are readily available through sources such as GENBANK and the like.

In another embodiment, the modulating comprises: (a) introducing into the plant at least one polynucleotide sequence, wherein the at least one polynucleotide sequence comprises a nucleic acid encoding one or more MPG1 genes, or a subsequence thereof, and a heterologous promoter, which promoter functions in plants and/or, (b)

expressing at least one polynucleotide sequence, thereby modulating (increasing) the activity of one or more MPG1 native genes compared to a corresponding control plant (e.g., its non-transgenic parent or a non-transgenic plant of the same species). For example, the at least one polynucleotide sequence can be introduced by techniques including, but not limited to, electroporation, micro-projectile bombardment, *Agrobacterium*-mediated transfer, and the like. In certain other embodiments, gene editing protocols may be used to modulate (increase) activity of MPG1 genes as disclosed herein. Essentially all of the features noted above apply to this embodiment as well, as relevant.

In another embodiment, the invention thus relates to methods for improving plant biomass accumulation, grain yield, and/or stress tolerance by providing an isolated or recombinant modified plant cell comprising at least one modification that modulates MPG1 activity. An MPG1 gene, includes a nucleic acid sequence, or complement thereof, comprising, e.g., at least about 70%, at least about 75%, at least about 80%, at least about 85%, at least about 90%, at least about 95%, at least about 99%, about 99.5% or more to sequence identity to SEQ ID NO:1 or 3 (OS08G41030). The modulation changes expression or activity of at least one MPG1 protein compared to a corresponding control or non-modified plant cell lacking the modulating nucleic acid sequence.

In one embodiment, the methods involving one modification in the plant cell include introducing at least one polynucleotide sequence comprising an MPG1 nucleic acid sequence, or subsequence thereof, into a plant cell, such that at least one polynucleotide sequence is linked to a promoter, and where at least one polynucleotide sequence comprises, e.g., at least about 70%, at least about 75%, at least about 80%, at least about 85%, at least about 90%, at least about 95%, at least about 99%, about 99.5% or more sequence identity to SEQ ID NO:1 of 3 (OS08G41030), or a subsequence thereof, or a complement thereof. A plant cell produced from the plant described herein is disclosed. A seed produced from the plant described herein is disclosed.

In certain embodiments, a plant cell resulting from the methods of the invention is from a dicot or monocot. In another aspect, the plant cell is in a plant comprising a sterility phenotype, e.g., a male sterility phenotype. Breeding methods using the plant of the invention also contemplated herein to develop lines, varieties or populations with the improved traits of the invention.

The methods of the invention are practiced with an isolated or recombinant polynucleotide comprising a member selected from the group consisting of: (a) a polynucleotide, or a complement thereof, comprising, e.g., at least about 70%, at least about 75%, at least about 80%, at least about 85%, at least about 90%, at least about 95%, at least about 99%, about 99.5% or more sequence identity to SEQ ID NO:1 or 3 (OS08G41030), or a subsequence thereof, or a conservative variation thereof; (b) a polynucleotide, or a complement thereof, encoding a polypeptide sequence of SEQ ID NO:2 (OS08G41030), or a subsequence thereof, or a conservative variation thereof; (c) a polynucleotide, or a complement thereof, that hybridizes under stringent conditions over substantially the entire length of a polynucleotide subsequence comprising at least 100 contiguous nucleotides of SEQ ID NO: for 3 (OS08G41030), or that hybridizes to a polynucleotide sequence of (a) or (b); and, (d) a polynucleotide that is at least about 85% identical to a polynucleotide sequence of (a), (b) or (c). In at least some embodiments the polynucleotide includes at least one base change so as not to be the genomic sequence. In certain embodiments the polynucleotide or polypeptide includes one or more base changes to that the sequence is not the naturally occurring sequence.

Such polynucleotides for practice of the methods of the invention can comprise or be contained within an expression cassette or a vector (e.g., a viral vector). The vector or expression cassette can comprise a promoter (e.g., a constitutive, tissue-specific, or inducible promoter) operably linked to the polynucleotide. A polynucleotide of the invention can be linked to the promoter in an antisense orientation or a sense orientation, be configured for expression, RNA silencing or interference, or the like.

Detection of expression products is performed either qualitatively (by detecting presence or absence of one or more product of interest) or quantitatively (by monitoring the level of expression of one or more product of interest). In one embodiment, the expression product is an RNA expression product. Aspects of the invention optionally include monitoring an expression level of a nucleic acid, polypeptide or chemical (e.g., AP2/ERF transcription factor) as noted herein for detection of MPG1 production, APS2/ERF production, biomass accumulation, grain yield, and stress tolerance conditions, etc. in a plant or in a population of plants.

In yet another embodiment, the present invention is directed to a transgenic plant or plant cells with improved performance, containing the nucleic acids described herein. Preferred plants containing the polynucleotides of the present invention include but are not limited to maize, soybean, sunflower, sorghum, canola, wheat, alfalfa, cotton, oat, rice, barley, tomato, cacao and millet. In another embodiment, the transgenic plant is a rice plant or plant cells. Plants produced according to the invention can have at least one of the following phenotypes in as compared to a non-modified control plant, including but not limited to: increased grain yield, increased abiotic stress tolerance, increased biotic stress tolerance, or increased biomass accumulation when compared to a non-modified plant.

DETAILED DESCRIPTION OF THE INVENTION

Figure 1:
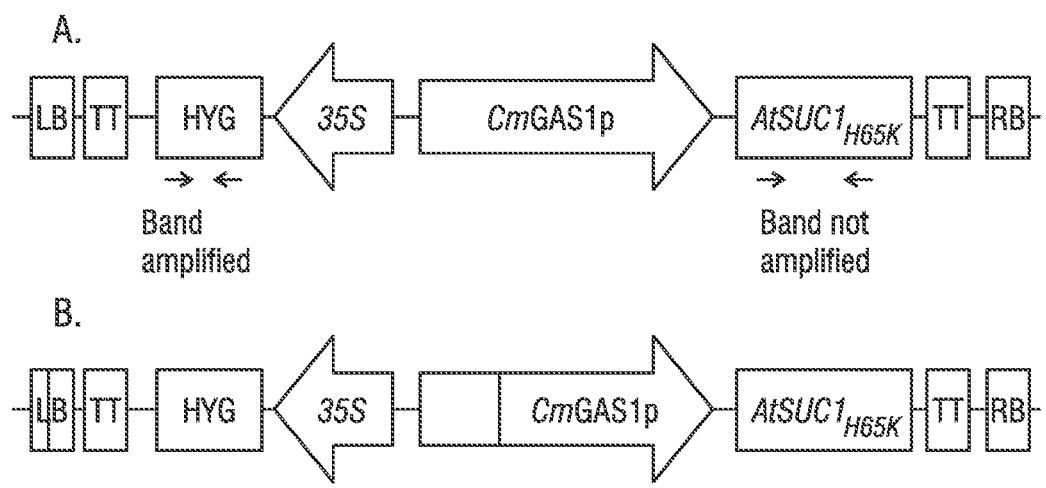
FIGS. 1A and 1B are depictions of the full T-DNA expression cassette inserted into plants. 1B represents the portion of the T-DNA expression cassette that successfully inserted into the gDNA of mpg1 mutant. The portion that successfully integrated can be characterized by the white backgrounds.

The practice of the present invention will employ, unless otherwise indicated, conventional techniques of botany, microbiology, tissue culture, molecular biology, chemistry, biochemistry and recombinant DNA technology, which are within the skill of the art. Such techniques are explained fully in the literature. See, e.g., Langenheim and Thimann, (1982) *Botany: Plant Biology and Its Relation to Human Affairs*, John Wiley; Cell Culture and Somatic Cell Genetics of Plants, vol. 1, Vasil, ed. (1984); Stanier, et al., (1986) *The Microbial World*, 5th ed., Prentice-Hall; Dhringra and Sinclair, (1985) *Basic Plant Pathology Methods*, CRC Press; Maniatis, et al., (1982) *Molecular Cloning: A Laboratory Manual; DNA Cloning*, vols. I and II, Glover, ed. (1985); *Oligonucleotide Synthesis*, Gait, ed. (1984); *Nucleic Acid Hybridization*, Hames and Higgins, eds. (1984); and the series *Methods in Enzymology*, Colowick and Kaplan, eds., Academic Press, Inc., San Diego, Calif.

Units, prefixes, and symbols may be denoted in their SI accepted form. Unless otherwise indicated, nucleic acids are written left to right in 5' to 3' orientation; amino acid sequences are written left to right in amino to carboxy orientation, respectively. Numeric ranges are inclusive of the numbers defining the range. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes. The terms defined below are more fully defined by reference to the specification as a whole.

In describing the present invention, the following terms will be employed, and are intended to be defined as indicated below.

By "amplified" is meant the construction of multiple copies of a nucleic acid sequence or multiple copies complementary to the nucleic acid sequence using at least one of the nucleic acid sequences as a template. Amplification systems include the polymerase chain reaction (PCR) system, ligase chain reaction (LCR) system, nucleic acid sequence based amplification (NASBA, Cangene, Mississauga, Ontario), Q-Beta Replicase systems, transcription-based amplification system (TAS), and strand displacement amplification (SDA). See, e.g., *Diagnostic Molecular Microbiology: Principles and Applications*, Persing, et al., eds., American Society for Microbiology, Washington, D.C. (1993). The product of amplification is termed an amplicon.

The term "conservatively modified variants" applies to both amino acid and nucleic acid sequences. With respect to particular nucleic acid sequences, conservatively modified variants refer to those nucleic acids that encode identical or conservatively modified variants of the amino acid sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations" and represent one species of conservatively modified variation. Every nucleic acid sequence herein that encodes a polypeptide also describes every possible silent variation of the nucleic acid. One of ordinary skill will recognize that each codon in a nucleic acid (except AUG, which is ordinarily the only codon for methionine; one exception is *Micrococcus rubens*, for which GTG is the methionine codon (Ishizuka, et al., (1993) *J. Gen. Microbiol.* 139:425-32) can be modified to yield a functionally identical molecule. Accordingly, each silent variation of a nucleic acid, which encodes a polypeptide of the present invention, is implicit in each described polypeptide sequence and incorporated herein by reference.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" when the alteration results in the substitution of an amino acid with a chemically similar amino acid. Thus, any number of amino acid residues selected from the group of integers consisting of from 1 to 15 can be so altered. Thus, for example, 1, 2, 3, 4, 5, 7 or 10 alterations can be made. Conservatively modified variants typically provide similar biological activity as the unmodified polypeptide sequence from which they are derived. For example, substrate specificity, enzyme activity, or ligand/receptor binding is generally at least 30%, 40%, 50%, 60%, 70%, 80% or 90%, preferably 60-90% of the native protein for its native substrate. Conservative substitution tables providing functionally similar amino acids are well known in the art.

The following six groups each contain amino acids that are conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

See also, Creighton, *Proteins*, W.H. Freeman and Co. (1984).

As used herein, "consisting essentially of" means the inclusion of additional sequences to an object polynucleotide where the additional sequences do not selectively hybridize, under stringent hybridization conditions, to the same cDNA as the polynucleotide and where the hybridization conditions include a wash step in 0.1×SSC and 0.1% sodium dodecyl sulfate at 65° C.

By "encoding" or "encoded," with respect to a specified nucleic acid, is meant comprising the information for translation into the specified protein. A nucleic acid encoding a protein may comprise non-translated sequences (e.g., introns) within translated regions of the nucleic acid, or may lack such intervening non-translated sequences (e.g., as in cDNA). The information by which a protein is encoded is specified by the use of codons. Typically, the amino acid sequence is encoded by the nucleic acid using the "universal" genetic code. However, variants of the universal code, such as is present in some plant, animal, and fungal mitochondria, the bacterium *Mycoplasma capricolum* (Yamao, et al., (1985) *Proc. Natl. Acad. Sci. USA* 82:2306-9), or the ciliate *Macronucleus*, may be used when the nucleic acid is expressed using these organisms.

When the nucleic acid is prepared or altered synthetically, advantage can be taken of known codon preferences of the intended host where the nucleic acid is to be expressed. For example, although nucleic acid sequences of the present invention may be expressed in both monocotyledonous and dicotyledonous plant species, sequences can be modified to account for the specific codon preferences and GC content preferences of monocotyledonous plants or dicotyledonous plants as these preferences have been shown to differ (Murray, et al., (1989) *Nucleic Acids Res.* 17:477-98 and herein incorporated by reference). Thus, the rice preferred codon for a particular amino acid might be derived from known gene sequences from rice.

As used herein, "heterologous" in reference to a nucleic acid is a nucleic acid that originates from a foreign species, or, if from the same species, is substantially modified from its native form in composition and/or genomic locus by deliberate human intervention. For example, a promoter operably linked to a heterologous structural gene is from a species different from that from which the structural gene was derived or, if from the same species, one or both are substantially modified from their original form. A heterologous protein may originate from a foreign species or, if from the same species, is substantially modified from its original form by deliberate human intervention.

By "host cell" is meant a cell, which comprises a heterologous nucleic acid sequence of the invention, which contains a vector and supports the replication and/or expression of the expression vector. Host cells may be prokaryotic cells such as *E. coli*, or eukaryotic cells such as yeast, insect, plant, amphibian, or mammalian cells. Preferably, host cells are monocotyledonous or dicotyledonous plant cells, including but not limited to maize, sorghum, sunflower, soybean, wheat, alfalfa, rice, cotton, canola, lawn grass, barley, millet, and tomato. A particularly preferred monocotyledonous host cell is a rice host cell.

The term "hybridization complex" includes reference to a duplex nucleic acid structure formed by two single-stranded nucleic acid sequences selectively hybridized with each other.

The term "introduced" in the context of inserting a nucleic acid into a cell, means "transfection" or "transformation" or "transduction" and includes reference to the incorporation of a nucleic acid into a eukaryotic or prokaryotic cell where the nucleic acid may be incorporated into the genome of the cell (e.g., chromosome, plasmid, plastid or mitochondrial DNA), converted into an autonomous replicon, or transiently expressed (e.g., transfected mRNA).

The terms "isolated" or "isolated nucleic acid" or "isolated protein" refer to material, such as a nucleic acid or a protein, which is substantially or essentially free from components which normally accompany or interact with it as found in its naturally occurring environment. The isolated material optionally comprises material not found with the material in its natural environment. Nucleic acids which are "isolated", as defined herein, are also referred to as "heterologous" nucleic acids. Unless otherwise stated, the term "MPG1 nucleic acid" means a nucleic acid comprising a polynucleotide ("MPG1 polynucleotide") encoding a full length or partial length MPG1 polypeptide with MPG1 activity as defined herein.

As used herein, "nucleic acid" includes reference to a deoxyribonucleotide or ribonucleotide polymer in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids).

By "nucleic acid library" is meant a collection of isolated DNA or RNA molecules, which comprise and substantially represent the entire transcribed fraction of a genome of a specified organism. Construction of exemplary nucleic acid libraries, such as genomic and cDNA libraries, is taught in standard molecular biology references such as Berger and Kimmel, (1987) *Guide To Molecular Cloning Techniques*, from the series *Methods in Enzymology*, vol. 152, Academic Press, Inc., San Diego, Calif.; Sambrook, et al., (1989) *Molecular Cloning: A Laboratory Manual*, 2nd ed., vols. 1-3; and *Current Protocols in Molecular Biology*, Ausubel, et al., eds, *Current Protocols*, a joint venture between Greene Publishing Associates, Inc. and John Wiley & Sons, Inc. (1994 Supplement).

As used herein "operably linked" includes reference to a functional linkage between a first sequence, such as a promoter, and a second sequence, wherein the promoter sequence initiates and mediates transcription of the DNA corresponding to the second sequence. Generally, operably linked means that the nucleic acid sequences being linked are contiguous and, where necessary to join two protein coding regions, contiguous and in the same reading frame.

As used herein, the term "plant" includes reference to whole plants, plant organs (e.g., leaves, stems, roots, etc.), seeds and plant cells and progeny of same. Plant cell, as used herein includes, without limitation, cells in or from seeds, suspension cultures, embryos, meristematic regions, callus tissue, leaves, roots, shoots, gametophytes, sporophytes, pollen, and microspores. The class of plants which can be used in the methods of the invention is generally as broad as the class of higher plants amenable to transformation techniques, including both monocotyledonous and dicotyledonous plants including species from the genera: *Cucurbita, Rosa, Vitis, Juglans, Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Ciahorium, Helianthus, Lactuca, Bromus, Asparagus, Antirrhinum, Heterocallis, Nemesis, Pelargonium, Panieum, Pennisetum, Ranunculus, Senecio, Salpiglossis, Cucumis, Browaalia, Glycine, Pisum, Phaseolus, Lolium, Oryza, Avena, Hordeum, Secale, Allium*, and *Triticum*. A particularly preferred plant is *Zea mays*.

As used herein, "yield" may include reference to bushels per acre of a grain crop at harvest, as adjusted for grain moisture (15% typically for maize, for example), and/or the volume of biomass generated (for forage crops such as alfalfa, and plant root size for multiple crops). Grain moisture is measured in the grain at harvest. The adjusted test weight of grain is determined to be the weight in pounds per bushel, adjusted for grain moisture level at harvest. Biomass is measured as the weight of harvestable plant material generated.

As used herein, "polynucleotide" includes reference to a deoxyribopolynucleotide, ribopolynucleotide, or analogs thereof that have the essential nature of a natural ribonucleotide in that they hybridize, under stringent hybridization conditions, to substantially the same nucleotide sequence as naturally occurring nucleotides and/or allow translation into the same amino acid(s) as the naturally occurring nucleotide(s). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including inter alia, simple and complex cells.

The terms "polypeptide," "peptide," and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers.

As used herein "promoter" includes reference to a region of DNA upstream from the start of transcription and involved in recognition and binding of RNA polymerase and other proteins to initiate transcription. A "plant promoter" is a promoter capable of initiating transcription in plant cells. Exemplary plant promoters include, but are not limited to, those that are obtained from plants, plant viruses, and bacteria which comprise genes expressed in plant cells such *Agrobacterium* or *Rhizobium*. Examples are promoters that preferentially initiate transcription in certain tissues, such as leaves, roots, seeds, fibres, xylem vessels, tracheids, or sclerenchyma. Such promoters are referred to as "tissue-preferred." A "cell type" specific promoter primarily drives expression in certain cell types in one or more organs, for example, vascular cells in roots or leaves. An "inducible" or "regulatable" promoter is a promoter which is under environmental control. Examples of environmental conditions that may affect transcription by inducible promoters include anaerobic conditions or the presence of light. Another type of promoter is a developmentally regulated promoter, for example, a promoter that drives expression during pollen development. Tissue preferred, cell type specific, developmentally regulated, and inducible promoters constitute the class of "non-constitutive" promoters. A "constitutive" promoter is a promoter, which is active under most environmental conditions.

The term "MPG1 polypeptide" refers to one or more amino acid sequences. The term is also inclusive of fragments, variants, homologs, alleles or precursors (e.g., preproproteins or proproteins) thereof that retain the function of catalyzing the conversion of S-adenosylmethionine to ACC. An "MPG1 protein" comprises an MPG1 polypeptide. Unless otherwise stated, the term "MPG1 nucleic acid" means a nucleic acid comprising a polynucleotide ("MPG1 polynucleotide") encoding an MPG1 polypeptide.

As used herein "recombinant" includes reference to a cell or vector that has been modified by the introduction of a heterologous nucleic acid, or that the cell is derived from a cell so modified. Thus, for example, recombinant cells express genes that are not found in identical form within the native (non-recombinant) form of the cell or express native genes that are otherwise abnormally expressed, under expressed or not expressed at all as a result of deliberate human intervention; or may have reduced or eliminated expression of a native gene. The term "recombinant" as used herein does not encompass the alteration of the cell or vector by naturally occurring events (e.g., spontaneous mutation, natural transformation/transduction/transposition) such as those occurring without deliberate human intervention.

As used herein, a "recombinant expression cassette" is a nucleic acid construct, generated recombinantly or synthetically, with a series of specified nucleic acid elements, which permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid to be transcribed, and a promoter.

The terms "residue" or "amino acid residue" or "amino acid" are used interchangeably herein to refer to an amino acid that is incorporated into a protein, polypeptide, or peptide (collectively "protein"). The amino acid may be a naturally occurring amino acid and, unless otherwise limited, may encompass known analogs of natural amino acids that can function in a similar manner as naturally occurring amino acids.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 40% sequence identity, preferably 60-90% sequence identity, and most preferably 100% sequence identity (i.e., complementary) with each other.

The terms "stringent conditions" or "stringent hybridization conditions" include reference to conditions under which a probe will hybridize to its target sequence, to a detectably greater degree than other sequences (e.g., at least 2-fold over background).

Stringent conditions are sequence-dependent and will be different in different circumstances. By controlling the stringency of the hybridization and/or washing conditions, target sequences can be identified which can be up to 100% complementary to the probe (homologous probing). Alternatively, stringency conditions can be adjusted to allow some mismatching in sequences so that lower degrees of similarity are detected (heterologous probing). Optimally, the probe is approximately 500 nucleotides in length, but can vary greatly in length from less than 500 nucleotides to equal to the entire length of the target sequence.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide or Denhardt's. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Specificity is typically the function of post-hybridization washes, the critical factors being the ionic strength and temperature of the final wash solution. For DNA-DNA hybrids, the Tm can be approximated from the equation of Meinkoth and Wahl, (1984) *Anal. Biochem.*, 138:267-84: Tm=81.5° C.+16.6 (log M)+0.41 (% GC)—0.61 (% form)—500/L; where M is the molarity of monovalent cations, % GC is the percentage of guanosine and cytosine nucleotides in the DNA, % form is the percentage of formamide in the hybridization solution, and L is the length of the hybrid in base pairs. The Tm is the temperature (under defined ionic strength and pH) at which 50% of a complementary target sequence hybridizes to a perfectly matched probe. Tm is reduced by about 1° C. for each 1% of mismatching; thus, Tm, hybridization and/or wash conditions can be adjusted to hybridize to sequences of the desired identity. For example, if sequences with >90% identity are sought, the Tm can be decreased 10° C. Generally, stringent conditions are selected to be about 5° C. lower than the thermal melting point (Tm) for the specific sequence and its complement at a defined ionic strength and pH. However, severely stringent conditions can utilize a hybridization and/or wash at 1, 2, 3 or 4° C. lower than the thermal melting point (Tm); moderately stringent conditions can utilize a hybridization and/or wash at 6, 7, 8, 9 or 10° C. lower than the thermal melting point (Tm); low stringency conditions can utilize a hybridization and/or wash at 11, 12, 13, 14, 15 or 20° C. lower than the thermal melting point (Tm). Using the equation, hybridization and wash compositions, and desired Tm, those of ordinary skill will understand that variations in the stringency of hybridization and/or wash solutions are inherently described. If the desired degree of mismatching results in a Tm of less than 45° C. (aqueous solution) or 32° C. (formamide solution) it is preferred to increase the SSC concentration so that a higher temperature can be used. An extensive guide to the hybridization of nucleic acids is found in Tijssen, *Laboratory Techniques in Biochemistry and Molecular Biology—Hybridization with Nucleic Acid Probes*, part I, chapter 2, "Overview of principles of hybridization and the strategy of nucleic acid probe assays," Elsevier, New York (1993); and *Current Protocols in Molecular Biology*, chapter 2, Ausubel, et al., eds, Greene Publishing and Wiley-Interscience, New York (1995). Unless otherwise stated, in the present application high stringency is defined as hybridization in 4×SSC, 5×Denhardt's (5 g Ficoll, 5 g polyvinypyrrolidone, 5 g bovine serum albumin in 500 ml of water), 0.1 mg/ml boiled salmon sperm DNA, and 25 mM Na phosphate at 65° C., and a wash in 0.1×SSC, 0.1% SDS at 65° C.

As used herein, "transgenic plant" includes reference to a plant, which comprises within its genome a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to include any cell, cell line, callus, tissue, plant part or plant, the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

As used herein, "vector" includes reference to a nucleic acid used in transfection of a host cell and into which can be inserted a polynucleotide. Vectors are often replicons. Expression vectors permit transcription of a nucleic acid inserted therein.

The following terms are used to describe the sequence relationships between two or more nucleic acids or polynucleotides or polypeptides: (a) "reference sequence," (b) "comparison window," (c) "sequence identity," (d) "percentage of sequence identity," and (e) "substantial identity."

As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

As used herein, "comparison window" means includes reference to a contiguous and specified segment of a polynucleotide sequence, wherein the polynucleotide sequence may be compared to a reference sequence and wherein the portion of the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, and 50, 100 or longer. Those of skill in the art understand that to avoid a high similarity to a reference sequence due to inclusion of gaps in the polynucleotide sequence a gap penalty is typically introduced and is subtracted from the number of matches.

Methods of alignment of nucleotide and amino acid sequences for comparison are well known in the art. The local homology algorithm (BESTFIT) of Smith and Waterman, (1981) *Adv. Appl. Math* 2:482, may conduct optimal alignment of sequences for comparison; by the homology alignment algorithm (GAP) of Needleman and Wunsch, (1970) *J Mol. Biol.* 48:443-53; by the search for similarity method (Tfasta and Fasta) of Pearson and Lipman, (1988) *Proc. Natl. Acad. Sci. USA* 85:2444; by computerized implementations of these algorithms, including, but not limited to: CLUSTAL in the PC/Gene program by Intelligenetics, Mountain View, Calif., GAP, BESTFIT, BLAST, FASTA, and TFASTA in the Wisconsin Genetics Software Package, Version 8 (available from Genetics Computer Group (GCG® programs (Accelrys, Inc., San Diego, Calif.).). The CLUSTAL program is well described by Higgins and Sharp, (1988) *Gene* 73:237-44; Higgins and Sharp, (1989) *CABIOS* 5:151-3; Corpet, et al., (1988) *Nucleic Acids Res.* 16:10881-90; Huang, et al., (1992) *Computer Applications in the Biosciences* 8:155-65, and Pearson, et al., (1994) *Meth. Mol. Biol.* 24:307-31. The preferred program to use for optimal global alignment of multiple sequences is PileUp (Feng and Doolittle, (1987) *J. Mol. Evol.,* 25:351-60 which is similar to the method described by Higgins and Sharp, (1989) *CABIOS* 5:151-53 and hereby incorporated by reference). The BLAST family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, *Current Protocols in Molecular Biology*, Chapter 19, Ausubel et al., eds., Greene Publishing and Wiley-Interscience, New York (1995).

GAP uses the algorithm of Needleman and Wunsch, supra, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package are 8 and 2, respectively. The gap creation and gap extension penalties can be expressed as an integer selected from the group of integers consisting of from 0 to 100. Thus, for example, the gap creation and gap extension penalties can be 0, 1, 2, 3, 4, 5, 6, 7, 8, 9, 10, 15, 20, 30, and 40, 50 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value to for a pair of symbols is greater than or equal to 0.50, the similarity threshold. The scoring matrix used in Version 10 of the Wisconsin Genetics Software Package is BLOSUM62 (see, Henikoff and Henikoff, (1989) *Proc. Natl. Acad. Sci. USA* 89:10915).

Unless otherwise stated, sequence identity/similarity values provided herein refer to the value obtained using the BLAST 2.0 suite of programs using default parameters (Altschul, et al., (1997) *Nucleic Acids Res.* 25:3389-402).

As those of ordinary skill in the art will understand, BLAST searches assume that proteins can be modeled as random sequences. However, many real proteins comprise regions of nonrandom sequences, which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, (1993) *Comput. Chem.* 17:149-63) and XNU (Claverie and States, (1993) *Comput. Chem.* 17:191-201) low-complexity filters can be employed alone or in combination.

As used herein, "sequence identity" or "identity" in the context of two nucleic acid or polypeptide sequences includes reference to the residues in the two sequences, which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Sequences, which differ by such conservative substitutions, are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, (1988) *Computer Applic. Biol. Sci.* 4:11-17, e.g., as implemented in the program PC/GENE (Intelligenetics, Mountain View, Calif., USA).

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" of polynucleotide sequences means that a polynucleotide comprises a sequence that has between 50-100% sequence identity, preferably at least 50% sequence identity, preferably at least 60% sequence identity, preferably at least 70%, more preferably at least 80%, more preferably at least 90%, and most preferably at least 95%, compared to a reference sequence using one of the alignment programs described using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of between 55-100%, preferably at least 55%, preferably at least 60%, more preferably at least 70%, 80%, 90%, and most preferably at least 95%.

Another indication that nucleotide sequences are substantially identical is if two molecules hybridize to each other under stringent conditions. The degeneracy of the genetic code allows for many amino acids substitutions that lead to variety in the nucleotide sequence that code for the same amino acid, hence it is possible that the DNA sequence could code for the same polypeptide but not hybridize to each other under stringent conditions. This may occur, e.g., when a copy of a nucleic acid is created using the maximum codon degeneracy permitted by the genetic code. One indication that two nucleic acid sequences are substantially identical is that the polypeptide, which the first nucleic acid encodes, is immunologically cross reactive with the polypeptide encoded by the second nucleic acid.

The terms "substantial identity" in the context of a peptide indicates that a peptide comprises a sequence with between 55-100% sequence identity to a reference sequence preferably at least 55% sequence identity, preferably 60% preferably 70%, more preferably 80%, most preferably at least 90% or 95% sequence identity to the reference sequence over a specified comparison window. Preferably, optimal alignment is conducted using the homology alignment algorithm of Needleman and Wunsch, supra. An indication that two peptide sequences are substantially identical is that one peptide is immunologically reactive with antibodies raised against the second peptide. Thus, a peptide is substantially identical to a second peptide, for example, where the two peptides differ only by a conservative substitution. In addition, a peptide can be substantially identical to a second peptide when they differ by a non-conservative change if the epitope that the antibody recognizes is substantially identical. Peptides which are "substantially similar" share sequences as noted above, except that residue positions which are not identical may differ by conservative amino acid changes.

MPG1 and the APS/ERF Superfamily of Transcription Factors

The ERF family is a large gene family of transcription factors and is part of the AP2/ERF superfamily, which also contains the AP2 and RAV families (Riechmann et al., 2000, Science 290: 2105-2110). The AP2/ERF superfamily is defined by the AP2/ERF domain, which consists of about 60 to 70 amino acids and is involved in DNA binding. These three families have been defined as follows. The AP2 family proteins contain two repeated AP2/ERF domains, the ERF family proteins contain a single AP2/ERF domain, and the RAV family proteins contain a B3 domain, which is a DNA-binding domain conserved in other plant-specific transcription factors, including VP1/ABI3, in addition to the single AP2/ERF domain. The ERF family is sometimes further divided into two major subfamilies, the ERF subfamily and the CBF/DREB subfamily (Sakuma et al., 2002, Biochem Biophys Res Commun 290: 998-1009). It has been demonstrated that the AP2/ERF proteins have important functions in the transcriptional regulation of a variety of biological processes related to growth and development, as well as various responses to environmental stimuli. Genes in the AP2 family have been shown to participate in the regulation of developmental processes, e.g. flower development (Elliott et al., 1996, Plant Cell 8: 155-168), spikelet meristem determinacy (Chuck et al., 1998 Genes Dev 12: 1145-1154), leaf epidermal cell identity (Moose and Sisco, 1996 Genes Dev 10: 3018-3027), and embryo development (Boutilier et al., 2002 Plant Cell 14: 1737-1749). Recently, the involvement of members of the RAV family in ethylene response (Alonso et al., 2003 Science 301: 653-657) and in brassinosteroid response (Hu et al., 2004 Cell Res 14: 8-15) was reported. After finding the tobacco ERFs (Ohme-Takagi and Shinshi, 1995 Plant Cell 7: 173-182), many proteins in the ERF family were identified and implicated in many diverse functions in cellular processes, such as hormonal signal transduction (Ohme-Takagi and Shinshi, 1995), response to biotic (Yamamoto et al., 1999 Plant J 20: 571-579; Gu et al., 2000 Plant Cell 12: 771-786) and abiotic stresses (Stockinger et al., 1997 Proc Natl Acad Sci USA 94: 1035-1040; Liu et al., 1998 Plant Cell 10: 1391-1406; Dubouzet et al., 2003 Plant J 33: 751-763), and regulation of metabolism (van der Fits and Memelink, 2000 Science 289: 295-297; Aharoni et al., 2004 Plant Cell 16: 2463-2480; Broun et al., 2004 Proc Natl Acad Sci USA 101: 4706-4711; Zhang et al., 2005 Plant J 42: 689-707), and in developmental processes (van der Graaff et al., 2000 Development 127: 4971-4980; Banno et al., 2001 Plant Cell 13: 2609-2618; Chuck et al., 2002 Science 298: 1238-1241) in various plant species. After the sequencing of the *Arabidopsis* genome was completed (*Arabidopsis* Genome Initiative, 2000), 145 genes were postulated to encode proteins containing the AP2/ERF domain, with 83% (121 genes) of these genes belonging to the ERF family (Sakuma et al., 2002 Biochem Biophys Res Commun 290: 998-1009). To date, most of the members of the ERF family have yet to be studied, despite the likelihood that these genes play important roles in many physiological aspects in plants. A great deal of experimental work will be required to determine the specific biological function of each of these genes. On the basis of phylogenetic analyses, it has become apparent that a large gene family of transcription factors consists of subgroups of genes that are closely related to each other (Kranz et al., 1998 Plant J 16: 263-276; Parenicova et al., 2003 Plant Cell 15: 1538-1551; Toledo-Ortiz et al., 2003 Plant Cell 15: 1749-1770; Reyes et al., 2004 Plant Physiol 134: 1718-1732; Tian et al., 2004 Plant Mol Biol 54: 519-532). At least two subfamilies were studied by Nakano et al. (Plant Physiology, February 2006, 140, pp. 411-432) CBF/DREB subfamily (Group A) and ERF subfamily (Group B) being those subfamilies further subdivided in classes.

Applicants have identified a novel putative AP2/ERF transcription factor which when overexpressed produces many favorable phenotypes in a plant without any deleterious consequences.

Nucleic Acids

The present invention provides, inter alia, isolated nucleic acids of RNA, DNA, homologs, paralogs and orthologs and/or chimeras thereof, comprising an MPG1 polynucleotide. This includes naturally occurring as well as synthetic variants and homologs of the sequences.

Sequences homologous, i.e., that share significant sequence identity or similarity, to those provided herein derived from maize, rice or from other plants of choice, are also an aspect of the invention. Homologous sequences can be derived from any plant including monocots and dicots and in particular agriculturally important plant species, including but not limited to, crops such as soybean, wheat, corn (maize), potato, cotton, rape, oilseed rape (including canola), sunflower, alfalfa, clover, sugarcane, and turf; or fruits and vegetables, such as banana, blackberry, blueberry, strawberry, and raspberry, cantaloupe, carrot, cauliflower, coffee, cucumber, eggplant, grapes, honeydew, lettuce, mango, melon, onion, *papaya*, peas, peppers, pineapple, pumpkin, spinach, squash, sweet corn, tobacco, tomato, tomatillo, watermelon, rosaceous fruits (such as apple, peach, pear, cherry and plum) and vegetable brassicas (such as broccoli, cabbage, cauliflower, Brussels sprouts, and kohlrabi). Other crops, including fruits and vegetables, whose phenotype can be changed and which comprise homologous sequences include barley; rye; millet; sorghum; currant; avocado; citrus fruits such as oranges, lemons, grapefruit and tangerines, artichoke, cherries; nuts such as the walnut and peanut; endive; leek; roots such as arrowroot, beet, cassava, turnip, radish, yam, and sweet potato; and beans. The homologous sequences may also be derived from woody species, such pine, poplar and *eucalyptus*, or mint or other labiates. In addition, homologous sequences may be derived from plants that are evolutionarily-related to crop plants, but which may not have yet been used as crop plants. Examples include deadly nightshade (*Atropa belladona*), related to tomato; jimson weed (*Datura strommium*), related to peyote; and teosinte (*Zea* species), related to corn (maize).

Orthologs and Paralogs

Homologous sequences as described above can comprise orthologous or paralogous sequences. Several different methods are known by those of skill in the art for identifying and defining these functionally homologous sequences. Three general methods for defining orthologs and paralogs are described; an ortholog, paralog or homolog may be identified by one or more of the methods described below.

Orthologs and paralogs are evolutionarily related genes that have similar sequence and similar functions. Orthologs are structurally related genes in different species that are derived by a speciation event. Paralogs are structurally related genes within a single species that are derived by a duplication event.

Within a single plant species, gene duplication may result in two copies of a particular gene, giving rise to two or more genes with similar sequence and often similar function known as paralogs. A paralog is therefore a similar gene formed by duplication within the same species. Paralogs typically cluster together or in the same clade (a group of similar genes) when a gene family phylogeny is analyzed using programs such as CLUSTAL (Thompson et al. (1994) Nucleic Acids Res. 22: 4673-4680; Higgins et al. (1996) Methods Enzymol. 266: 383-402). Groups of similar genes can also be identified with pair-wise BLAST analysis (Feng and Doolittle (1987) J. Mol. Evol. 25: 351-360).

For example, a clade of very similar MADS domain transcription factors from *Arabidopsis* all share a common function in flowering time (Ratcliffe et al. (2001) Plant Physiol. 126: 122-132), and a group of very similar AP2 domain transcription factors from *Arabidopsis* are involved in tolerance of plants to freezing (Gilmour et al. (1998) Plant J. 16: 433-442). Analysis of groups of similar genes with similar function that fall within one clade can yield sub-sequences that are particular to the clade. These sub-sequences, known as consensus sequences, can not only be used to define the sequences within each clade, but define the functions of these genes; genes within a clade may contain paralogous sequences, or orthologous sequences that share the same function (see also, for example, Mount (2001), in Bioinformatics: Sequence and Genome Analysis Cold Spring Harbor Laboratory Press, Cold Spring Harbor, N.Y., page 543.)

Speciation, the production of new species from a parental species, can also give rise to two or more genes with similar sequence and similar function. These genes, termed to orthologs, often have an identical function within their host plants and are often interchangeable between species without losing function. Because plants have common ancestors, many genes in any plant species will have a corresponding orthologous gene in another plant species. Once a phylogenic tree for a gene family of one species has been constructed using a program such as CLUSTAL (Thompson et al. (1994) *Nucleic Acids Res.* 22: 4673-4680; Higgins et al. (1996) supra) potential orthologous sequences can be placed into the phylogenetic tree and their relationship to genes from the species of interest can be determined. Orthologous sequences can also be identified by a reciprocal BLAST strategy. Once an orthologous sequence has been identified, the function of the ortholog can be deduced from the identified function of the reference sequence.

Orthologous genes from different organisms have highly conserved functions, and very often essentially identical functions (Lee et al. (2002) Genome Res. 12: 493-502; Remm et al. (2001) J. Mol. Biol. 314: 1041-1052). Paralogous genes, which have diverged through gene duplication, may retain similar functions of the encoded proteins. In such cases, paralogs can be used interchangeably with respect to certain embodiments of the instant invention (for example, transgenic expression of a coding sequence).

Variant Nucleotide Sequences in the Non-Coding Regions

The MPG1 nucleotide sequences are used to generate variant nucleotide sequences having the nucleotide sequence of the 5'-untranslated region, 3'-untranslated region, or promoter region that is approximately 70%, 75%, and 80%, 85%, 90% and 95% identical to the original nucleotide sequence. These variants are then associated with natural variation in the germplasm for component traits related to NUE. The associated variants are used as marker haplotypes to select for the desirable traits.

Variant Amino Acid Sequences of Polypeptides

Variant amino acid sequences of the MPG1 polypeptides are generated. In this example, one amino acid is altered. Specifically, the open reading frames are reviewed to determine the appropriate amino acid alteration. The selection of the amino acid to change is made by consulting the protein alignment (with the other orthologs and other gene family members from various species). An amino acid is selected that is deemed not to be under high selection pressure (not highly conserved) and which is rather easily substituted by an amino acid with similar chemical characteristics (i.e., similar functional side-chain). Using a protein alignment, an appropriate amino acid can be changed. Once the targeted amino acid is identified, the procedure outlined herein is followed. Variants having about 70%, 75%, 80%, 85%, 90% and 95% nucleic acid sequence identity are generated using this method. These variants are then associated with natural variation in the germplasm for component traits related to NUE. The associated variants are used as marker haplotypes to select for the desirable traits.

The present invention also includes polynucleotides optimized for expression in different organisms. For example, for expression of the polynucleotide in a particular plant, the sequence can be altered to account for specific codon.

The MPG1 nucleic acids which may be used for the present invention comprise isolated MPG1 polynucleotides which are inclusive of:

(a) a polynucleotide encoding an MPG1 polypeptide and conservatively modified and polymorphic variants thereof;
(b) a polynucleotide having at least 70% sequence identity with polynucleotides of (a) or (b);
(c) Complementary sequences of polynucleotides of (a) or (b).

In certain embodiments the nucleic acids includes at least one base substitution so that they do not recite naturally occurring nucleic acid sequences.

Construction of Nucleic Acids

The isolated nucleic acids of the present invention can be made using (a) standard recombinant methods, (b) synthetic techniques, or combinations thereof. In some embodiments, the polynucleotides of the present invention will be cloned, amplified, or otherwise constructed from a fungus or bacteria.

The nucleic acids may conveniently comprise sequences in addition to a polynucleotide of the present invention. For example, a multi-cloning site comprising one or more endonuclease restriction sites may be inserted into the nucleic acid to aid in isolation of the polynucleotide. Also, translatable sequences may be inserted to aid in the isolation of the translated polynucleotide of the present invention. For example, a hexa-histidine marker sequence provides a convenient means to purify the proteins of the present invention. The nucleic acid of the present invention—excluding the polynucleotide sequence—is optionally a vector, adapter, or linker for cloning and/or expression of a polynucleotide of the present invention. Additional sequences may be added to such cloning and/or expression sequences to optimize their function in cloning and/or expression, to aid in isolation of the polynucleotide, or to improve the introduction of the polynucleotide into a cell. Typically, the length of a nucleic acid of the present invention less the length of its polynucleotide of the present invention is less than 20 kilobase pairs, often less than 15 kb, and frequently less than 10 kb. Use of cloning vectors, expression vectors, adapters, and linkers is well known in the art. Exemplary nucleic acids include such vectors as: M13, lambda ZAP Express, lambda ZAP II, lambda gt10, lambda gt11, pBK-CMV, pBK-RSV, pBluescript II, lambda DASH II, lambda EMBL 3, lambda EMBL 4, pWE15, SuperCos 1, SurfZap, Uni-ZAP, pBC, pBS+/−, pSG5, pBK, pCR-Script, pET, pSPUTK, p3'SS, pGEM, pSK+/−, pGEX, pSPORTI and II, pOPRSVI CAT, pOPI3 CAT, pXT1, pSG5, pPbac, pMbac, pMClneo, pOG44, pOG45, pFRTβGAL, pNEOβGAL, pRS403, pRS404, pRS405, pRS406, pRS413, pRS414, pRS415, pRS416, lambda MOSSlox, and lambda MOSElox. Optional vectors for the present invention, include but are not limited to, lambda ZAP II, and pGEX. For a description of various nucleic acids see, e.g., Stratagene Cloning Systems, Catalogs 1995, 1996, 1997 (La Jolla, Calif.); and, Amersham Life Sciences, Inc, Catalog '97 (Arlington Heights, Ill.).

Synthetic Methods for Constructing Nucleic Acids

The isolated nucleic acids of the present invention can also be prepared by direct chemical synthesis by methods such as the phosphotriester method of Narang, et al., (1979) *Meth. Enzymol.* 68:90-9; the phosphodiester method of Brown, et al., (1979) *Meth. Enzymol.* 68:109-51; the diethylphosphoramidite method of Beaucage, et al., (1981) *Tetra. Letts.* 22(20):1859-62; the solid phase phosphoramidite triester method described by Beaucage, et al., supra, e.g., using an automated synthesizer, e.g., as described in Needham- VanDevanter, et al., (1984) *Nucleic Acids Res.* 12:6159-68; and, the solid support method of U.S. Pat. No. 4,458,066. Chemical synthesis generally produces a single stranded oligonucleotide. This may be converted into double stranded DNA by hybridization with a complementary sequence or by polymerization with a DNA polymerase using the single strand as a template. One of skill will recognize that while chemical synthesis of DNA is limited to sequences of about 100 bases, longer sequences may be obtained by the ligation of shorter sequences.

UTRs and Codon Preference

In general, translational efficiency has been found to be regulated by specific sequence elements in the 5' non-coding or untranslated region (5' UTR) of the RNA. Positive sequence motifs include translational initiation consensus sequences (Kozak, (1987) *Nucleic Acids Res.* 15:8125) and the 5<G>7 methyl GpppG RNA cap structure (Drummond, et al., (1985) *Nucleic Acids Res.* 13:7375). Negative elements include stable intramolecular 5' UTR stem-loop structures (Muesing, et al., (1987) *Cell* 48:691) and AUG sequences or short open reading frames preceded by an appropriate AUG in the 5' UTR (Kozak, supra, Rao, et al., (1988) *Mol. and Cell. Biol.* 8:284). Accordingly, the present invention provides 5' and/or 3' UTR regions for modulation of translation of heterologous coding sequences.

Further, the polypeptide-encoding segments of the polynucleotides of the present invention can be modified to alter codon usage. Altered codon usage can be employed to alter translational efficiency and/or to optimize the coding sequence for expression in a desired host or to optimize the codon usage in a heterologous sequence for expression in rice. Codon usage in the coding regions of the polynucleotides of the present invention can be analyzed statistically using commercially available software packages such as "Codon Preference" available from the University of Wisconsin Genetics Computer Group. See, Devereaux, et al., (1984) *Nucleic Acids Res.* 12:387-395); or MacVector 4.1 (Eastman Kodak Co., New Haven, Conn.). Thus, the present invention provides a codon usage frequency characteristic of the coding region of at least one of the polynucleotides of the present invention. The number of polynucleotides (3 nucleotides per amino acid) that can be used to determine a codon usage frequency can be any integer from 3 to the number of polynucleotides of the present invention as provided herein. Optionally, the polynucleotides will be full-length sequences. An exemplary number of sequences for statistical analysis can be at least 1, 5, 10, 20, 50 or 100.

Sequence Shuffling

The present invention provides methods for sequence shuffling using polynucleotides of the present invention, and compositions resulting therefrom. Sequence shuffling is described in PCT publication No. 96/19256. See also, Zhang, et al., (1997) *Proc. Natl. Acad. Sci. USA* 94:4504-9; and Zhao, et al., (1998) *Nature Biotech* 16:258-61. Generally, sequence shuffling provides a means for generating libraries of polynucleotides having a desired characteristic, which can be selected or screened for. Libraries of recombinant polynucleotides are generated from a population of related sequence polynucleotides, which comprise sequence regions, which have substantial sequence identity and can be homologously recombined in vitro or in vivo. The population of sequence-recombined polynucleotides comprises a subpopulation of polynucleotides which possess desired or advantageous characteristics and which can be selected by a suitable selection or screening method. The characteristics can be any property or attribute capable of being selected for or detected in a screening system, and may include properties of: an encoded protein, a transcriptional element, a sequence controlling transcription, RNA processing, RNA stability, chromatin conformation, translation, or other expression property of a gene or transgene, a replicative element, a protein-binding element, or the like, such as any feature which confers a selectable or detectable property. In some embodiments, the selected characteristic will be an altered $K_m$ and/or $K_{cat}$ over the wild-type protein as provided herein. In other embodiments, a protein or polynucleotide generated from sequence shuffling will have a ligand binding affinity greater than the non-shuffled wild-type polynucleotide. In yet other embodiments, a protein or polynucleotide generated from sequence shuffling will have an altered pH optimum as compared to the non-shuffled wild-type polynucleotide. The increase in such properties can be at least 110%, 120%, 130%, 140% or greater than 150% of the wild-type value.

Recombinant Expression Cassettes

The present disclosure further provides recombinant expression cassettes comprising a nucleic acid of the present disclosure. A nucleic acid sequence coding for the desired polynucleotide of the present disclosure, for example a cDNA or a genomic sequence encoding a polypeptide long enough to code for an active protein of the present disclosure, can be used to construct a recombinant expression cassette which can be introduced into the desired host cell. A recombinant expression cassette will typically comprise a polynucleotide of the present disclosure operably linked to transcriptional initiation regulatory sequences which will direct the transcription of the polynucleotide in the intended host cell, such as tissues of a transformed plant.

For example, plant expression vectors may include (1) a cloned plant gene under the transcriptional control of 5' and 3' regulatory sequences and (2) a dominant selectable marker. Such plant expression vectors may also contain, if desired, a promoter regulatory region (e.g., one conferring inducible or constitutive, environmentally- or developmentally-regulated, or cell- or tissue-specific/selective expression), a transcription initiation start site, a ribosome binding site, an RNA processing signal, a transcription termination site and/or a polyadenylation signal.

Promoters, Terminators, Introns

A plant promoter fragment can be employed which will direct expression of a polynucleotide of the present disclosure in essentially all tissues of a regenerated plant. Such promoters are referred to herein as "constitutive" promoters and are active under most environmental conditions and states of development or cell differentiation. Examples of constitutive promoters include the 1'- or 2'-promoter derived from T-DNA of *Agrobacterium tumefaciens*, the Smas promoter, the cinnamyl alcohol dehydrogenase promoter (U.S. Pat. No. 5,683,439), the Nos promoter, the rubisco promoter, the GRP1-8 promoter, the 35S promoter from cauliflower mosaic virus (CaMV), as described in Odell, et al., (1985) *Nature* 313:810-2; rice actin (McElroy, et al., (1990) *Plant Cell* 163-171); ubiquitin (Christensen, et al., (1992) *Plant Mol. Biol.* 12:619-632 and Christensen, et al., (1992) *Plant Mol. Biol.* 18:675-89); pEMU (Last, et al., (1991) *Theor. Appl. Genet.* 81:581-8); MAS (Velten, et al., (1984) *EMBO J.* 3:2723-30) and maize H3 histone (Lepetit, et al., (1992) *Mol. Gen. Genet.* 231:276-85 and Atanassvoa, et al., (1992) *Plant Journal* 2(3):291-300); ALS promoter, as described in PCT Application Number WO 1996/30530 and other transcription initiation regions from various plant genes known to those of skill. For the present disclosure ubiquitin is the preferred promoter for expression in monocot plants.

Alternatively, the plant promoter can direct expression of a polynucleotide of the present disclosure in a specific tissue or may be otherwise under more precise environmental or developmental control. Such promoters may be "inducible" promoters. Environmental conditions that may affect transcription by inducible promoters include pathogen attack, anaerobic conditions or the presence of light. Examples of inducible promoters are the Adh1 promoter, which is inducible by hypoxia or cold stress, the Hsp70 promoter, which is inducible by heat stress and the PPDK promoter, which is inducible by light. Diurnal promoters that are active at different times during the circadian rhythm are also known (US Patent Application Publication Number 2011/0167517, incorporated herein by reference).

Examples of promoters under developmental control include promoters that initiate transcription only, or preferentially, in certain tissues, such as leaves, roots, fruit, seeds or flowers. The operation of a promoter may also vary depending on its location in the genome. Thus, an inducible promoter may become fully or partially constitutive in certain locations.

If polypeptide expression is desired, it is generally desirable to include a polyadenylation region at the 3'-end of a polynucleotide coding region. The polyadenylation region can be derived from a variety of plant genes, or from T-DNA. The 3' end sequence to be added can be derived from, for example, the nopaline synthase or octopine synthase genes or alternatively from another plant gene or less preferably from any other eukaryotic gene. Examples of such regulatory elements include, but are not limited to, 3' termination and/or polyadenylation regions such as those of the *Agrobacterium tumefaciens* nopaline synthase (nos) gene (Bevan, et al., (1983) Nucleic Acids Res. 12:369-85); the potato proteinase inhibitor II (PINII) gene (Keil, et al., (1986) Nucleic Acids Res. 14:5641-50 and An, et al., (1989) Plant Cell 1:115-22) and the CaMV 19S gene (Mogen, et al., (1990) Plant Cell 2:1261-72).

An intron sequence can be added to the 5' untranslated region or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold (Buchman and Berg, (1988) Mol. Cell Biol. 8:4395-4405; Callis, et al., (1987) Genes Dev. 1:1183-200). Such intron enhancement of gene expression is typically greatest when placed near the 5' end of the transcription unit. Use of maize introns Adh1-S intron 1, 2 and 6, the Bronze-1 intron are known in the art. See generally, The Maize Handbook, Chapter 116, Freeling and Walbot, eds., Springer, New York (1994).

Signal Peptide Sequences

Plant signal sequences, including, but not limited to, signal-peptide encoding DNA/RNA sequences which target proteins to the extracellular matrix of the plant cell (Dratewka-Kos, et al., (1989) *J. Biol. Chem.* 264:4896-900), such as the *Nicotiana plumbaginifolia* extension gene (DeLoose, et al., (1991) Gene 99:95-100); signal peptides which target proteins to the vacuole, such as the sweet potato sporamin gene (Matsuka, et al., (1991) Proc. Natl. Acad. Sci. USA 88:834) and the barley lectin gene (Wilkins, et al., (1990) Plant Cell, 2:301-13); signal peptides which cause proteins to be secreted, such as that of PRIb (Lind, et al., (1992) Plant Mol. Biol. 18:47-53) or the barley alpha amylase (BAA) (Rahmatullah, et al., (1989) Plant Mol. Biol. 12:119) or signal peptides which target proteins to the plastids such as that of rapeseed enoyl-Acp reductase (Verwaert, et al., (1994) Plant Mol. Biol. 26:189-202) are useful in the disclosure.

Markers

The vector comprising the sequences from a polynucleotide of the present disclosure will typically comprise a marker gene, which confers a selectable phenotype on plant cells. The selectable marker gene may encode antibiotic resistance, with suitable genes including genes coding for resistance to the antibiotic spectinomycin (e.g., the aada gene), the streptomycin phosphotransferase (SPT) gene coding for streptomycin resistance, the neomycin phosphotransferase (NPTII) gene encoding kanamycin or geneticin resistance, the hygromycin phosphotransferase (HPT) gene coding for hygromycin resistance. Also useful are genes coding for resistance to herbicides which act to inhibit the action of acetolactate synthase (ALS), in particular the sulfonylurea-type herbicides (e.g., the acetolactate synthase (ALS) gene containing mutations leading to such resistance in particular the S4 and/or Hra mutations), genes coding for resistance to herbicides which act to inhibit action of glutamine synthase, such as phosphinothricin or basta (e.g., the bar gene), or other such genes known in the art. The bar gene encodes resistance to the herbicide basta and the ALS gene encodes resistance to the herbicide chlorsulfuron.

Constructs described herein may comprise a polynucleotide of interest encoding a reporter or marker product. Examples of suitable reporter polynucleotides known in the art can be found in, for example, Jefferson, et al., (1991) in Plant Molecular Biology Manual, ed. Gelvin, et al., (Kluwer Academic Publishers), pp. 1-33; DeWet, et al. (1987) Mol. Cell. Biol. 7:725-737; Goff, et al., (1990) EMBO J. 9:2517-2522; Kain, et al., (1995) Bio Techniques 19:650-655 and Chiu, et al., (1996) Current Biology 6:325-330. In certain embodiments, the polynucleotide of interest encodes a selectable reporter. These can include polynucleotides that confer antibiotic resistance or resistance to herbicides. Examples of suitable selectable marker polynucleotides include, but are not limited to, genes encoding resistance to chloramphenicol, methotrexate, hygromycin, streptomycin, spectinomycin, bleomycin, sulfonamide, bromoxynil, glyphosate and phosphinothricin.

In some embodiments, the expression cassettes disclosed herein comprise a polynucleotide of interest encoding scorable or screenable markers, where presence of the polynucleotide produces a measurable product. Examples include a β-glucuronidase, or uidA gene (GUS), which encodes an enzyme for which various chromogenic substrates are known (for example, U.S. Pat. Nos. 5,268,463 and 5,599,670); chloramphenicol acetyl transferase and alkaline phosphatase. Other screenable markers include the anthocyanin/flavonoid polynucleotides including, for example, a R-locus polynucleotide, which encodes a product that regulates the production of anthocyanin pigments (red color) in plant tissues, the genes which control biosynthesis of flavonoid pigments, such as the maize C1 and C2, the B gene, the p1 gene and the bronze locus genes, among others. Further examples of suitable markers encoded by polynucleotides of interest include the cyan fluorescent protein (CYP) gene, the yellow fluorescent protein gene, a lux gene, which encodes a luciferase, the presence of which may be detected using, for example, X-ray film, scintillation counting, fluorescent spectrophotometry, low-light video cameras, photon counting cameras or multiwell luminometry, a green fluorescent protein (GFP) and DsRed2 (Clontechniques, 2001) where plant cells transformed with the marker gene are red in color, and thus visually selectable. Additional examples include a p-lactamase gene encoding an enzyme for which various chromogenic substrates are known (e.g., PADAC, a chromogenic cephalosporin), a xylE gene encoding a catechol dioxygenase that can convert chromogenic catechols, an α-amylase gene and a tyrosinase gene encoding an enzyme capable of oxidizing tyrosine to DOPA and dopaquinone, which in turn condenses to form the easily detectable compound melanin.

The expression cassette can also comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). Additional selectable markers include phenotypic markers such as β-galactosidase and fluorescent proteins such as green fluorescent protein (GFP) (Su, et al., (2004) Biotechnol Bioeng 85:610-9 and Fetter, et al., (2004) Plant Cell 16:215-28), cyan florescent protein (CYP) (Bolte, et al., (2004) J. Cell Science 117:943-54 and Kato, et al., (2002) Plant Physiol 129:913-42) and yellow florescent protein (PhiYFP® from Evrogen, see, Bolte, et al., (2004) J. Cell Science 117:943-54). For additional selectable markers, see generally, Yarranton, (1992) Curr. Opin. Biotech. 3:506-511; Christopherson, et al., (1992) Proc. Natl. Acad. Sci. USA 89:6314-6318; Yao, et al., (1992) Cell 71:63-72; Reznikoff, (1992) Mol. Microbiol. 6:2419-2422; Barkley, et al., (1980) in The Operon, pp. 177-220; Hu, et al., (1987) Cell 48:555-566; Brown, et al., (1987) Cell 49:603-612; Figge, et al., (1988) Cell 52:713-722; Deuschle, et al., (1989) Proc. Natl. Acad. Aci. USA 86:5400-5404; Fuerst, et al., (1989) Proc. Natl. Acad. Sci. USA 86:2549-2553; Deuschle, et al., (1990) Science 248:480-483; Gossen, (1993) Ph.D. Thesis, University of Heidelberg; Reines, et al., (1993) Proc. Natl. Acad. Sci. USA 90:1917-1921; Labow, et al., (1990) Mol. Cell. Biol. 10:3343-3356; Zambretti, et al., (1992) Proc. Natl. Acad. Sci. USA 89:3952-3956; Bairn, et al., (1991) Proc. Natl. Acad. Sci. USA 88:5072-5076; Wyborski, et al., (1991) Nucleic Acids Res. 19:4647-4653; Hillenand-Wissman, (1989) Topics Mol. Struc. Biol. 10:143-162; Degenkolb, et al., (1991) Antimicrob. Agents Chemother. 35:1591-1595; Kleinschnidt, et al., (1988) Biochemistry 27:1094-1104; Bonin, (1993) Ph.D. Thesis, University of Heidelberg; Gossen, et al., (1992) Proc. Natl. Acad. Sci. USA 89:5547-5551; Oliva, et al., (1992) Antimicrob. Agents Chemother. 36:913-919; Hlavka, et al., (1985) Handbook of Experimental Pharmacology, Vol. 78 (Springer-Verlag, Berlin); Gill, et al., (1988) Nature 334:721-724. Such disclosures are herein incorporated by reference. The above list of selectable marker genes is not meant to be limiting. Any selectable marker gene can be used in the compositions and methods disclosed herein.

Typical vectors useful for expression of genes in higher plants are well known in the art and include vectors derived from the tumor-inducing (Ti) plasmid of *Agrobacterium tumefaciens* described by Rogers, et al., (1987) Meth. Enzymol. 153:253-77. These vectors are plant integrating vectors in that on transformation, the vectors integrate a portion of vector DNA into the genome of the host plant. Exemplary *A. tumefaciens* vectors useful herein are plasmids pKYLX6 and pKYLX7 of Schardl, et al., (1987) Gene 61:1-11 and Berger, et al., (1989) Proc. Natl. Acad. Sci. USA, 86:8402-6.

Another useful vector herein is plasmid pBI101.2 that is available from CLONTECH Laboratories, Inc. (Palo Alto, Calif.).

Expression of Proteins in Host Cells

Using the nucleic acids of the present invention, one may express a protein of the present invention in a recombinantly engineered cell such as bacteria, yeast, insect, mammalian, or preferably plant cells. The cells produce the protein in a non-natural condition (e.g., in quantity, composition, location, and/or time), because they have been genetically altered through human intervention to do so.

It is expected that those of skill in the art are knowledgeable in the numerous expression systems available for expression of a nucleic acid encoding a protein of the present invention. No attempt to describe in detail the various methods known for the expression of proteins in prokaryotes or eukaryotes will be made.

In brief summary, the expression of isolated nucleic acids encoding a protein of the present invention will typically be achieved by operably linking, for example, the DNA or cDNA to a promoter (which is either constitutive or inducible), followed by incorporation into an expression vector. The vectors can be suitable for replication and integration in either prokaryotes or eukaryotes. Typical expression vectors contain transcription and translation terminators, initiation sequences, and promoters useful for regulation of the expression of the DNA encoding a protein of the present invention. To obtain high level expression of a cloned gene, it is desirable to construct expression vectors which contain, at the minimum, a strong promoter, such as ubiquitin, to direct transcription, a ribosome binding site for translational initiation, and a transcription/translation terminator. Constitutive promoters are classified as providing for a range of constitutive expression. Thus, some are weak constitutive promoters, and others are strong constitutive promoters. Generally, by "weak promoter" is intended a promoter that drives expression of a coding sequence at a low level. By "low level" is intended at levels of about 1/10,000 transcripts to about 1/100,000 transcripts to about 1/500,000 transcripts. Conversely, a "strong promoter" drives expression of a coding sequence at a "high level," or about 1/10 transcripts to about 1/100 transcripts to about 1/1,000 transcripts.

In additional embodiments, enhancer elements may be introduced which increase expression of the polynucleotides of the invention.

One of skill would recognize that modifications could be made to a protein of the present invention without diminishing its biological activity. Some modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids (e.g., poly His) placed on either terminus to create conveniently located restriction sites or termination codons or purification sequences.

Expression in Prokaryotes

Prokaryotic cells may be used as hosts for expression. Prokaryotes most frequently are represented by various strains of *E. coli*; however, other microbial strains may also be used. Commonly used prokaryotic control sequences which are defined herein to include promoters for transcription initiation, optionally with an operator, along with ribosome binding site sequences, include such commonly used promoters as the beta lactamase (penicillinase) and lactose (lac) promoter systems (Chang, et al., (1977) *Nature* 198:

1056), the tryptophan (trp) promoter system (Goeddel, et al., (1980) *Nucleic Acids Res.* 8:4057) and the lambda derived P L promoter and N-gene ribosome binding site (Shimatake, et al., (1981) *Nature* 292:128). The inclusion of selection markers in DNA vectors transfected in *E. coli* is also useful. Examples of such markers include genes specifying resistance to ampicillin, tetracycline, or chloramphenicol.

The vector is selected to allow introduction of the gene of interest into the appropriate host cell. Bacterial vectors are typically of plasmid or phage origin. Appropriate bacterial cells are infected with phage vector particles or transfected with naked phage vector DNA. If a plasmid vector is used, the bacterial cells are transfected with the plasmid vector DNA. Expression systems for expressing a protein of the present invention are available using *Bacillus* sp. and *Salmonella* (Palva, et al., (1983) *Gene* 22:229-35; Mosbach, et al., (1983) *Nature* 302:543-5). The pGEX-4T-1 plasmid vector from Pharmacia is the preferred *E. coli* expression vector for the present invention.

Expression in Eukaryotes

A variety of eukaryotic expression systems such as yeast, insect cell lines, plant and mammalian cells, are known to those of skill in the art. As explained briefly below, the present invention can be expressed in these eukaryotic systems. In some embodiments, transformed/transfected plant cells, as discussed infra, are employed as expression systems for production of the proteins of the instant invention.

Synthesis of heterologous proteins in yeast is well known. Sherman, et al., (1982) *Methods in Yeast Genetics*, Cold Spring Harbor Laboratory is a well-recognized work describing the various methods available to produce the protein in yeast. Two widely utilized yeasts for production of eukaryotic proteins are *Saccharomyces cerevisiae* and *Pichia pastoris*. Vectors, strains, and protocols for expression in *Saccharomyces* and *Pichia* are known in the art and available from commercial suppliers (e.g., Invitrogen). Suitable vectors usually have expression control sequences, such as promoters, including 3-phosphoglycerate kinase or alcohol oxidase, and an origin of replication, termination sequences and the like as desired.

A protein of the present invention, once expressed, can be isolated from yeast by lysing the cells and applying standard protein isolation techniques to the lysates or the pellets. The monitoring of the purification process can be accomplished by using Western blot techniques or radioimmunoassay of other standard immunoassay techniques.

The sequences encoding proteins of the present invention can also be ligated to various expression vectors for use in transfecting cell cultures of, for instance, mammalian, insect, or plant origin. Mammalian cell systems often will be in the form of monolayers of cells although mammalian cell suspensions may also be used. A number of suitable host cell lines capable of expressing intact proteins have been developed in the art, and include the HEK293, BHK21, and CHO cell lines. Expression vectors for these cells can include expression control sequences, such as an origin of replication, a promoter (e.g., the CMV promoter, a HAS tk promoter or pgk (phosphoglycerate kinase) promoter), an enhancer (Queen, et al., (1986) *Immunol. Rev.* 89:49), and necessary processing information sites, such as ribosome binding sites, RNA splice sites, polyadenylation sites (e.g., an SV40 large T Ag poly A addition site), and transcriptional terminator sequences. Other animal cells useful for production of proteins of the present invention are available, for instance, from the American Type Culture Collection Catalogue of Cell Lines and Hybridomas (7$^{th}$ ed., 1992).

Appropriate vectors for expressing proteins of the present invention in insect cells are usually derived from the SF9 baculovirus. Suitable insect cell lines include mosquito larvae, silkworm, armyworm, moth, and *Drosophila* cell lines such as a Schneider cell line (see, e.g., Schneider, (1987) *J. Embryol. Exp. Morphol.* 27:353-65).

As with yeast, when higher animal or plant host cells are employed, polyadenlyation or transcription terminator sequences are typically incorporated into the vector. An example of a terminator sequence is the polyadenylation sequence from the bovine growth hormone gene. Sequences for accurate splicing of the transcript may also be included. An example of a splicing sequence is the VP1 intron from SV40 (Sprague et al., *J. Virol.* 45:773-81 (1983)). Additionally, gene sequences to control replication in the host cell may be incorporated into the vector such as those found in bovine papilloma virus type-vectors (Saveria-Campo, "Bovine Papilloma Virus DNA a Eukaryotic Cloning Vector," in *DNA Cloning: A Practical Approach*, vol. II, Glover, ed., IRL Press, Arlington, Va., pp. 213-38 (1985)).

In addition, the MPG1 gene placed in the appropriate plant expression vector can be used to transform plant cells. The polypeptide can then be isolated from plant callus or the transformed cells can be used to regenerate transgenic plants. Such transgenic plants can be harvested, and the appropriate tissues (seed or leaves, for example) can be subjected to large scale protein extraction and purification techniques.

Plant Transformation Methods

Numerous methods for introducing foreign genes into plants are known and can be used to insert an MPG1 polynucleotide into a plant host, including biological and physical plant transformation protocols. See, e.g., Miki et al., "Procedure for Introducing Foreign DNA into Plants," in *Methods in Plant Molecular Biology and Biotechnology*, Glick and Thompson, eds., CRC Press, Inc., Boca Raton, pp. 67-88 (1993). The methods chosen vary with the host plant, and include chemical transfection methods such as calcium phosphate, microorganism-mediated gene transfer such as *Agrobacterium* (Horsch et al., *Science* 227:1229-31 (1985)), electroporation, micro-injection, and biolistic bombardment.

Expression cassettes and vectors and in vitro culture methods for plant cell or tissue transformation and regeneration of plants are known and available. See, e.g., Gruber et al., "Vectors for Plant Transformation," in *Methods in Plant Molecular Biology and Biotechnology*, supra, pp. 89-119.

The isolated polynucleotides or polypeptides may be introduced into the plant by one or more techniques typically used for direct delivery into cells. Such protocols may vary depending on the type of organism, cell, plant or plant cell, i.e. monocot or dicot, targeted for gene modification. Suitable methods of transforming plant cells include microinjection (Crossway, et al., (1986) *Biotechniques* 4:320-334; and U.S. Pat. No. 6,300,543), electroporation (Riggs, et al., (1986) *Proc. Natl. Acad. Sci. USA* 83:5602-5606, direct gene transfer (Paszkowski et al., (1984) *EMBO J* 3:2717-2722), and ballistic particle acceleration (see, for example, Sanford, et al., U.S. Pat. No. 4,945,050; WO 91/10725; and McCabe, et al., (1988) *Biotechnology* 6:923-926). Also see, Tomes, et al., "*Direct DNA Transfer into Intact Plant Cells Via Microprojectile Bombardment*". pp. 197-213 in Plant Cell, Tissue and Organ Culture, Fundamental Methods. eds. O. L. Gamborg & G. C. Phillips. Springer-Verlag Berlin Heidelberg New York, 1995; U.S. Pat. No. 5,736,369 (meristem); Weissinger, et al., (1988) *Ann. Rev. Genet.* 22:421-477; Sanford, et al., (1987) *Particulate Science and Technology*

5:27-37 (onion); Christou, et al., (1988) *Plant Physiol.* 87:671-674 (soybean); Datta, et al., (1990) *Biotechnology* 8:736-740 (rice); Klein, et al., (1988) *Proc. Natl. Acad. Sci. USA* 85:4305-4309 (maize); Klein, et al., (1988) *Biotechnology* 6:559-563 (maize); WO 91/10725 (maize); Klein, et al., (1988) *Plant Physiol.* 91:440-444 (maize); Fromm, et al., (1990) *Biotechnology* 8:833-839; and Gordon-Kamm, et al., (1990) *Plant Cell* 2:603-618 (maize); Hooydaas-Van Slogteren & Hooykaas (1984) *Nature* (London) 311:763-764; Bytebierm, et al., (1987) *Proc. Natl. Acad. Sci. USA* 84:5345-5349 (Liliaceae); De Wet, et al., (1985) In The Experimental Manipulation of Ovule Tissues, ed. G. P. Chapman, et al., pp. 197-209. Longman, N Y (pollen); Kaeppler, et al., (1990) *Plant Cell Reports* 9:415-418; and Kaeppler, et al., (1992) *Theor. Appl. Genet.* 84:560-566 (whisker-mediated transformation); U.S. Pat. No. 5,693,512 (sonication); D'Halluin, et al., (1992) *Plant Cell* 4:1495-1505 (electroporation); Li, et al., (1993) *Plant Cell Reports* 12:250-255; and Christou and Ford, (1995) *Annals of Botany* 75:407-413 (rice); Osjoda, et al., (1996) *Nature Biotech.* 14:745-750; *Agrobacterium* mediated maize transformation (U.S. Pat. No. 5,981,840); silicon carbide whisker methods (Frame, et al., (1994) *Plant* 6:941-948); laser methods (Guo, et al., (1995) *Physiologia Plantarum* 93:19-24); sonication methods (Bao, et al., (1997) *Ultrasound in Medicine & Biology* 23:953-959; Finer and Finer, (2000) *Lett Appl Microbiol.* 30:406-10; Amoah, et al., (2001) *J Exp Bot* 52:1135-42); polyethylene glycol methods (Krens, et al., (1982) *Nature* 296:72-77); protoplasts of monocot and dicot cells can be transformed using electroporation (Fromm, et al., (1985) *Proc. Natl. Acad. Sci. USA* 82:5824-5828) and microinjection (Crossway, et al., (1986) *Mol. Gen. Genet.* 202:179-185); all of which are herein incorporated by reference.

*Agrobacterium*-Mediated Transformation

The most widely utilized method for introducing an expression vector into plants is based on the natural transformation system of *Agrobacterium*. *A. tumefaciens* and *A. rhizogenes* are plant pathogenic soil bacteria, which genetically transform plant cells. The Ti and Ri plasmids of *A. tumefaciens* and *A. rhizogenes*, respectively, carry genes responsible for genetic transformation of plants. See, e.g., Kado, (1991) *Crit. Rev. Plant Sci.* 10:1. Descriptions of the *Agrobacterium* vector systems and methods for *Agrobacterium*-mediated gene transfer are provided in Gruber, et al., supra; Miki, et al., supra; and Moloney, et al., (1989) *Plant Cell Reports* 8:238.

Similarly, the gene can be inserted into the T-DNA region of a Ti or Ri plasmid derived from *A. tumefaciens* or *A. rhizogenes*, respectively. Thus, expression cassettes can be constructed as above, using these plasmids. Many control sequences are known which when coupled to a heterologous coding sequence and transformed into a host organism show fidelity in gene expression with respect to tissue/organ specificity of the original coding sequence. See, e.g., Benfey and Chua, (1989) *Science* 244:174-81. Particularly suitable control sequences for use in these plasmids are promoters for constitutive leaf-specific expression of the gene in the various target plants. Other useful control sequences include a promoter and terminator from the nopaline synthase gene (NOS). The NOS promoter and terminator are present in the plasmid pARC2, available from the American Type Culture Collection and designated ATCC 67238. If such a system is used, the virulence (vir) gene from either the Ti or Ri plasmid must also be present, either along with the T-DNA portion, or via a binary system where the vir gene is present on a separate vector. Such systems, vectors for use therein, and methods of transforming plant cells are described in U.S. Pat. No. 4,658,082; U.S. Patent Application No. 913, 914, filed Oct. 1, 1986, as referenced in U.S. Pat. No. 5,262,306, issued Nov. 16, 1993; and Simpson, et al., (1986) *Plant Mol. Biol.* 6:403-15 (also referenced in the '306 patent); all incorporated by reference in their entirety.

Once constructed, these plasmids can be placed into *A. rhizogenes* or *A. tumefaciens* and these vectors used to transform cells of plant species, which are ordinarily susceptible to *Fusarium* or *Alternaria* infection. Several other transgenic plants are also contemplated by the present invention including but not limited to soybean, corn, sorghum, alfalfa, rice, clover, cabbage, banana, coffee, celery, tobacco, cowpea, cotton, melon and pepper. The selection of either *A. tumefaciens* or *A. rhizogenes* will depend on the plant being transformed thereby. In general *A. tumefaciens* is the preferred organism for to transformation. Most dicotyledonous plants, some gymnosperms, and a few monocotyledonous plants (e.g., certain members of the Liliales and Arales) are susceptible to infection with *A. tumefaciens*. *A. rhizogenes* also has a wide host range, embracing most dicots and some gymnosperms, which includes members of the Leguminosae, Compositae, and Chenopodiaceae. Monocot plants can now be transformed with some success. European Patent Application No. 604 662 A1 discloses a method for transforming monocots using *Agrobacterium*. European Application No. 672 752 A1 discloses a method for transforming monocots with *Agrobacterium* using the scutellum of immature embryos. Ishida, et al., discuss a method for transforming maize by exposing immature embryos to *A. tumefaciens* (Nature Biotechnology 14:745-50 (1996)).

Once transformed, these cells can be used to regenerate transgenic plants. For example, whole plants can be infected with these vectors by wounding the plant and then introducing the vector into the wound site. Any part of the plant can be wounded, including leaves, stems and roots. Alternatively, plant tissue, in the form of an explant, such as cotyledonary tissue or leaf disks, can be inoculated with these vectors, and cultured under conditions, which promote plant regeneration. Roots or shoots transformed by inoculation of plant tissue with *A. rhizogenes* or *A. tumefaciens*, containing the gene coding for the fumonisin degradation enzyme, can be used as a source of plant tissue to regenerate fumonisin-resistant transgenic plants, either via somatic embryogenesis or organogenesis. Examples of such methods for regenerating plant tissue are disclosed in Shahin, (1985) *Theor. Appl. Genet.* 69:235-40; U.S. Pat. No. 4,658,082; Simpson, et al., supra; and U.S. Patent Application Nos. 913,913 and 913,914, both filed Oct. 1, 1986, as referenced in U.S. Pat. No. 5,262,306, issued Nov. 16, 1993, the entire disclosures therein incorporated herein by reference.

Direct Gene Transfer

Despite the fact that the host range for *Agrobacterium*-mediated transformation is broad, some major cereal crop species and gymnosperms have generally been recalcitrant to this mode of gene transfer, even though some success has recently been achieved in rice (Hiei, et al., (1994) *The Plant Journal* 6:271-82). Several methods of plant transformation, collectively referred to as direct gene transfer, have been developed as an alternative to *Agrobacterium*-mediated transformation.

A generally applicable method of plant transformation is microprojectile-mediated transformation, where DNA is carried on the surface of microprojectiles measuring about 1 to 4 μm. The expression vector is introduced into plant tissues with a biolistic device that accelerates the microprojectiles to speeds of 300 to 600 m/s which is sufficient to penetrate the plant cell walls and membranes (Sanford, et al., (1987) *Part. Sci. Technol.* 5:27; Sanford, (1988) *Trends Biotech* 6:299; Sanford, (1990) *Physiol. Plant* 79:206; and Klein, et al., (1992) *Biotechnology* 10:268).

Another method for physical delivery of DNA to plants is sonication of target cells as described in Zang, et al., (1991) *BioTechnology* 9:996. Alternatively, liposome or spheroplast fusions have been used to introduce expression vectors into plants. See, e.g., Deshayes, et al., (1985) *EMBO J.* 4:2731; and Christou, et al., (1987) *Proc. Natl. Acad. Sci. USA* 84:3962. Direct uptake of DNA into protoplasts using $CaCl_2$ precipitation, polyvinyl alcohol, or poly-L-ornithine has also been reported. See, e.g., Hain, et al., (1985) *Mol. Gen. Genet.* 199:161; and Draper, et al., (1982) *Plant Cell Physiol.* 23:451.

Electroporation of protoplasts and whole cells and tissues has also been described. See, e.g., Donn, et al., (1990) Abstracts of the VIIth Int'l. Congress on Plant Cell and Tissue Culture IAPTC, A2-38, p. 53; D'Halluin, et al., (1992) *Plant Cell* 4:1495-505; and Spencer, et al., (1994) *Plant Mol. Biol.* 24:51-61.

Reducing the Activity of an MPG1 Polypeptide

In certain embodiments the invention may include modulation of the MPG1 gene to reduce or eliminate the activity of an MPG1 polypeptide, perhaps during certain developmental stages or tissues etc., by transforming a plant cell with an expression cassette that expresses a polynucleotide that inhibits the expression of the MPG1 polypeptide. The polynucleotide may inhibit the expression of the MPG1 polypeptide directly, by preventing transcription or translation of the MPG1 messenger RNA, or indirectly, by encoding a polypeptide that inhibits the transcription or translation of an MPG1 gene encoding an MPG1 polypeptide. Methods for inhibiting or eliminating the expression of a gene in a plant are well known in the art, and any such method may be used in the present invention to inhibit the expression of the MPG1 polypeptide. Many methods may be used to reduce or eliminate the activity of an MPG1 polypeptide. In addition, more than one method may be used to reduce the activity of a single MPG1 polypeptide.

1. Polynucleotide-Based Methods:

In some embodiments of the present invention, a plant is transformed with an expression cassette that is capable of expressing a polynucleotide that inhibits the expression of an MPG1 polypeptide of the invention. The term "expression" as used herein refers to the biosynthesis of a gene product, including the transcription and/or translation of said gene product. For example, for the purposes of the present invention, an expression cassette capable of expressing a polynucleotide that inhibits the expression of at least one MPG1 polypeptide is an expression cassette capable of producing an RNA molecule that inhibits the transcription and/or translation of at least one MPG1 polypeptide of the invention. The "expression" or "production" of a protein or polypeptide from a DNA molecule refers to the transcription and translation of the coding sequence to produce the protein or polypeptide, while the "expression" or "production" of a protein or polypeptide from an RNA molecule refers to the translation of the RNA coding sequence to produce the protein or polypeptide.

Examples of polynucleotides that inhibit the expression of an MPG1 polypeptide are given below.

i. Sense Suppression/Cosuppression

In some embodiments of the invention, inhibition of the expression of an MPG1 polypeptide may be obtained by sense suppression or cosuppression. For cosuppression, an expression cassette is designed to express an RNA molecule corresponding to all or part of a messenger RNA encoding an MPG1 polypeptide in the "sense" orientation. Over expression of the RNA molecule can result in reduced expression of the native gene. Accordingly, multiple plant lines transformed with the cosuppression expression cassette are screened to identify those that show the greatest inhibition of MPG1 polypeptide expression.

The polynucleotide used for cosuppression may correspond to all or part of the sequence encoding the MPG1 polypeptide, all or part of the 5' and/or 3' untranslated region of an MPG1 polypeptide transcript, or all or part of both the coding sequence and the untranslated regions of a transcript encoding an MPG1 polypeptide. In some embodiments where the polynucleotide comprises all or part of the coding region for the MPG1 polypeptide, the expression cassette is designed to eliminate the start codon of the polynucleotide so that no protein product will be translated.

Cosuppression may be used to inhibit the expression of plant genes to produce plants having undetectable protein levels for the proteins encoded by these genes. See, for example, Broin, et al., (2002) *Plant Cell* 14:1417-1432. Cosuppression may also be used to inhibit the expression of multiple proteins in the same plant. See, for example, U.S. Pat. No. 5,942,657. Methods for using cosuppression to inhibit the expression of endogenous genes in plants are described in Flavell, et al., (1994) *Proc. Natl. Acad. Sci. USA* 91:3490-3496; Jorgensen, et al., (1996) *Plant Mol. Biol.* 31:957-973; Johansen and Carrington, (2001) *Plant Physiol.* 126:930-938; Broin, et al., (2002) *Plant Cell* 14:1417-1432; Stoutjesdijk, et al., (2002) *Plant Physiol.* 129:1723-1731; Yu, et al., (2003) *Phytochemistry* 63:753-763; and U.S. Pat. Nos. 5,034,323, 5,283,184, and 5,942,657; each of which is herein incorporated by reference. The efficiency of cosuppression may be increased by including a poly-dT region in the expression cassette at a position 3' to the sense sequence and 5' of the polyadenylation signal. See, U.S. Patent Publication No. 20020048814, herein incorporated by reference. Typically, such a nucleotide sequence has substantial sequence identity to the sequence of the transcript of the endogenous gene, optimally greater than about 65% sequence identity, more optimally greater than about 85% sequence identity, most optimally greater than about 95% sequence identity. See U.S. Pat. Nos. 5,283,184 and 5,034,323; herein incorporated by reference.

ii. Antisense Suppression

In some embodiments of the invention, inhibition of the expression of the MPG1 polypeptide may be obtained by antisense suppression. For antisense suppression, the expression cassette is designed to express an RNA molecule complementary to all or part of a messenger RNA encoding the MPG1 polypeptide. Over expression of the antisense RNA molecule can result in reduced expression of the native gene. Accordingly, multiple plant lines transformed with the antisense suppression expression cassette are screened to identify those that show the greatest inhibition MPG1 polypeptide expression. The polynucleotide for use in antisense suppression may correspond to all or part of the complement of the sequence encoding the MPG1 polypeptide, all or part of the complement of the 5' and/or 3' untranslated region of the MPG1 MPG1 transcript, or all or part of the complement of both the coding sequence and the untranslated regions of a transcript encoding the MPG1 polypeptide. In addition, the antisense polynucleotide may be fully complementary (i.e., 100% identical to the complement of the target sequence) or partially complementary (i.e., less than 100% identical to the complement of the target sequence) to the target sequence.

Antisense suppression may be used to inhibit the expression of multiple proteins in the same plant. See, for example, U.S. Pat. No. 5,942,657. Furthermore, portions of the antisense nucleotides may be used to disrupt the expression of the target gene. Generally, sequences of at least 50 nucleotides, 100 nucleotides, 200 nucleotides, 300, 400, 450, 500, 550, or greater may be used. Methods for using antisense suppression to inhibit the expression of endogenous genes in plants are described, for example, in Liu, et al., (2002) *Plant Physiol.* 129:1732-1743 and U.S. Pat. Nos. 5,759,829 and 5,942,657, each of which is herein incorporated by reference. Efficiency of antisense suppression may be increased by including a poly-dT region in the expression cassette at a position 3' to the antisense sequence and 5' of the polyadenylation signal. See, U.S. Patent Publication No. 20020048814, herein incorporated by reference.

Double-Stranded RNA Interference

In some embodiments of the invention, inhibition of the expression of an MPG1 polypeptide may be obtained by double-stranded RNA (dsRNA) interference. For dsRNA interference, a sense RNA molecule like that described above for cosuppression and an antisense RNA molecule that is fully or partially complementary to the sense RNA molecule are expressed in the same cell, resulting in inhibition of the expression of the corresponding endogenous messenger RNA.

Expression of the sense and antisense molecules can be accomplished by designing the expression cassette to comprise both a sense sequence and an antisense sequence. Alternatively, separate expression cassettes may be used for the sense and antisense sequences. Multiple plant lines transformed with the dsRNA interference expression cassette or expression cassettes are then screened to identify plant lines that show the greatest inhibition of MPG1 polypeptide expression. Methods for using dsRNA interference to inhibit the expression of endogenous plant genes are described in Waterhouse, et al., (1998) *Proc. Natl. Acad. Sci. USA* 95:13959-13964, Liu, et al., (2002) *Plant Physiol.* 129:1732-1743, and WO 99/49029, WO 99/53050, WO 99/61631, and WO 00/49035; each of which is herein incorporated by reference.

iv. Hairpin RNA Interference and Intron-Containing Hairpin RNA Interference

In some embodiments of the invention, inhibition of the expression of an MPG1 polypeptide may be obtained by hairpin RNA (hpRNA) interference or intron-containing hairpin RNA (ihpRNA) interference. These methods are highly efficient at inhibiting the expression of endogenous genes. See, Waterhouse and Helliwell, (2003) *Nat. Rev. Genet.* 4:29-38 and the references cited therein.

For hpRNA interference, the expression cassette is designed to express an RNA molecule that hybridizes with itself to form a hairpin structure that comprises a single-stranded loop region and a base-paired stem. The base-paired stem region comprises a sense sequence corresponding to all or part of the endogenous messenger RNA encoding the gene whose expression is to be inhibited, and an antisense sequence that is fully or partially complementary to the sense sequence. Alternatively, the base-paired stem region may correspond to a portion of a promoter sequence controlling expression of the gene to be inhibited. Thus, the base-paired stem region of the molecule generally determines the specificity of the RNA interference. hpRNA molecules are highly efficient at inhibiting the expression of endogenous genes, and the RNA interference they induce is inherited by subsequent generations of plants. See, for example, Chuang and Meyerowitz, (2000) Proc. Natl. Acad. Sci. USA 97:4985-4990; Stoutjesdijk, et al., (2002) *Plant Physiol.* 129:1723-1731; and Waterhouse and Helliwell, (2003) *Nat. Rev. Genet.* 4:29-38. Methods for using hpRNA interference to inhibit or silence the expression of genes are described, for example, in Chuang and Meyerowitz, (2000) *Proc. Natl. Acad. Sci. USA* 97:4985-4990; Stoutjesdijk, et al., (2002) *Plant Physiol.* 129:1723-1731; Waterhouse and Helliwell, (2003) *Nat. Rev. Genet.* 4:29-38; Pandolfini et al., *BMC Biotechnology* 3:7, and U.S. Patent Publication No. 2003/0175965; each of which is herein incorporated by reference. A transient assay for the efficiency of hpRNA constructs to silence gene expression in vivo has been described by Panstruga, et al., (2003) *Mol. Biol. Rep.* 30:135-140, herein incorporated by reference.

For ihpRNA, the interfering molecules have the same general structure as for hpRNA, but the RNA molecule additionally comprises an intron that is capable of being spliced in the cell in which the ihpRNA is expressed. The use of an intron minimizes the size of the loop in the hairpin RNA molecule following splicing, and this increases the efficiency of interference. See, for example, Smith, et al., (2000) *Nature* 407:319-320. In fact, Smith, et al., show 100% suppression of endogenous gene expression using ihpRNA-mediated interference. Methods for using ihpRNA interference to inhibit the expression of endogenous plant genes are described, for example, in Smith, et al., (2000) *Nature* 407:319-320; Wesley, et al., (2001) *Plant* 27:581-590; Wang and Waterhouse, (2001) *Curr. Opin. Plant Biol.* 5:146-150; Waterhouse and Helliwell, (2003) *Nat. Rev. Genet.* 4:29-38; Helliwell and Waterhouse, (2003) *Methods* 30:289-295, and U.S. Patent Publication No. 2003/0180945, each of which is herein incorporated by reference.

The expression cassette for hpRNA interference may also be designed such that the sense sequence and the antisense sequence do not correspond to an endogenous RNA. In this embodiment, the sense and antisense sequence flank a loop sequence that comprises a nucleotide sequence corresponding to all or part of the endogenous messenger RNA of the target gene. Thus, it is the loop region that determines the specificity of the RNA interference. See, for example, WO 02/00904; Mette, et al., (2000) *EMBO J* 19:5194-5201; Matzke, et al., (2001) *Curr. Opin. Genet. Devel.* 11:221-227; Scheid, et al., (2002) *Proc. Natl. Acad. Sci., USA* 99:13659-13662; Aufsaftz, et al., (2002) *Proc. Nat'l. Acad. Sci.* 99(4):16499-16506; Sijen, et al., *Curr. Biol.* (2001) 11:436-440), herein incorporated by reference.

v. Amplicon Mediated Interference

Amplicon expression cassettes comprise a plant virus-derived sequence that contains all or part of the target gene but generally not all of the genes of the native virus. The viral sequences present in the transcription product of the expression cassette allow the transcription product to direct its own replication. The transcripts produced by the amplicon may be either sense or antisense relative to the target sequence (i.e., the messenger RNA for the MPG1 polypeptide). Methods of using amplicons to inhibit the expression of endogenous plant genes are described, for example, in Angell and Baulcombe, (1997) *EMBO J.* 16:3675-3684, Angell and Baulcombe, (1999) *Plant J.* 20:357-362, and U.S. Pat. No. 6,635,805, each of which is herein incorporated by reference.

vi. Ribozymes

In some embodiments, the polynucleotide expressed by the expression cassette of the invention is catalytic RNA or has ribozyme activity specific for the messenger RNA of the MPG1 polypeptide. Thus, the polynucleotide causes the degradation of the endogenous messenger RNA, resulting in reduced expression of the MPG1 polypeptide. This method is described, for example, in U.S. Pat. No. 4,987,071, herein incorporated by reference.

vii. Small Interfering RNA or Micro RNA

In some embodiments of the invention, inhibition of the expression of MPG1 polypeptide may be obtained by RNA interference by expression of a gene encoding a micro RNA (miRNA). miRNAs are regulatory agents consisting of about 22 ribonucleotides. miRNA are highly efficient at inhibiting the expression of endogenous genes. See, for example Javier, et al., (2003) *Nature* 425:257-263, herein incorporated by reference.

For miRNA interference, the expression cassette is designed to express an RNA molecule that is modeled on an endogenous miRNA gene. The miRNA gene encodes an RNA that forms a hairpin structure containing a 22-nucleotide sequence that is complementary to another endogenous gene (target sequence). For suppression of MPG1 expression, the 22-nucleotide sequence is selected from an MPG1 transcript sequence and contains 22 nucleotides of said MPG1 sequence in sense orientation and 21 nucleotides of a corresponding antisense sequence that is complementary to the sense sequence. miRNA molecules are highly efficient at inhibiting the expression of endogenous genes, and the RNA interference they induce is inherited by subsequent generations of plants.

2. Polypeptide-Based Inhibition of Gene Expression

In one embodiment, the polynucleotide encodes a zinc finger protein that binds to a gene encoding an MPG1 polypeptide, resulting in reduced expression of the gene. In particular embodiments, the zinc finger protein binds to a regulatory region of an MPG1 gene. In other embodiments, the zinc finger protein binds to a messenger RNA encoding an MPG1 polypeptide and prevents its translation. Methods of selecting sites for targeting by zinc finger proteins have been described, for example, in U.S. Pat. No. 6,453,242, and methods for using zinc finger proteins to inhibit the expression of genes in plants are described, for example, in U.S. Patent Publication No. 2003/0037355; each of which is herein incorporated by reference.

3. Polypeptide-Based Inhibition of Protein Activity

In some embodiments of the invention, the polynucleotide encodes an antibody that binds to at least one MPG1 polypeptide, and reduces the activity of the MPG1 polypeptide. In another embodiment, the binding of the antibody results in increased turnover of the antibody—MPG1 complex by cellular quality control mechanisms. The expression of antibodies in plant cells and the inhibition of molecular pathways by expression and binding of antibodies to proteins in plant cells are well known in the art. See, for example, Conrad and Sonnewald, (2003) *Nature Biotech.* 21:35-36, incorporated herein by reference.

4. Gene Disruption

In some embodiments of the present invention, the activity of an MPG1 polypeptide may be reduced or eliminated by disrupting the gene encoding the MPG1 polypeptide. The gene encoding the MPG1 polypeptide may be disrupted by any method known in the art. For example, in one embodiment, the gene is disrupted by transposon tagging. In another embodiment, the gene is disrupted by mutagenizing plants using random or targeted mutagenesis, and selecting for plants that have desired traits.

i. Transposon Tagging

In one embodiment of the invention, transposon tagging is used to reduce or eliminate the MPG1 activity of one or more MPG1 polypeptides. Transposon tagging comprises inserting a transposon within an endogenous MPG1 gene to reduce or eliminate expression of the MPG1 polypeptide. "MPG1 gene" is intended to mean the gene that encodes an MPG1 polypeptide.

In this embodiment, the expression of one or more MPG1 polypeptides is reduced or eliminated by inserting a transposon within a regulatory region or coding region of the gene encoding the MPG1 polypeptide. A transposon that is within an exon, intron, 5' or 3' untranslated sequence, a promoter, or any other regulatory sequence of an MPG1 gene may be used to reduce or eliminate the expression and/or activity of the encoded MPG1 polypeptide.

Methods for the transposon tagging of specific genes in plants are well known in the art. See, for example, Maes, et al., (1999) *Trends Plant Sci.* 4:90-96; Dharmapuri and Sonti, (1999) *FEMS Microbiol. Lett.* 179:53-59; Meissner, et al., (2000) *Plant J.* 22:265-274; Phogat, et al., (2000) *J Biosci.* 25:57-63; Walbot, (2000) *Curr. Opin. Plant Biol.* 2:103-107; Gai, et al., (2000) *Nucleic Acids Res.* 28:94-96; Fitzmaurice, et al., (1999) *Genetics* 153:1919-1928). In addition, the TUSC process for selecting Mu insertions in selected genes has been described in Bensen, et al., (1995) *Plant Cell* 7:75-84; Mena, et al., (1996) *Science* 274:1537-1540; and U.S. Pat. No. 5,962,764; each of which is herein incorporated by reference.

ii. Mutant Plants with Reduced Activity

Additional methods for decreasing or eliminating the expression of endogenous genes in plants are also known in the art and can be similarly applied to the instant invention. These methods include other forms of mutagenesis, such as ethyl methanesulfonate-induced mutagenesis, deletion mutagenesis, and fast neutron deletion mutagenesis used in a reverse genetics sense (with PCR) to identify plant lines in which the endogenous gene has been deleted. For examples of these methods see, Ohshima, et al., (1998) *Virology* 243:472-481; Okubara, et al., (1994) *Genetics* 137:867-874; and Quesada, et al., (2000) *Genetics* 154:421-436; each of which is herein incorporated by reference. In addition, a fast and automatable method for screening for chemically induced mutations, TILLING (Targeting Induced Local Lesions In Genomes), using denaturing HPLC or selective endonuclease digestion of selected PCR products is also applicable to the instant invention. See, McCallum, et al., (2000) *Nat. Biotechnol.* 18:455-457, herein incorporated by reference.

Mutations that impact gene expression or that interfere with the function of the encoded protein are well known in the art. Insertional mutations in gene exons usually result in null-mutants. Mutations in conserved residues are particularly effective in inhibiting the activity of the encoded protein. Conserved residues of plant MPG1 polypeptides suitable for mutagenesis with the goal to eliminate MPG1 activity have been described. Such mutants can be isolated according to well-known procedures, and mutations in different MPG1 loci can be stacked by genetic crossing. See, for example, Gruis, et al., (2002) *Plant Cell* 14:2863-2882.

In another embodiment of this invention, dominant mutants can be used to trigger RNA silencing due to gene inversion and recombination of a duplicated gene locus. See, for example, Kusaba, et al., (2003) *Plant Cell* 15:1455-1467.

The invention encompasses additional methods for reducing or eliminating the activity of one or more MPG1 polypeptides. Examples of other methods for altering or mutating a genomic nucleotide sequence in a plant are known in the art and include, but are not limited to, the use of RNA:DNA vectors, RNA:DNA mutational vectors, RNA:DNA repair vectors, mixed-duplex oligonucleotides, self-complementary RNA:DNA oligonucleotides, and recombinogenic oligonucleobases. Such vectors and methods of use are known in the art. See, for example, U.S. Pat. Nos. 5,565,350; 5,731,181; 5,756,325; 5,760,012; 5,795,972; and 5,871,984; each of which are herein incorporated by reference. See also, WO 98/49350, WO 99/07865, WO 99/25821, and Beetham, et al., (1999) *Proc. Natl. Acad. Sci. USA* 96:8774-8778; each of which is herein incorporated by reference.

The methods of the invention provides for improved plant performance such as stress tolerance, biomass accumulation or grain yield. This performance may be demonstrated in a number of ways including the following.

Method of Use for MPG1 polynucleotide, Expression Cassettes, and Additional Polynucleotides The nucleotides, expression cassettes and methods disclosed herein are useful in regulating expression of any heterologous nucleotide sequence in a host plant in order to vary the phenotype of a plant. Various changes in phenotype are of interest including modifying the fatty acid composition in a plant, altering the amino acid content of a plant, altering a plant's pathogen defense mechanism, and the like. These results can be achieved by providing expression of heterologous products or increased expression of endogenous products in plants. Alternatively, the results can be achieved by providing for a reduction of expression of one or more endogenous products, particularly enzymes or cofactors in the plant. These changes result in a change in phenotype of the transformed plant.

Genes of interest are reflective of the commercial markets and interests of those involved in the development of the crop. Crops and markets of interest change, and as developing nations open up world markets, new crops and technologies will emerge also. In addition, as our understanding of agronomic traits and characteristics such as yield and heterosis increase, the choice of genes for transformation will change accordingly. General categories of genes of interest include, for example, those genes involved in information, such as zinc fingers, those involved in communication, such as kinases, and those involved in housekeeping, such as heat shock proteins. More specific categories of transgenes, for example, include genes encoding important traits for agronomics, insect resistance, disease resistance, herbicide resistance, sterility, grain characteristics, and commercial products. Genes of interest include, generally, those involved in oil, starch, carbohydrate, or nutrient metabolism as well as those affecting kernel size, sucrose loading, and the like.

In certain embodiments the nucleic acid sequences of the present invention can be used in combination ("stacked") with other polynucleotide sequences of interest in order to create plants with a desired phenotype. The combinations generated can include multiple copies of any one or more of the polynucleotides of interest. The polynucleotides of the present invention may be stacked with any gene or combination of genes to produce plants with a variety of desired trait combinations, including but not limited to traits desirable for animal feed such as high oil genes (e.g., U.S. Pat. No. 6,232,529); balanced amino acids (e.g., hordothionins (U.S. Pat. Nos. 5,990,389; 5,885,801; 5,885,802; and 5,703, 049); barley high lysine (Williamson, et al., (1987) *Eur. J. Biochem.* 165:99-106; and WO 98/20122); and high methionine proteins (Pedersen, et al., (1986) *J. Biol. Chem.* 261: 6279; Kirihara, et al., (1988) *Gene* 71:359; and Musumura, et al., (1989) *Plant Mol. Biol.* 12:123)); increased digestibility (e.g., modified storage proteins (U.S. application Ser. No. 10/053,410, filed Nov. 7, 2001); and thioredoxins (U.S. application Ser. No. 10/005,429, filed Dec. 3, 2001)), the disclosures of which are herein incorporated by reference. The polynucleotides of the present invention can also be stacked with traits desirable for insect, disease or herbicide resistance (e.g., *Bacillus thuringiensis* toxic proteins (U.S. Pat. Nos. 5,366,892; 5,747,450; 5,736,514; 5,723,756; 5,593,881; Geiser, et al., (1986) *Gene* 48:109); lectins (Van Damme, et al., (1994) *Plant Mol. Biol.* 24:825); fumonisin detoxification genes (U.S. Pat. No. 5,792,931); avirulence and disease resistance genes (Jones, et al., (1994) *Science* 266:789; Martin, et al., (1993) *Science* 262:1432; Mindrinos, et al., (1994) *Cell* 78:1089); acetolactate synthase (ALS) mutants that lead to herbicide resistance such as the S4 and/or Hra mutations; inhibitors of glutamine synthase such as phosphinothricin or basta (e.g., bar gene); and glyphosate resistance (EPSPS gene)); and traits desirable for processing or process products such as high oil (e.g., U.S. Pat. No. 6,232,529); modified oils (e.g., fatty acid desaturase genes (U.S. Pat. No. 5,952,544; WO 94/11516)); modified starches (e.g., ADPG pyrophosphorylases (AGPase), starch synthases (SS), starch branching enzymes (SBE) and starch debranching enzymes (SDBE)); and polymers or bioplastics (e.g., U.S. Pat. No. 5,602,321; beta-ketothiolase, polyhydroxybutyrate synthase, and acetoacetyl-CoA reductase (Schubert, et al., (1988) *J Bacteriol.* 170:5837-5847) facilitate expression of polyhydroxyalkanoates (PHAs)), the disclosures of which are herein incorporated by reference. One could also combine the polynucleotides of the present invention with polynucleotides affecting agronomic traits such as male sterility (e.g., see U.S. Pat. No. 5,583,210), stalk strength, flowering time, or transformation technology traits such as cell cycle regulation or gene targeting (e.g., WO 99/61619; WO 00/17364; WO 99/25821), the disclosures of which are herein incorporated by reference.

In one embodiment, sequences of interest improve plant growth and/or crop yields. For example, sequences of interest include agronomically important genes that result in improved primary or lateral root systems. Such genes include, but are not limited to, nutrient/water transporters and growth induces. Examples of such genes, include but are not limited to, maize plasma membrane $H^+$-ATPase (MHA2) (Frias, et al., (1996) *Plant Cell* 8:1533-44); AKT1, a component of the potassium uptake apparatus in *Arabidopsis,* (Spalding, et al., (1999) *J. Gen Physiol* 113:909-18); RML genes which activate cell division cycle in the root apical cells (Cheng, et al., (1995) *Plant Physiol* 108:881); maize glutamine synthetase genes (Sukanya, et al., (1994) *Plant Mol Biol* 26:1935-46) and hemoglobin (Duff, et al., (1997) *J. Biol. Chem* 27:16749-16752, Arredondo-Peter, et al., (1997) *Plant Physiol.* 115:1259-1266; Arredondo-Peter, et al., (1997) *Plant Physiol* 114:493-500 and references sited therein). The sequence of interest may also be useful in expressing antisense nucleotide sequences of genes that that negatively affects root development.

Additional, agronomically important traits such as oil, starch, and protein content can be genetically altered in addition to using traditional breeding methods. Modifications include increasing content of oleic acid, saturated and unsaturated oils, increasing levels of lysine and sulfur, providing essential amino acids, and also modification of starch. Hordothionin protein modifications are described in U.S. Pat. Nos. 5,703,049, 5,885,801, 5,885,802, and 5,990, 389, herein incorporated by reference. Another example is lysine and/or sulfur rich seed protein encoded by the soybean 2S albumin described in U.S. Pat. No. 5,850,016, and the chymotrypsin inhibitor from barley, described in Williamson, et al., (1987) *Eur. J. Biochem.* 165:99-106, the disclosures of which are herein incorporated by reference.

Derivatives of the coding sequences can be made by site-directed mutagenesis to increase the level of preselected amino acids in the encoded polypeptide. For example, the gene encoding the barley high lysine polypeptide (BHL) is derived from barley chymotrypsin inhibitor, U.S. application Ser. No. 08/740,682, filed Nov. 1, 1996, and WO 98/20133, the disclosures of which are herein incorporated by reference. Other proteins include methionine-rich plant proteins such as from sunflower seed (Lilley, et al., (1989) *Proceedings of the World Congress on Vegetable Protein Utilization in Human Foods and Animal Feedstuffs*, ed. Applewhite (American Oil Chemists Society, Champaign, Ill.), pp. 497-502; herein incorporated by reference); corn (Pedersen, et al., (1986) *J. Biol. Chem.* 261:6279; Kirihara, et al., (1988) *Gene* 71:359; both of which are herein incorporated by reference); and rice (Musumura, et al., (1989) *Plant Mol. Biol.* 12:123, herein incorporated by reference). Other agronomically important genes encode latex, Floury 2, growth factors, seed storage factors, and transcription factors. Insect resistance genes may encode resistance to pests that have great yield drag such as rootworm, cutworm, European Corn Borer, and the like. Such genes include, for example, *Bacillus thuringiensis* toxic protein genes (U.S. Pat. Nos. 5,366,892; 5,747,450; 5,736,514; 5,723,756; 5,593,881; and Geiser, et al., (1986) *Gene* 48:109); and the like.

Genes encoding disease resistance traits include detoxification genes, such as against fumonosin (U.S. Pat. No. 5,792,931); avirulence (avr) and disease resistance (R) genes (Jones, et al., (1994) *Science* 266:789; Martin, et al., (1993) *Science* 262:1432; and Mindrinos, et al., (1994) *Cell* 78:1089); and the like.

Herbicide resistance traits may include genes coding for resistance to herbicides that act to inhibit the action of acetolactate synthase (ALS), in particular the sulfonylurea-type herbicides (e.g., the acetolactate synthase (ALS) gene containing mutations leading to such resistance, in particular the S4 and/or Hra mutations), genes coding for resistance to herbicides that act to inhibit action of glutamine synthase, such as phosphinothricin or basta (e.g., the bar gene), or other such genes known in the art. The bar gene encodes resistance to the herbicide basta, the nptII gene encodes resistance to the antibiotics kanamycin and geneticin, and the ALS-gene mutants encode resistance to the herbicide chlorsulfuron.

Sterility genes can also be encoded in an expression cassette and provide an alternative to physical detasseling. Examples of genes used in such ways include male tissue-preferred genes and genes with male sterility phenotypes such as QM, described in U.S. Pat. No. 5,583,210. Other genes include kinases and those encoding compounds toxic to either male or female gametophytic development.

The quality of grain is reflected in traits such as levels and types of oils, saturated and unsaturated, quality and quantity of essential amino acids, and levels of cellulose. In corn, modified hordothionin proteins are described in U.S. Pat. Nos. 5,703,049, 5,885,801, 5,885,802, and 5,990,389.

Commercial traits can also be encoded on a gene or genes that could increase for example, starch for ethanol production, or provide expression of proteins. Another important commercial use of transformed plants is the production of polymers and bioplastics such as described in U.S. Pat. No. 5,602,321. Genes such as β-Ketothiolase, PHBase (polyhydroxyburyrate synthase), and acetoacetyl-CoA reductase (see, Schubert, et al., (1988) *J Bacteriol.* 170:5837-5847) facilitate expression of polyhyroxyalkanoates (PHAs).

Exogenous products include plant enzymes and products as well as those from other sources including prokaryotes and other eukaryotes. Such products include enzymes, cofactors, hormones, and the like. The level of proteins, particularly modified proteins having improved amino acid distribution to improve the nutrient value of the plant, can be increased. This is achieved by the expression of such proteins having enhanced amino acid content.

Genome Editing and Induced Mutagenesis

In general, methods to modify or alter the host endogenous genomic DNA are available. This includes altering the host native DNA sequence or a pre-existing transgenic sequence including regulatory elements, coding and non-coding sequences. These methods are also useful in targeting nucleic acids to pre-engineered target recognition sequences in the genome. As an example, the genetically modified cell or plant described herein is generated using "custom" meganucleases produced to modify plant genomes (see, e.g., WO 2009/114321; Gao, et al., (2010) Plant Journal 1:176-187). Other site-directed engineering is through the use of zinc finger domain recognition coupled with the restriction properties of restriction enzyme. See, e.g., Urnov, et al., (2010) Nat Rev Genet. 11(9):636-46; Shukla, et al., (2009) Nature 459(7245):437-41.

"TILLING" or "Targeting Induced Local Lesions IN Genomics" refers to a mutagenesis technology useful to generate and/or identify and to eventually isolate mutagenised variants of a particular nucleic acid with modulated expression and/or activity (McCallum, et al., (2000), Plant Physiology 123:439-442; McCallum, et al., (2000) Nature Biotechnology 18:455-457 and Colbert, et al., (2001) Plant Physiology 126:480-484).

TILLING combines high density point mutations with rapid sensitive detection of the mutations. Typically, ethylmethanesulfonate (EMS) is used to mutagenize plant seed. EMS alkylates guanine, which typically leads to mispairing. For example, seeds are soaked in an about 10-20 mM solution of EMS for about 10 to 20 hours; the seeds are washed and then sown. The plants of this generation are known as M1. M1 plants are then self-fertilized. Mutations that are present in cells that form the reproductive tissues are inherited by the next generation (M2). Typically, M2 plants are screened for mutation in the desired gene and/or for specific phenotypes.

TILLING also allows selection of plants carrying mutant variants. These mutant variants may exhibit modified expression, either in strength or in location or in timing (if the mutations affect the promoter, for example). These mutant variants may exhibit higher or lower activity than that exhibited by the gene in its natural form. TILLING combines high-density mutagenesis with high-throughput screening methods. The steps typically followed in TILLING are: (a) EMS mutagenesis (Redei and Koncz, (1992) In Methods in *Arabidopsis* Research, Koncz, et al., eds. Singapore, World Scientific Publishing Co, pp. 16-82; Feldmann, et al., (1994) In *Arabidopsis*. Meyerowitz and Somerville, eds, Cold Spring Harbor Laboratory Press, Cold Spring Harbor, N.Y., pp 137-172; Lightner and Caspar, (1998) In Methods on Molecular Biology 82:91-104; Martinez-Zapater and Salinas, eds, Humana Press, Totowa, N.J.); (b) DNA preparation and pooling of individuals; (c) PCR amplification of a region of interest; (d) denaturation and annealing to allow formation of heteroduplexes; (e) DHPLC, where the presence of a heteroduplex in a pool is detected as an extra peak in the chromatogram; (f) identification of the mutant individual; and (g) sequencing of the mutant PCR product. Methods for TILLING are well known in the art (U.S. Pat. No. 8,071,840).

Other mutagenic methods can also be employed to introduce mutations in a disclosed gene. Methods for introducing genetic mutations into plant genes and selecting plants with desired traits are well known. For instance, seeds or other plant material can be treated with a mutagenic chemical substance, according to standard techniques. Such chemical substances include, but are not limited to, the following: diethyl sulfate, ethylene imine, and N-nitroso-N-ethylurea. Alternatively, ionizing radiation from sources such as X-rays or gamma rays can be used.

Embodiments of the disclosure reflect the determination that the genotype of an organism can be modified to contain dominant suppressor alleles or transgene constructs that suppress (i.e., reduce, but not ablate) the activity of a gene, wherein the phenotype of the organism is not substantially affected.

Hybrid seed production requires elimination or inactivation of pollen produced by the female parent. Incomplete removal or inactivation of the pollen provides the potential for selfing, raising the risk that inadvertently self-pollinated seed will unintentionally be harvested and packaged with hybrid seed. Once the seed is planted, the selfed plants can be identified and selected; the selfed plants are genetically equivalent to the female inbred line used to produce the hybrid. Typically, the selfed plants are identified and selected based on their decreased vigor relative to the hybrid plants. For example, female selfed plants of e are identified by their less vigorous appearance for vegetative and/or reproductive characteristics, including shorter plant height, small ear size, ear and kernel shape, cob color or other characteristics. Selfed lines also can be identified using molecular marker analyses (see, e.g., Smith and Wych, (1995) Seed Sci. Technol. 14:1-8). Using such methods, the homozygosity of the self-pollinated line can be verified by analyzing allelic composition at various loci in the genome.

Because hybrid plants are important and valuable field crops, plant breeders are continually working to develop high-yielding hybrids that are agronomically sound based on stable inbred lines. The availability of such hybrids allows a maximum amount of crop to be produced with the inputs used, while minimizing susceptibility to pests and environmental stresses. To accomplish this goal, the plant breeder must develop superior inbred parental lines for producing hybrids by identifying and selecting genetically unique individuals that occur in a segregating population. The present disclosure contributes to this goal, for example by providing plants that, when crossed, generate male sterile progeny, which can be used as female parental plants for generating hybrid plants.

A large number of genes have been identified as being tassel preferred in their expression pattern using traditional methods and more recent high-throughput methods. The correlation of function of these genes with important biochemical or developmental processes that ultimately lead to functional pollen is arduous when approaches are limited to classical forward or reverse genetic mutational analysis. As disclosed herein, suppression approaches provide an alternative rapid means to identify genes that are directly related to pollen development.

Promoters useful for expressing a nucleic acid molecule of interest can be any of a range of naturally-occurring promoters known to be operative in plants or animals, as desired. Promoters that direct expression in cells of male or female reproductive organs of a plant are useful for generating a transgenic plant or breeding pair of plants of the disclosure. The promoters useful in the present disclosure can include constitutive promoters, which generally are active in most or all tissues of a plant; inducible promoters, which generally are inactive or exhibit a low basal level of expression and can be induced to a relatively high activity upon contact of cells with an appropriate inducing agent; tissue-specific (or tissue-preferred) promoters, which generally are expressed in only one or a few particular cell types (e.g., plant anther cells) and developmental- or stage-specific promoters, which are active only during a defined period during the growth or development of a plant. Often promoters can be modified, if necessary, to vary the expression level. Certain embodiments comprise promoters exogenous to the species being manipulated. For example, the Ms45 gene introduced into ms45ms45 maize germplasm may be driven by a promoter isolated from another plant species; a hairpin construct may then be designed to target the exogenous plant promoter, reducing the possibility of hairpin interaction with non-target, endogenous promoters.

Exemplary constitutive promoters include the 35S cauliflower mosaic virus (CaMV) promoter promoter (Odell, et al., (1985) Nature 313:810-812), the maize ubiquitin promoter (Christensen, et al., (1989) Plant Mol. Biol. 12:619-632 and Christensen, et al., (1992) Plant Mol. Biol. 18:675-689); the core promoter of the Rsyn7 promoter and other constitutive promoters disclosed in WO 1999/43838 and U.S. Pat. No. 6,072,050; rice actin (McElroy, et al., (1990) Plant Cell 2:163-171); pEMU (Last, et al., (1991) Theor. Appl. Genet. 81:581-588); MAS (Velten, et al., (1984) EMBO J. 3:2723-2730); ALS promoter (U.S. Pat. No. 5,659,026); rice actin promoter (U.S. Pat. No. 5,641,876; WO 2000/70067), maize histone promoter (Brignon, et al., (1993) Plant Mol Bio 22(6):1007-1015; Rasco-Gaunt, et al., (2003) Plant Cell Rep. 21(6):569-576) and the like. Other constitutive promoters include, for example, those described in U.S. Pat. Nos. 5,608,144 and 6,177,611 and PCT Publication Number WO 2003/102198.

Tissue-specific, tissue-preferred or stage-specific regulatory elements further include, for example, the AGL8/FRUITFULL regulatory element, which is activated upon floral induction (Hempel, et al., (1997) Development 124: 3845-3853); root-specific regulatory elements such as the regulatory elements from the RCP1 gene and the LRP1 gene (Tsugeki and Fedoroff, (1999) Proc. Natl. Acad., USA 96:12941-12946; Smith and Fedoroff, (1995) Plant Cell 7:735-745); flower-specific regulatory elements such as the regulatory elements from the LEAFY gene and the APETALA1 gene (Blazquez, et al., (1997) Development 124:3835-3844; Hempel, et al., supra, 1997); seed-specific regulatory elements such as the regulatory element from the oleosin gene (Plant, et al., (1994) Plant Mol. Biol. 25:193-205) and dehiscence zone specific regulatory element. Additional tissue-specific or stage-specific regulatory elements include the Zn13 promoter, which is a pollen-specific promoter (Hamilton, et al., (1992) Plant Mol. Biol. 18:211-218); the UNUSUAL FLORAL ORGANS (UFO) promoter, which is active in apical shoot meristem; the promoter active in shoot meristems (Atanassova, et al., (1992) Plant J. 2:291), the cdc2 promoter and cyc07 promoter (see, for example, Ito, et al., (1994) Plant Mol. Biol. 24:863-878; Martinez, et al., (1992) Proc. Natl. Acad. Sci., USA 89:7360); the meristematic-preferred meri-5 and H3 promoters (Medford, et al., (1991) Plant Cell 3:359; Terada, et al., (1993) Plant J. 3:241); meristematic and phloem-preferred promoters of Myb-related genes in barley (Wissenbach, et al., (1993) Plant J. 4:411); *Arabidopsis* cyc3aAt and cyc1At (Shaul, et al., (1996) Proc. Natl. Acad. Sci. 93:4868-4872); *C. roseus* cyclins CYS and CYM (Ito, et al., (1997) Plant J. 11:983-992); and Nicotiana CyclinB1 (Trehin, et al., (1997) Plant Mol. Biol. 35:667-672); the promoter of the APETALA3 gene, which is active in floral meristems (Jack, et al., (1994) Cell 76:703; Hempel, et al., supra, 1997); a promoter of an agamous-like (AGL) family member, for example, AGL8, which is active in shoot meristem upon the transition to flowering (Hempel, et al., supra, 1997); floral abscission zone promoters; L1-specific promoters; the ripening-enhanced tomato polygalacturonase promoter (Nicholass, et al., (1995) Plant Mol. Biol. 28:423-435), the E8 promoter (Deikman, et al., (1992) Plant Physiol. 100:2013-2017) and the fruit-specific 2A1 promoter, U2 and U5 snRNA promoters from maize, the Z4 promoter from a gene encoding the Z4 22 kD zein protein, the Z10 promoter from a gene encoding a 10 kD zein protein, a Z27 promoter from a gene encoding a 27 kD zein protein, the A20 promoter from the gene encoding a 19 kD zein protein, and the like. Additional tissue-specific promoters can be isolated using well known methods (see, e.g., U.S. Pat. No. 5,589,379).

Shoot-if) preferred promoters include shoot meristem-preferred promoters such as promoters disclosed in Weigel, et al., (1992) Cell 69:843-859.

Use in Breeding Methods

The transformed plants of the disclosure may be used in a plant breeding program. The goal of plant breeding is to combine, in a single variety or hybrid, various desirable traits. For field crops, these traits may include, for example, resistance to diseases and insects, tolerance to heat and drought, tolerance to chilling or freezing, reduced time to crop maturity, greater yield and better agronomic quality. With mechanical harvesting of many crops, uniformity of plant characteristics such as germination and stand establishment, growth rate, maturity and plant and ear height is desirable. Traditional plant breeding is an important tool in developing new and improved commercial crops. This disclosure encompasses methods for producing a plant by crossing a first parent plant with a second parent plant wherein one or both of the parent plants is a transformed plant displaying a phenotype as described herein.

Plant breeding techniques known in the art and used in a plant breeding program include, but are not limited to, recurrent selection, bulk selection, mass selection, backcrossing, pedigree breeding, open pollination breeding, restriction fragment length polymorphism enhanced selection, genetic marker enhanced selection, doubled haploids and transformation. Often combinations of these techniques are used.

The development of hybrids in a plant breeding program requires, in general, the development of homozygous inbred lines, the crossing of these lines and the evaluation of the crosses. There are many analytical methods available to evaluate the result of a cross. The oldest and most traditional method of analysis is the observation of phenotypic traits. Alternatively, the genotype of a plant can be examined.

A genetic trait which has been engineered into a particular plant using transformation techniques can be moved into another line using traditional breeding techniques that are well known in the plant breeding arts. For example, a backcrossing approach is commonly used to move a transgene from a transformed plant to an elite inbred line and the resulting progeny would then comprise the transgene(s). Also, if an inbred line was used for the transformation, then the transgenic plants could be crossed to a different inbred in order to produce a transgenic hybrid plant. As used herein, "crossing" can refer to a simple X by Y cross or the process of backcrossing, depending on the context.

The development of a hybrid in a plant breeding program involves three steps: (1) the selection of plants from various germplasm pools for initial breeding crosses; (2) the selfing of the selected plants from the breeding crosses for several generations to produce a series of inbred lines, which, while different from each other, breed true and are highly homozygous and (3) crossing the selected inbred lines with different inbred lines to produce the hybrids. During the inbreeding process, the vigor of the lines decreases. Vigor is restored when two different inbred lines are crossed to produce the hybrid. An important consequence of the homozygosity and homogeneity of the inbred lines is that the hybrid created by crossing a defined pair of inbreds will always be the same. Once the inbreds that give a superior hybrid have been identified, the hybrid seed can be reproduced indefinitely as long as the homogeneity of the inbred parents is maintained.

Transgenic plants of the present disclosure may be used to produce, e.g., a single cross hybrid, a three-way hybrid or a double cross hybrid. A single cross hybrid is produced when two inbred lines are crossed to produce the F1 progeny. A double cross hybrid is produced from four inbred lines crossed in pairs (A×B and C×D) and then the two F1 hybrids are crossed again (A×B) times (C×D). A three-way cross hybrid is produced from three inbred lines where two of the inbred lines are crossed (A×B) and then the resulting F1 hybrid is crossed with the third inbred (A×B)×C. Much of the hybrid vigor and uniformity exhibited by F1 hybrids is lost in the next generation (F2). Consequently, seed produced by hybrids is consumed rather than planted.

This invention can be better understood by reference to the following non-limiting examples. It will be appreciated by those skilled in the art that other embodiments of the invention may be practiced without departing from the spirit and the scope of the invention as herein disclosed and claimed.

EXAMPLES

Rice plants that overexpress MPG1 an AP2 like transcription factor exhibit significantly increased biomass and seed yield compared to wild-type plants, and this is especially true when grown under stressful conditions. This was derived through the analysis of a rice T-DNA insertion mutant possessing increased biomass and seed yield compared to wild-type plants. The presence of the T-DNA insertion was tracked across multiple generations, while recording biomass measurements to support the coloration of the insertion and the phenotype. Of the generations grown the mutant experienced as high as a 7.4-fold increase in biomass and a simultaneous 3.6-fold increase in seed yield compared to segregating wild-type plants. The insertion mutants also experience a delay in flowering time by an average of 16 days compared to wild-type plants, increasing their vegetative stage significantly which contributes to increased biomass. Insertion mutants also possess longer and wider leaves, and increased tiller girth compared to wild-type plants.

The insertion caused a mutagenic event that altered the expression and/or function of a nearby gene or genes. Further investigation via RT-PCR supported this claim, as the expression level of one of the neighboring genes is significantly up-regulated with the presence of the T-DNA insertion. This particular gene is a transcription factor belonging to a large superfamily of genes in plants. Further phenotypic investigation suggests that the degree of the phenotype (i.e. the increase in biomass) is influenced by abiotic and/or biotic stress. Plants placed under drought, pH, and salt stress are more successful in accumulating biomass, and producing seed with the over-expression of this particular transcription factor than wild type controls.

This transcription factor appears to have little to no expression in wild-type plants based on our preliminary analysis.

Example 1

Figure 2:
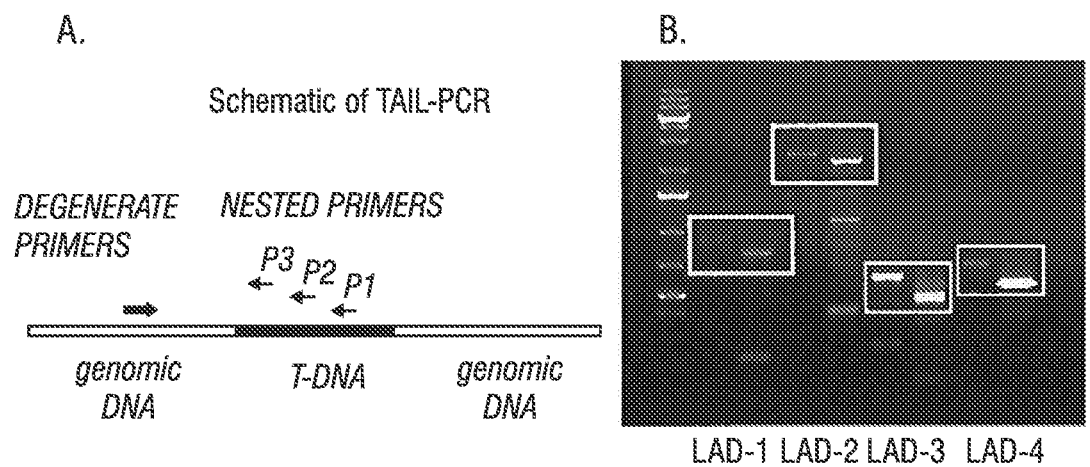
FIGS. 2A-2C represent how the TAIL-PCR is conducted. 2B is a gel-electrophoresis of the T-DNA insertion cassette within the mpg1 mutant and TAIL-PCR primer sets, (boxed regions represent amplicons of the T-DNA insertion and neighboring gDNA). 2C is a schematic of the gDNA location of the T-DNA.
Figure 2:
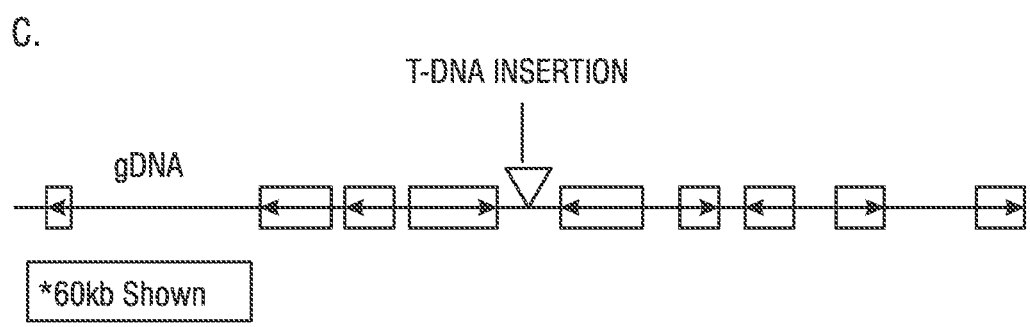
Figure 3:
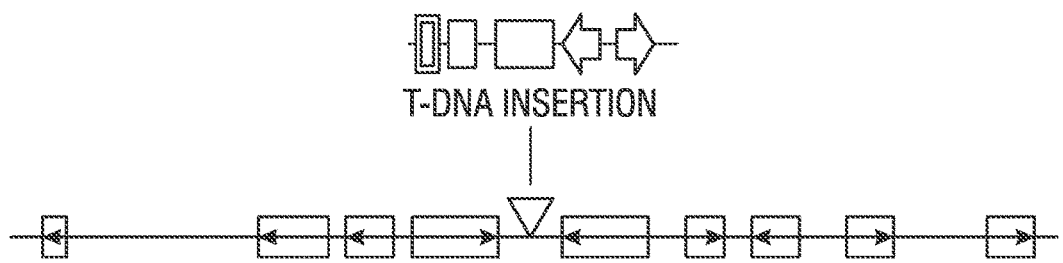
FIG. 3 shows the localization of the T-DNA insertion.
Figure 4:
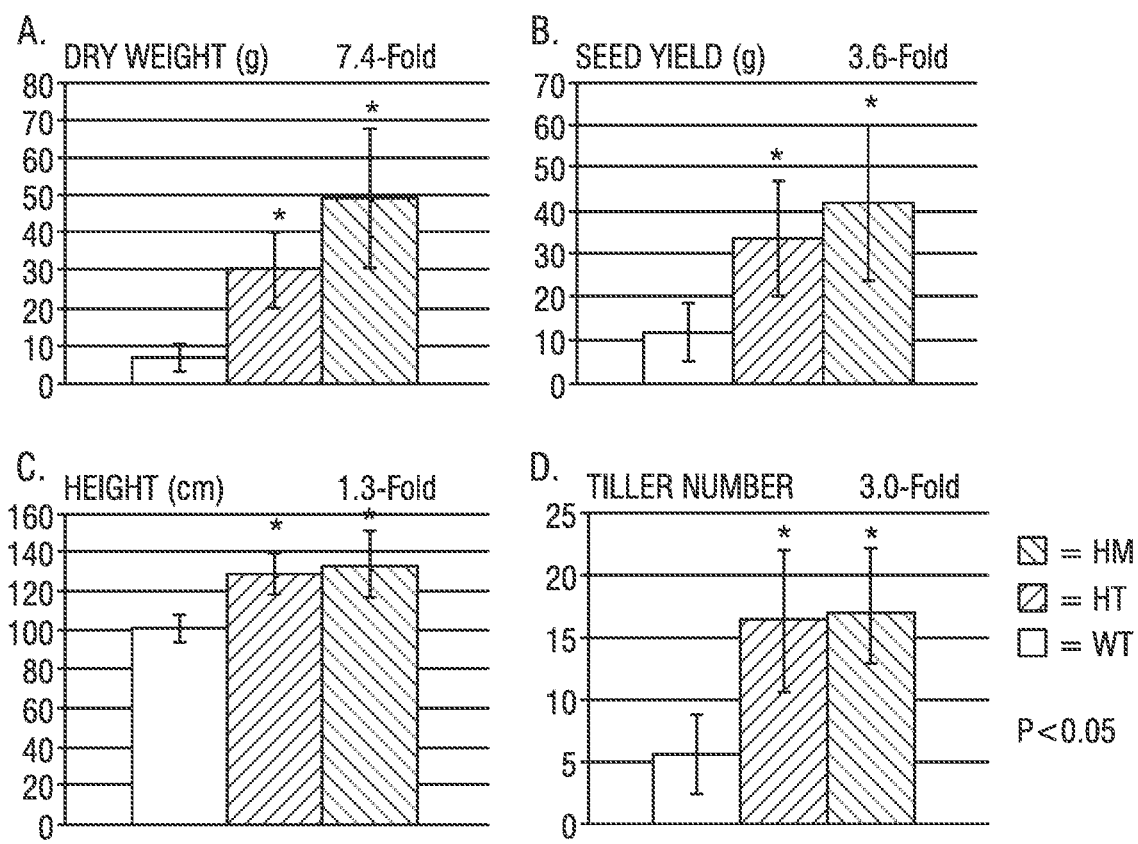
FIGS. 4A-4D are graphs showing dry weight, seed yield, plant height and tiller number for MPG1 and wildtype plants for the T2 generation.
Figure 5:
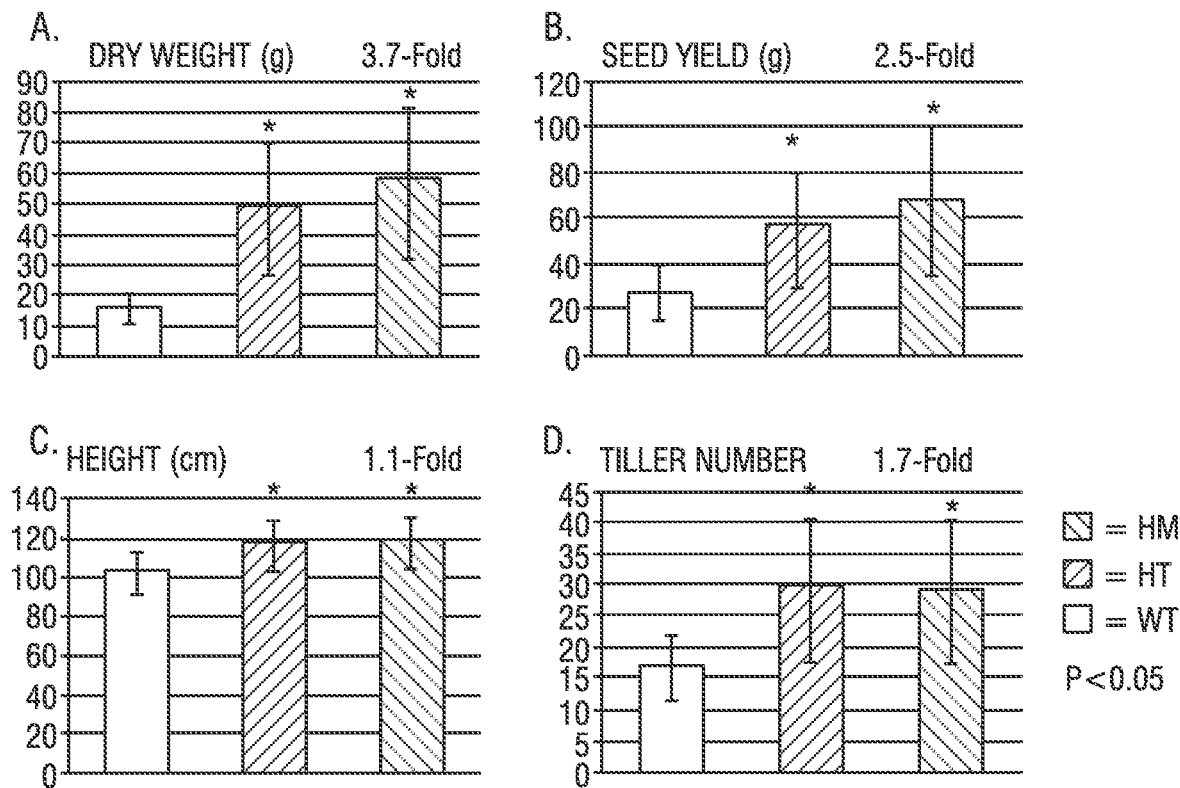
FIG. 5A-5D are graphs showing dry weight, seed yield, plant height and tiller number for MPG1 and wildtype plants for the T3 generation.

Identification of a Gene that Makes Plants Gigantic-1: Characterization of Mpg1, a Novel Mutant of Rice To aid in the production of stable energy, plant lignocellulocic material is currently being used to generate biofuels. To make this system more efficient by increasing plant biomass, a specific T-DNA expression cassette utilizing a gene involving sucrose transport was engineered. FIG. 1A. Through the screening of numerous transgenic plants, we discovered a single plant that was noticeably larger than its counterparts. Genotyping regions of the insertion revealed that only a portion of the T-DNA expression cassette was inserted FIG. 1B but the insertion did not contain the gene of interest pertaining to sucrose transport. The T-DNA insertion was found to be bi-laterally truncated, only containing the selective marker (hygromicin—15-071 resistance gene) and a portion of a companion cell specific promoter. Thus, the increased biomass phenotype was the result of the cassette insertion. FIG. 2. TAIL-PCR on the mutant plant revealed that the location of the T-DNA insertion was in an intergenic region. FIG. 3. The insertion was tracked via PCR across multiple generations while collecting biomass-related data. The presence of the insertion correlated 100% in the segregating plants with increases in all of the biomass characteristics measured. The mutant plants had an average of a 7.4-fold increase in biomass compared to segregating wild-type plants and plants segregating for the insertion had a 3.6-fold increase in seed yield. FIG. 4. We also noted that the maximum increase in biomass occurred when the plants were grown under abiotic stress. Given the substantial increase in biomass shown by the mutant we refer to it as mpg 1 (Makes Plants Gigantic 1). While not wishing to be bound by any theory, the inventors surmised that the insertion caused a mutagenic event that resulted in altered expression and/or function of a nearby gene or genes. RT-PCR along with more comprehensive phenotyping, has led us to the discovery of a candidate transcription factor that is differentially expressed when the T-DNA construct is present. Other phenotypic evidence suggests that the degree of the phenotype compared to wild-type segregants might also be influenced by abiotic and/or biotic stress. Identification of the mechanism responsible for the increased biomass in mpg1 may lead to strategies that could be applied to all crops, including those focused on bioenergy, food, fiber and specialty products.

Nomenclature Used

True Wild Type Plants (TWT)—WT plants that havnet undergone any known form of manual manipulatioin in previous/current generations Wild type Segregants (WTs)—Offspring from the T-DNA mpg1 tansgenic palnts that arose form a segregating population, not contianing a copy of the T-DNA insertion.

Heterozygous Segregants 9HT)—Offspring from the T-DNA mpg1 transgenic plants that arose form a segregating population, containing one copy of the T-DNA insertion.

Figure 6:
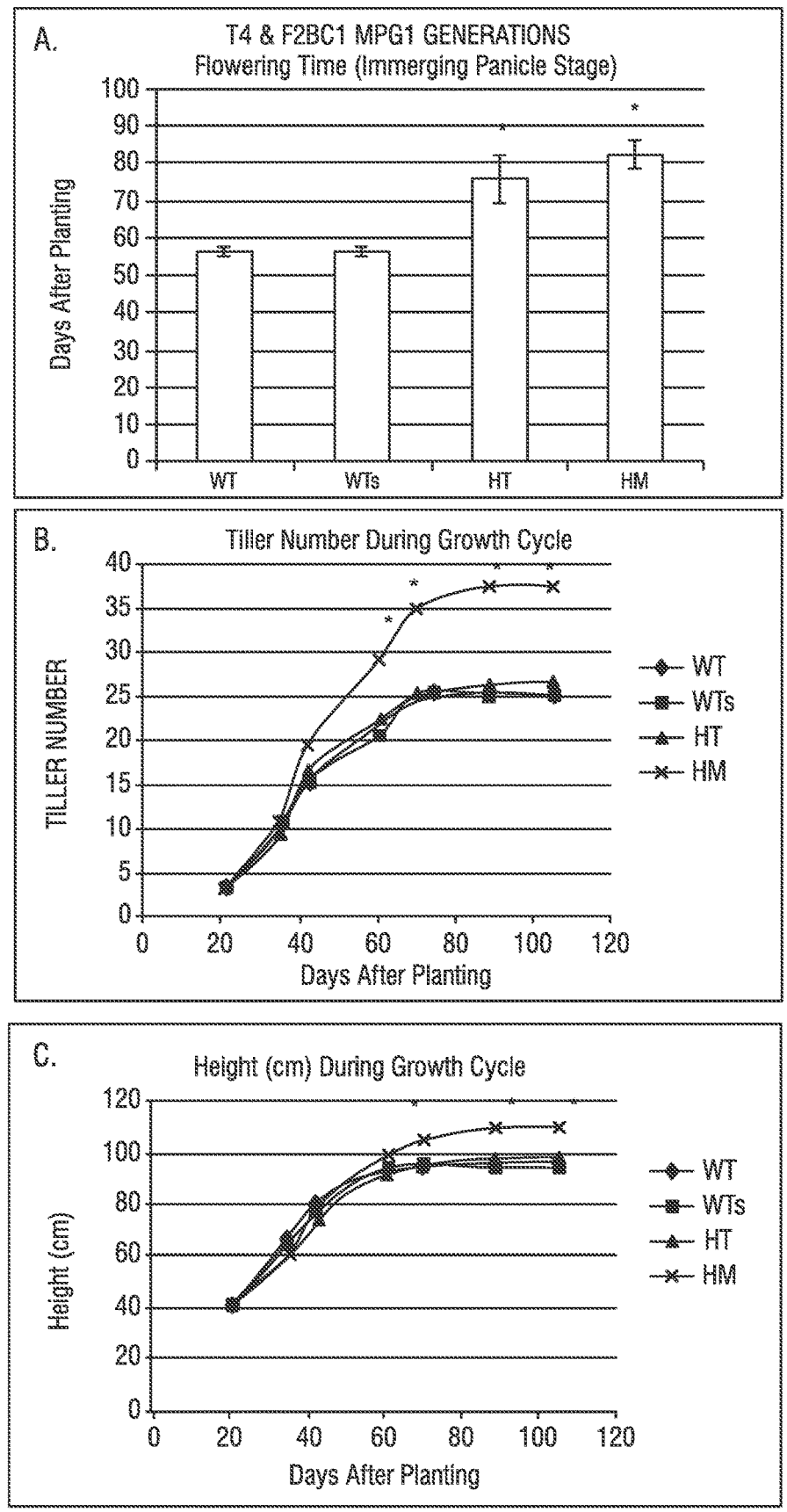
FIGS. 6A-6C are graphs of phenotypic measurements of the mpg1 mutant T4 and F2BC1 populations. 6A flowering time till emerging panicle stage, 6B tiller number during lifecycle, and 6C height (cm) during lifecycle. $P<0.05$.
Figure 7:
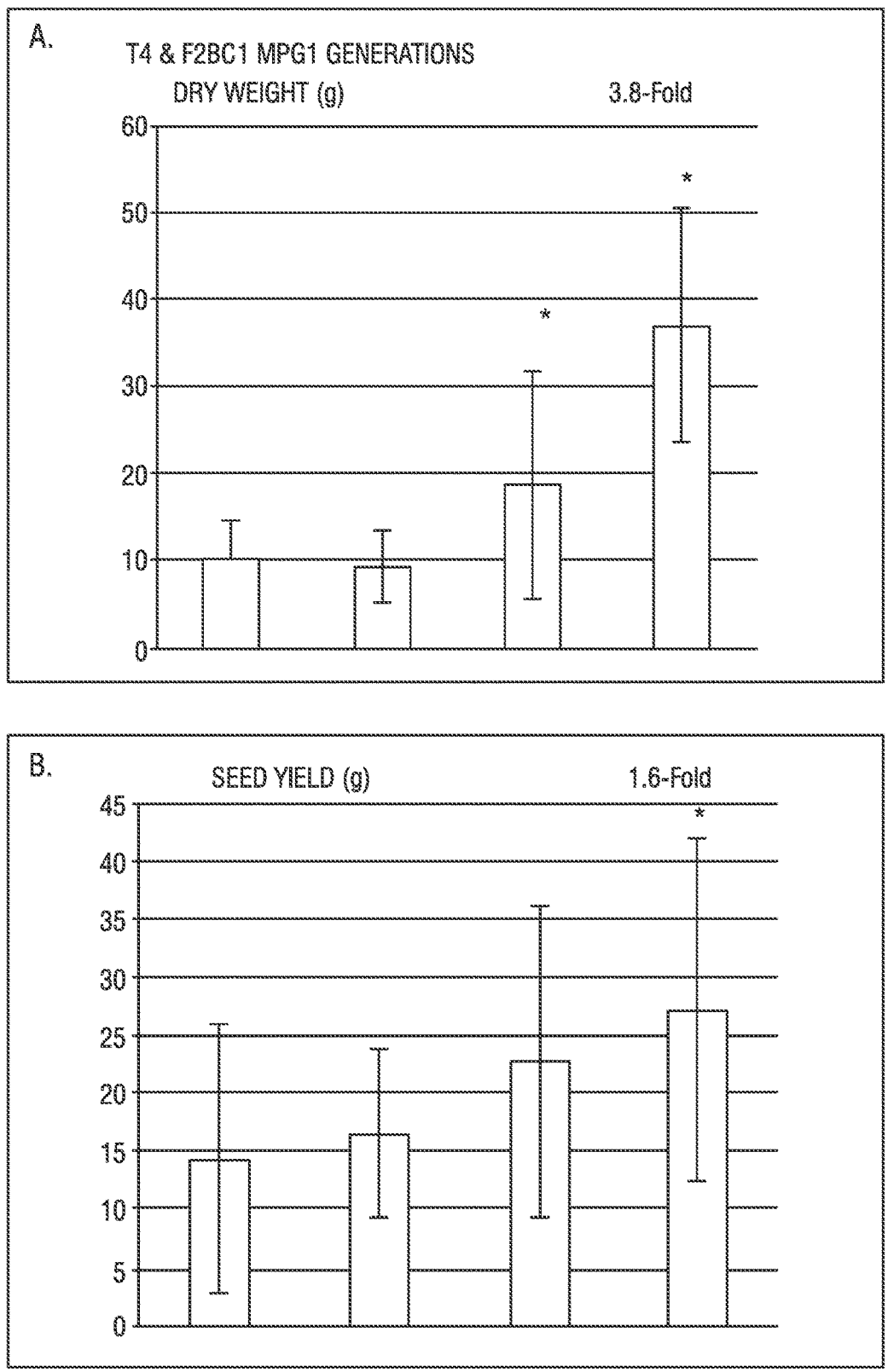
FIGS. 7A and 7B are graphs showing phenotypic measurements of the mpg1 mutant T4 and F2BC1 population's 7A dry weight (g) and 7B seed yield (g) $P<0.05$.
Figure 8:
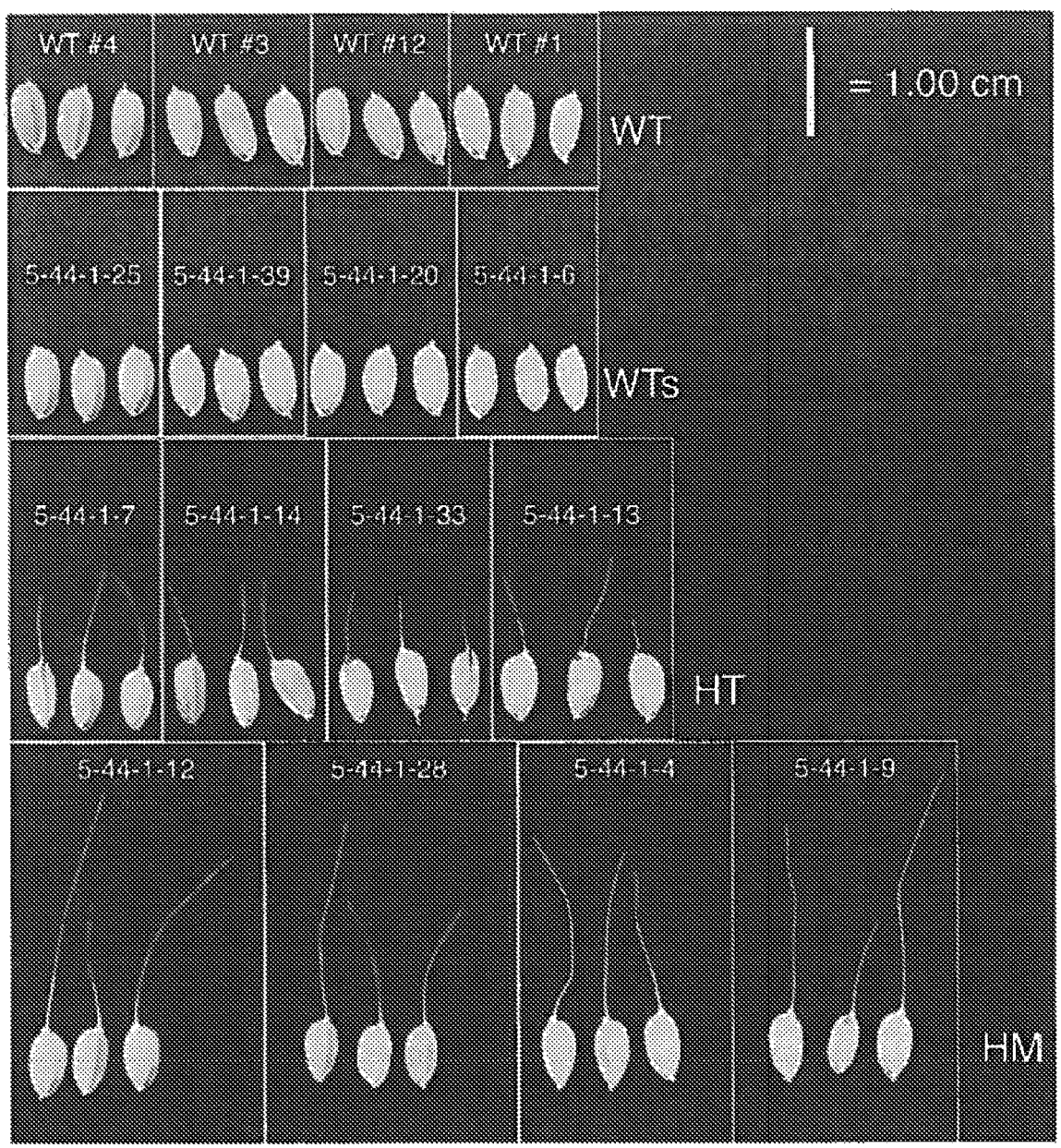
FIG. 8 shows the seeds of individual spikelets from a segregating population line (5-44-1 from the T4 and F2BC1 populations. Spikelet presence and lengths were measured and compared to WT.
Figure 9:
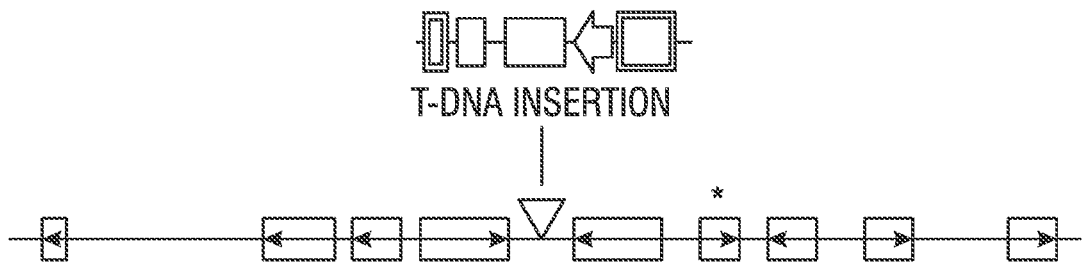
FIG. 9 shows the RT-PCR revealed insertion of the T-DNA construct location and candidate genes.
Figure 10:
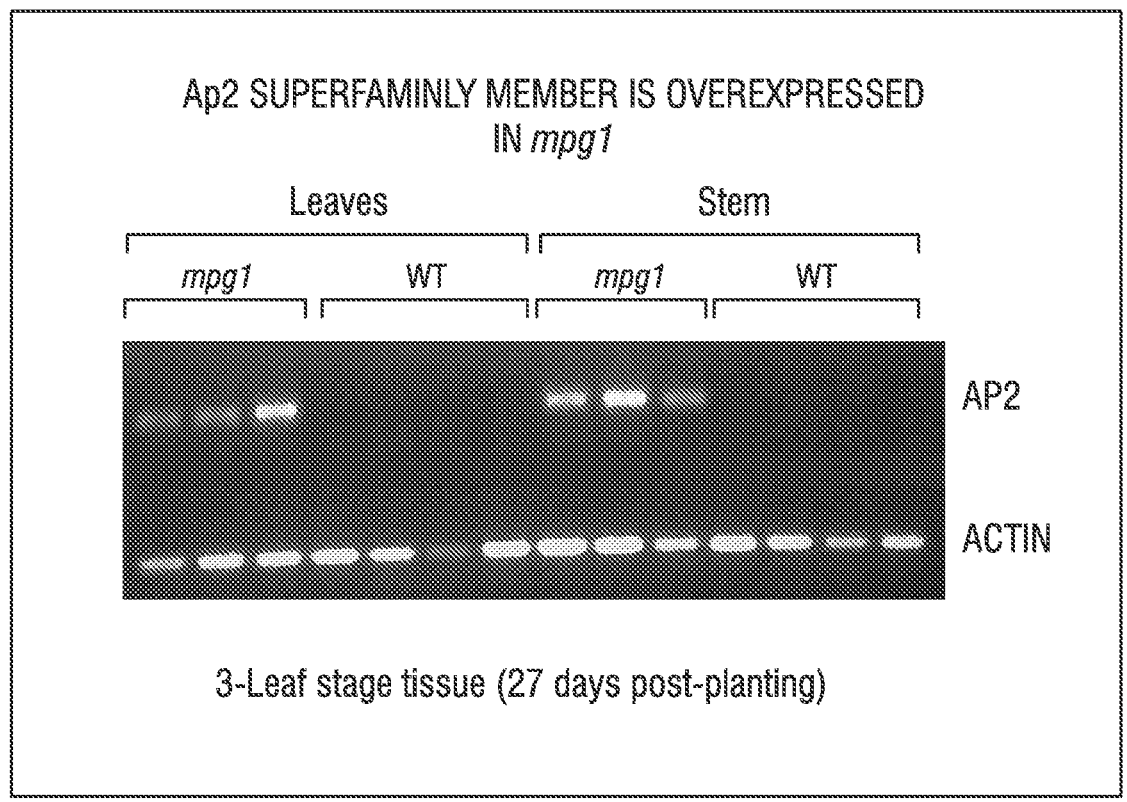
FIG. 10 shows that MPG1/AP2 expression is overexpressed in leaves and stems compared to wildtype plants.
Figure 11:
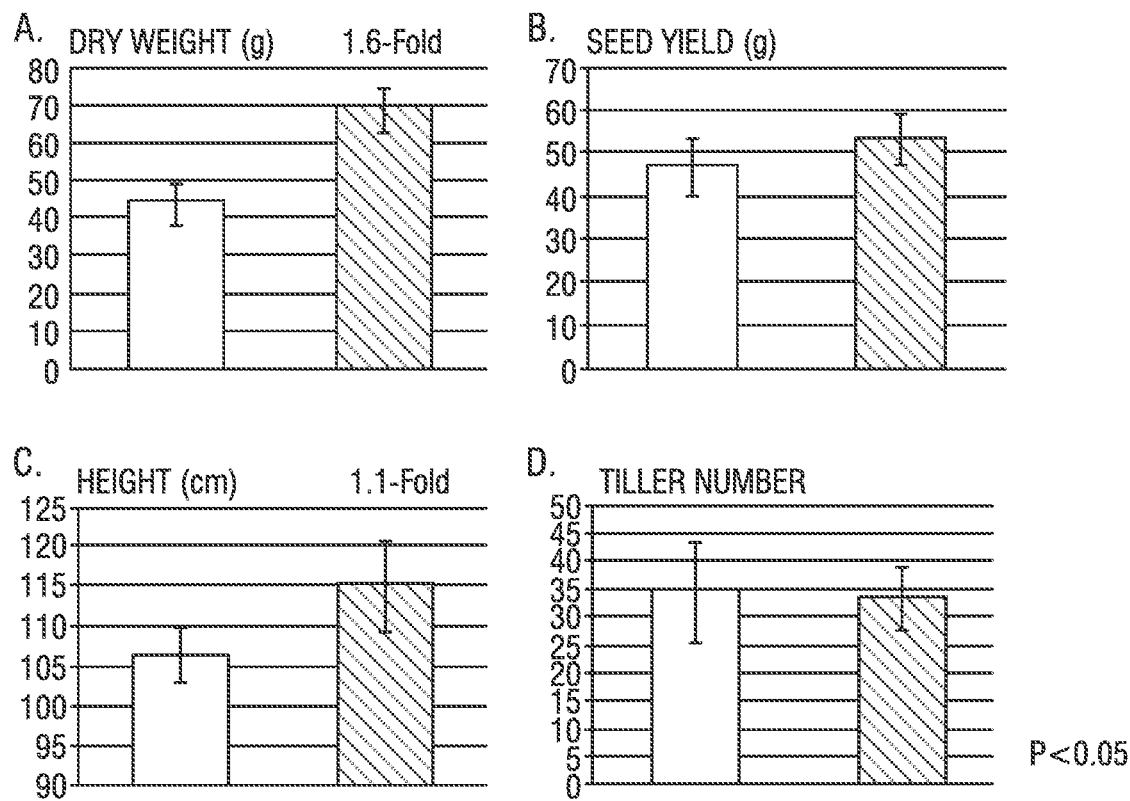
FIGS. 11A-11D shows the T3 plants with new medium and fertilizer for dry weight, seed yield, plant height, and tiller number for mpg1 plants and wildtype plants.
Figure 12:
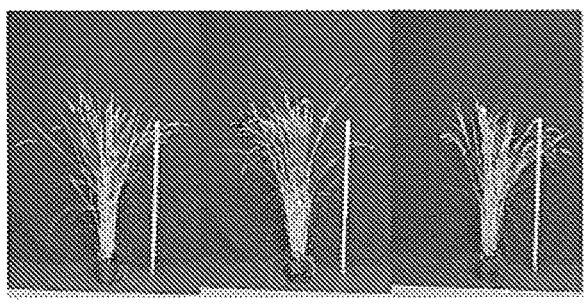
FIGS. 12A and 12B show the phenotypic effects of a new soil and fertilizer treatment from T3 generation growth chamber compared to the effects of (B) previous soil and fertilizer treatments among T4 and F2BC1 greenhouse populations of mpg1.
Figure 12:
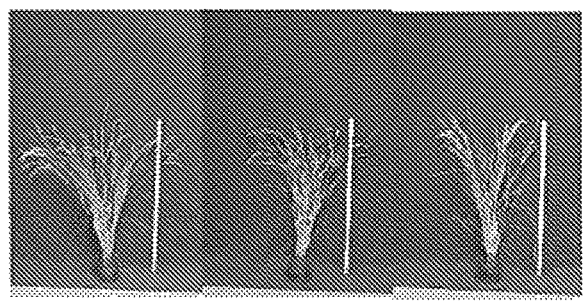
Figure 12:
Figure 13:
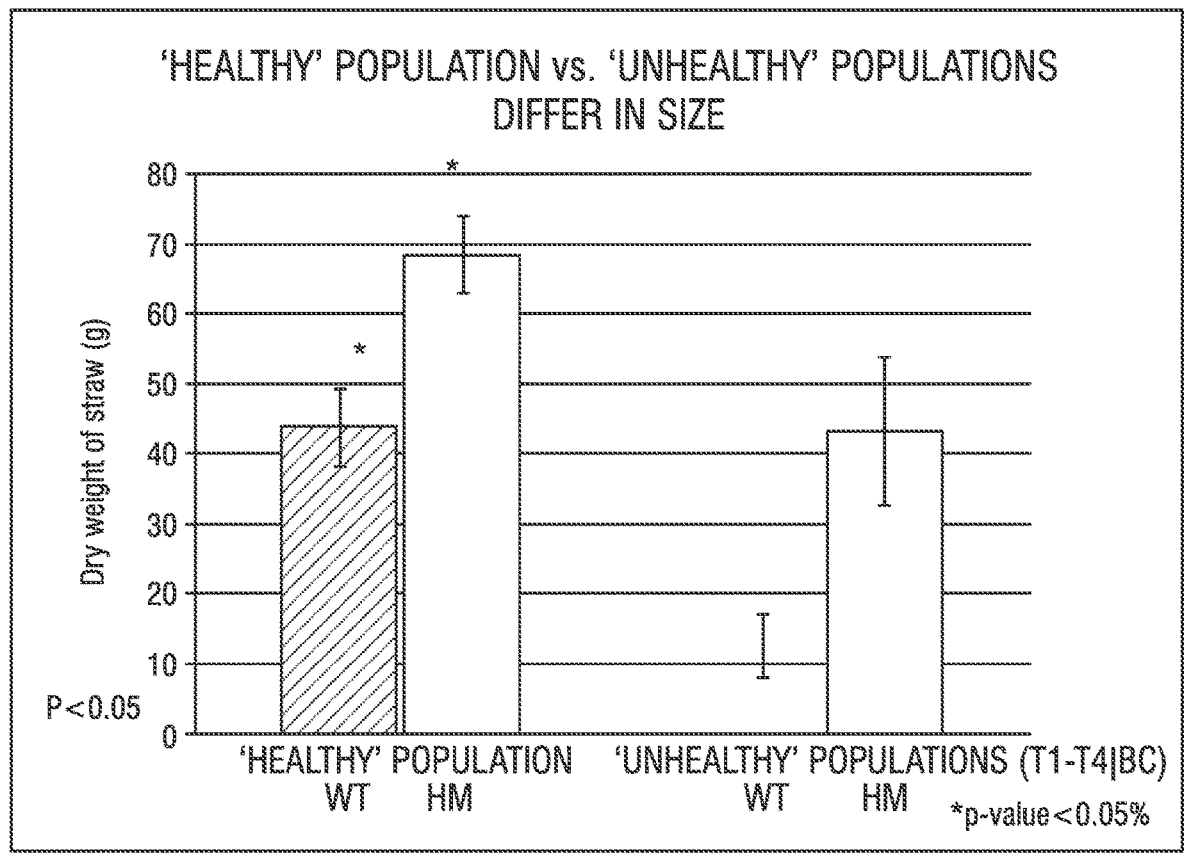
FIG. 13 is a graph showing the differences in dry weight between MPG1 plants and wildtype in healthy of non-stressed conditions verses stressed conditions.
Figure 14:
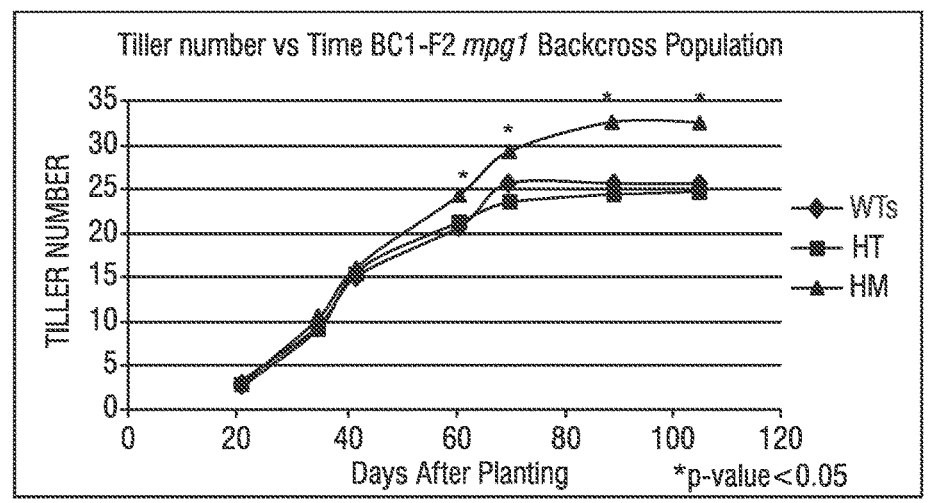
FIG. 14 demonstrates that mpg1 plants have more tillers compared to wildtype segregants in non-optimal conditions.
Figure 15:
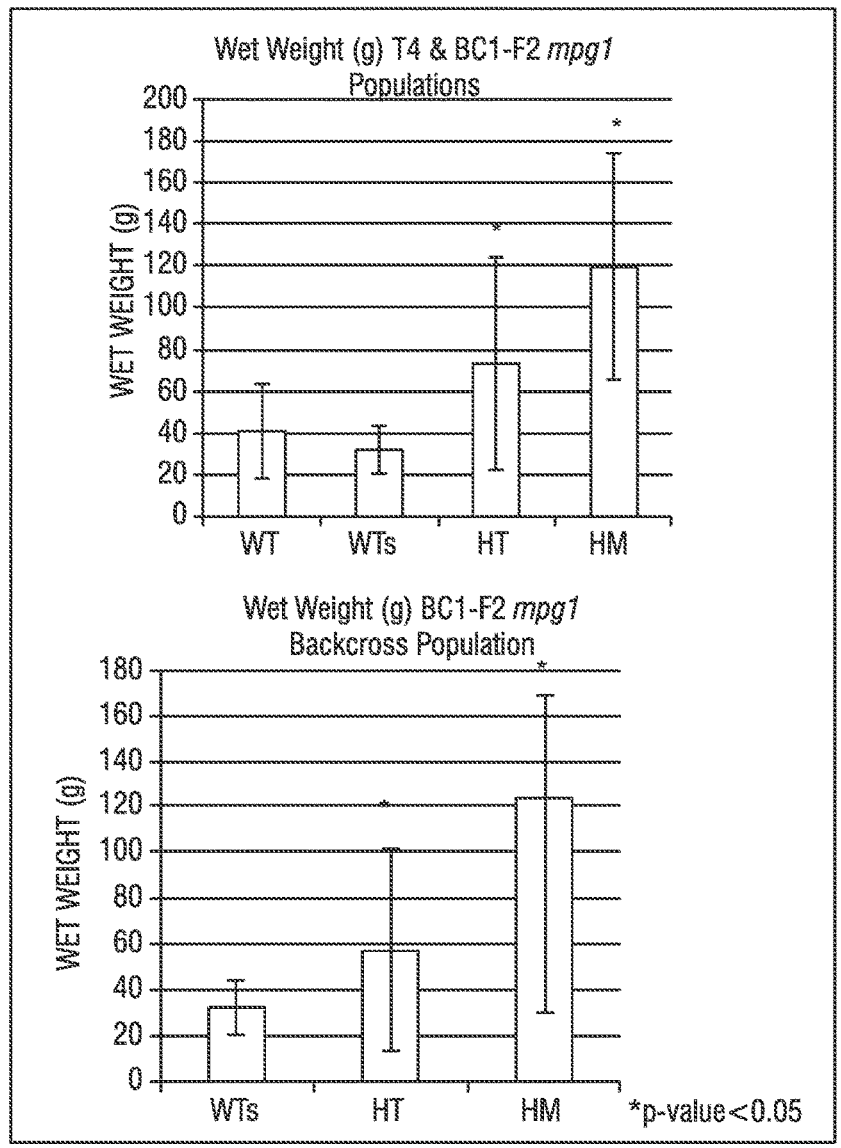
FIG. 15 sows that mpg1 plants have increased wet weight compared to wild-type segregants in non-optimal conditions.
Figure 16:
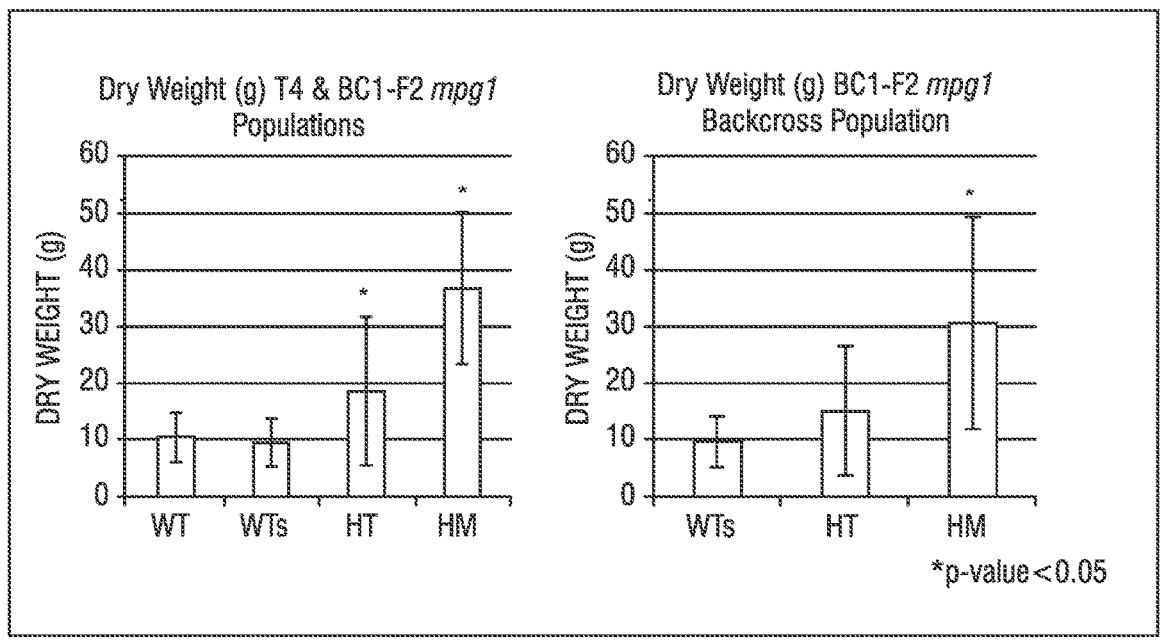
FIG. 16 shows mpg1 plants have increased dry weight compared to wild type segregants in non-optimal conditions.
Figure 17:
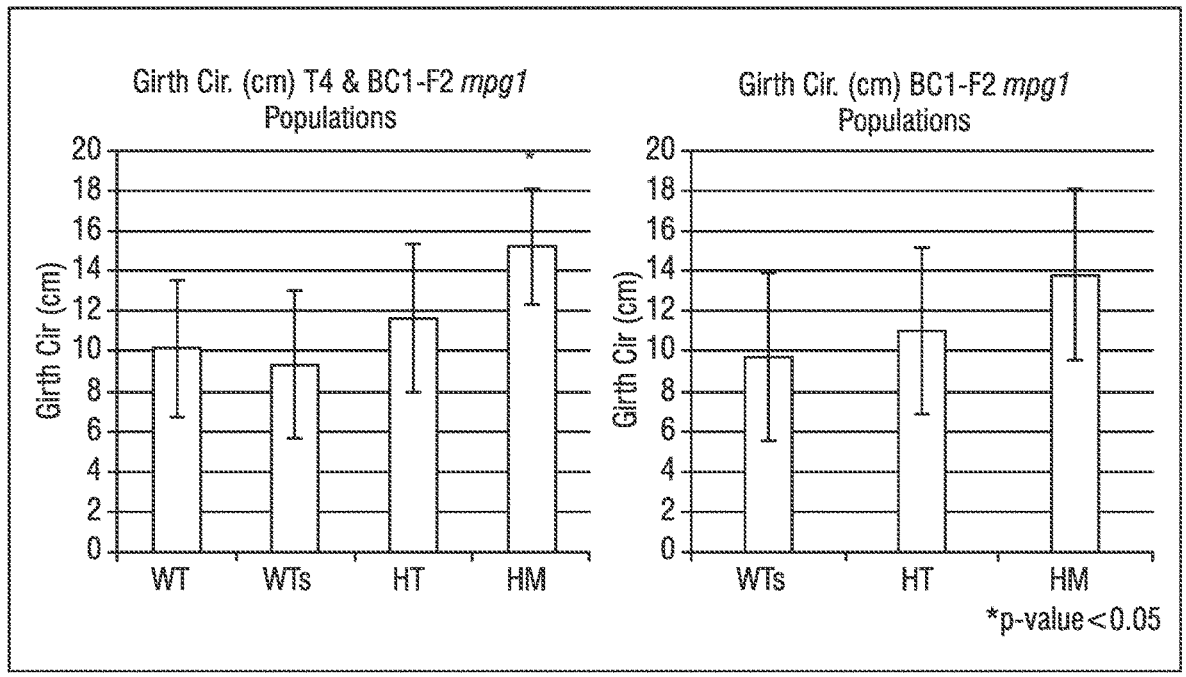
FIG. 17 demonstrates that mpg1 plants have increased plant circumference (girth) compared to wildtype segregants in non-optimal conditions.
Figure 18:
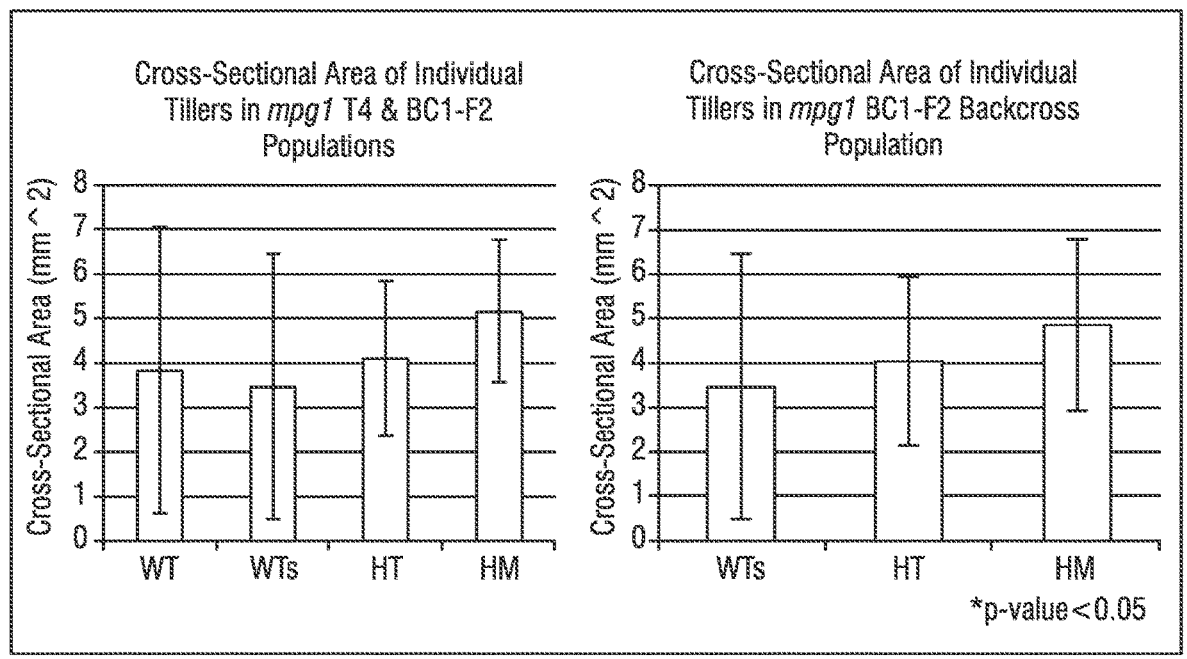
FIG. 18 shows that mpg1 plants have increased tiller size compared to wildtype segregants in non-optimal conditions.
Figure 19:
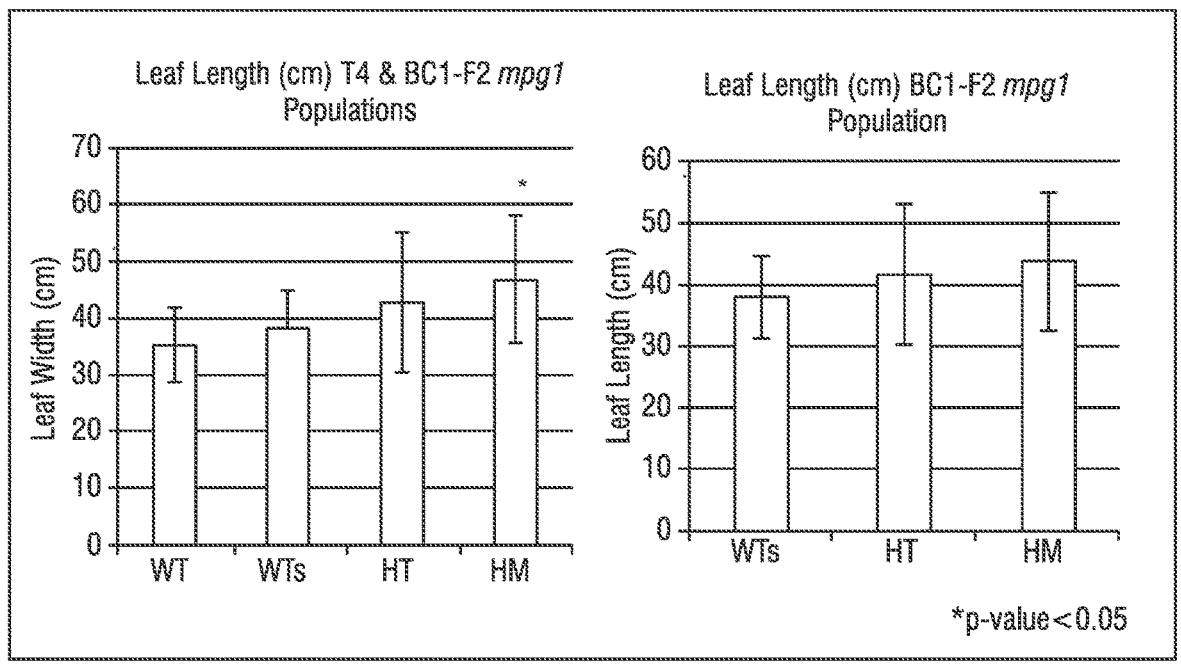
FIG. 19 shows that mpg1 plants have increased leaf length compared to wildtype segregants in non-optimal conditions.
Figure 20:
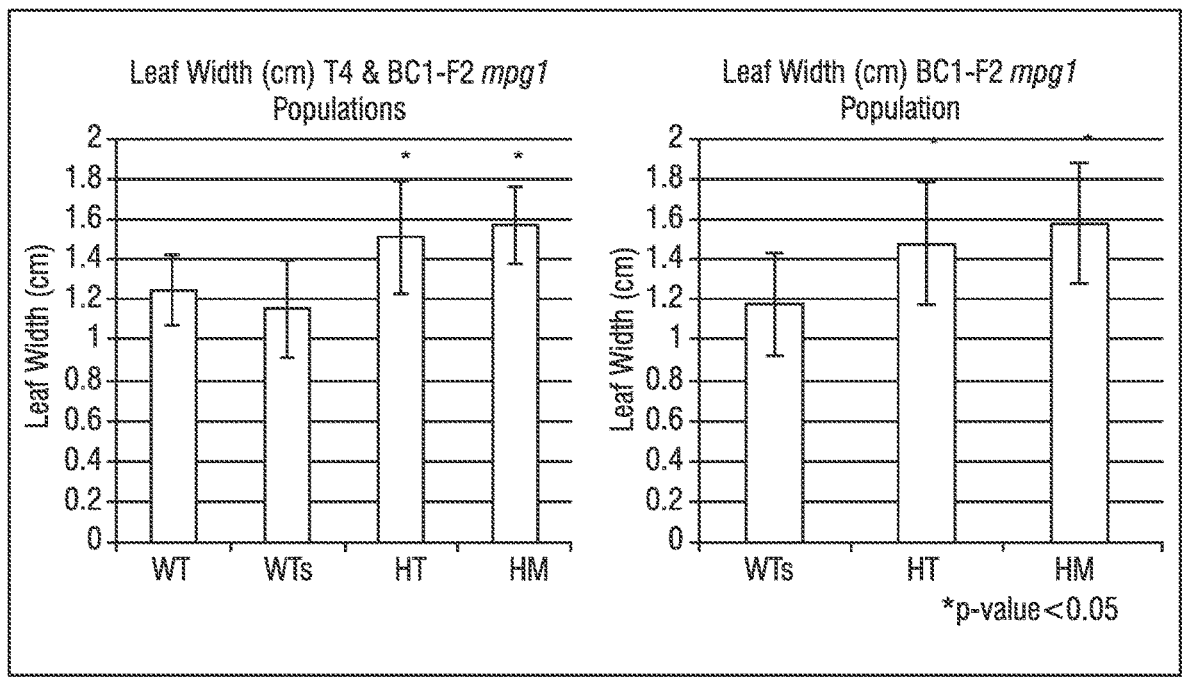
FIG. 20 shows that mpg1 plants have increased leaf width compared to wildtype segregants in non-optimal conditions.
Figure 21:
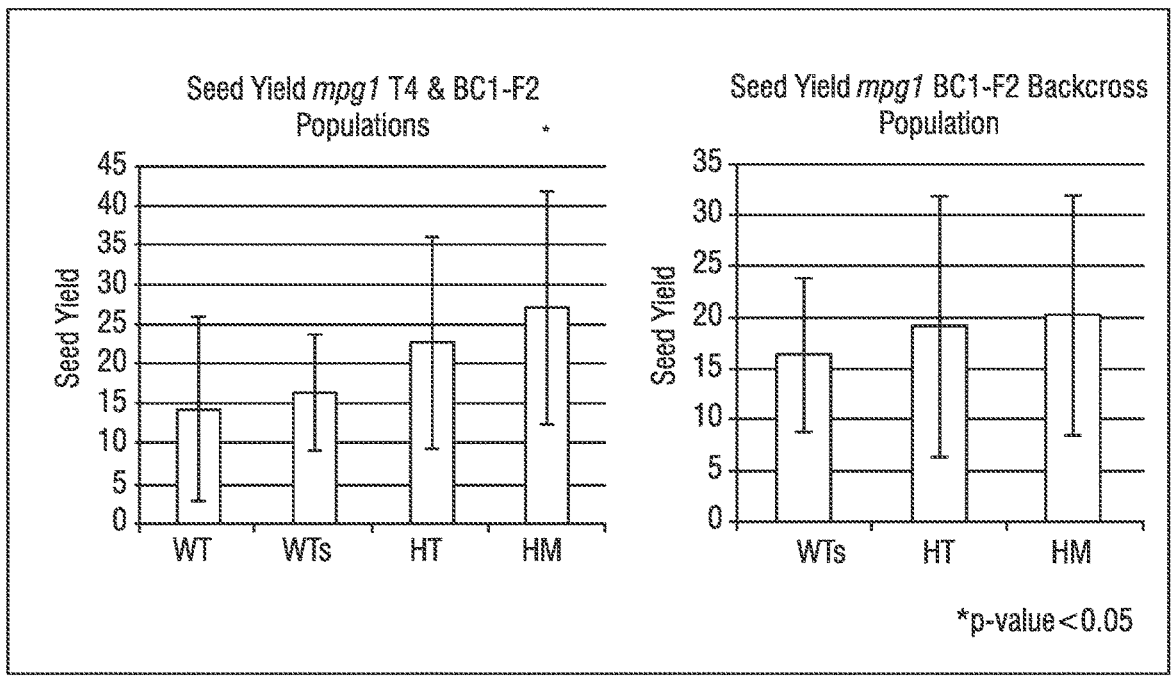
FIG. 21 shows that mpg1 plants have increased seed yield compared to wildtype segregants in non-optimal conditions.
Figure 22:
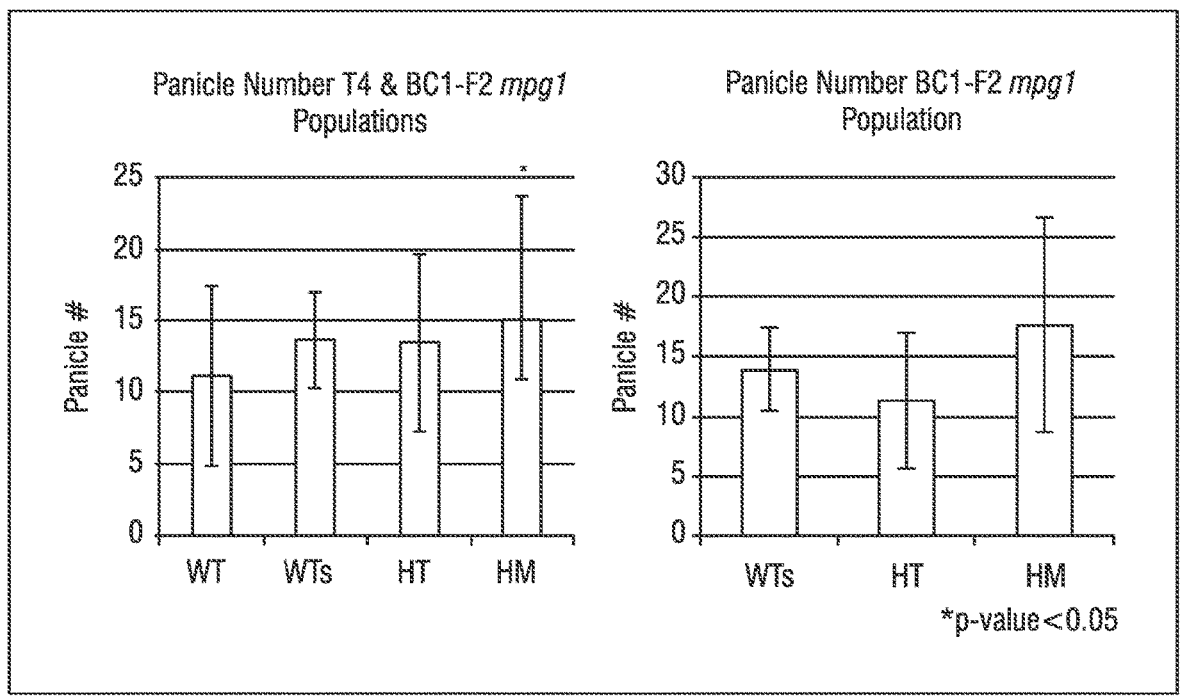
FIG. 22 shows that mpg1 plants have increased panicle number compared to wildtype segregants in non-optimal conditions.
Figure 23:
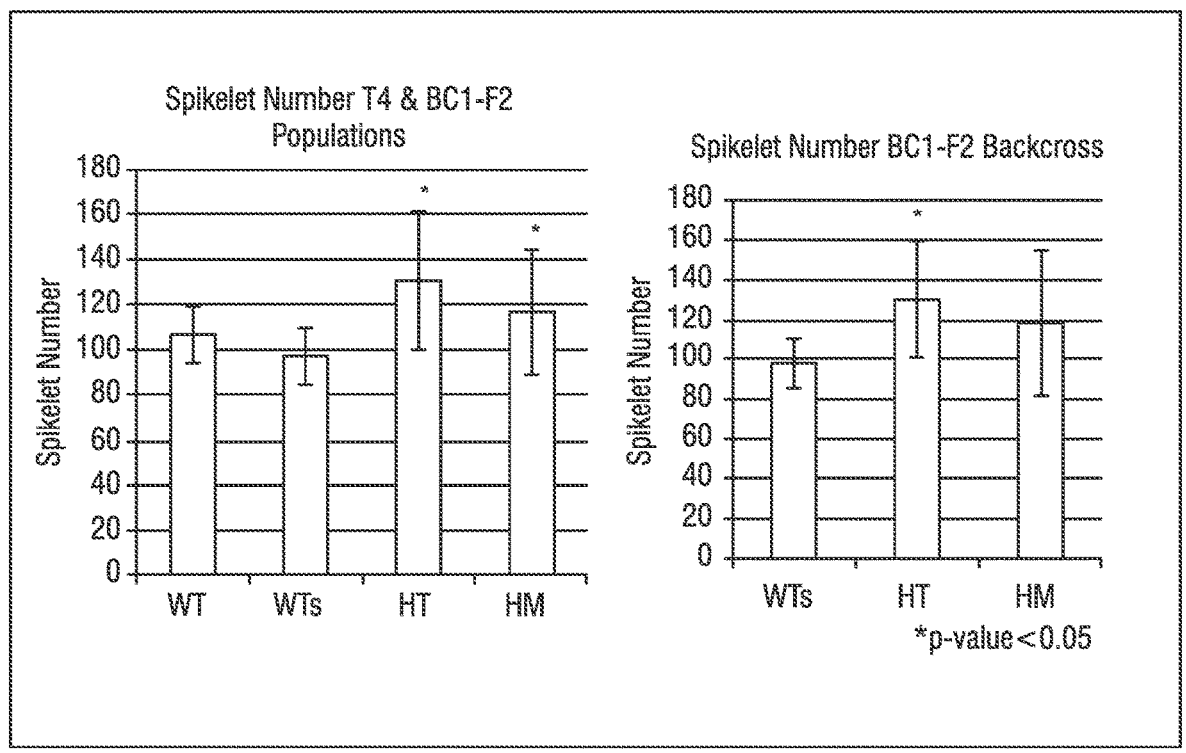
FIG. 23 shows that mpg1 plants have increased spikelet number compared to wildtype segregants in non-optimal conditions.
Figure 24:
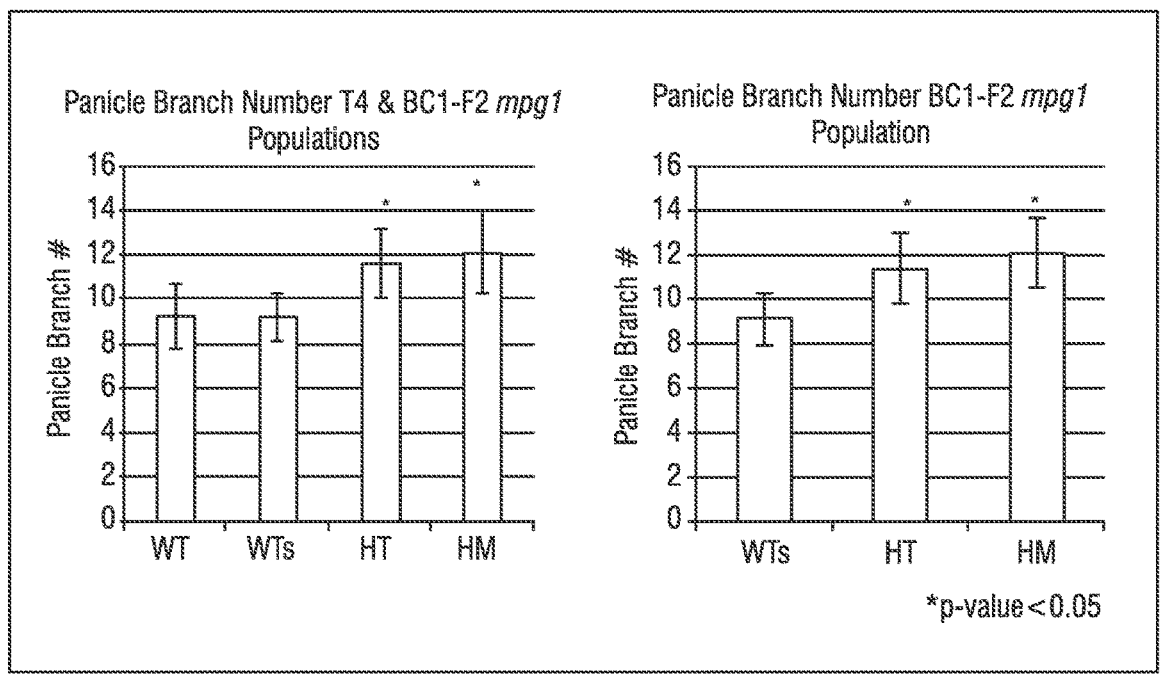
FIG. 24 shows that mpg1 plants have increased number of panicle branches compared to wildtype segregants in non-optimal conditions
Figure 25:
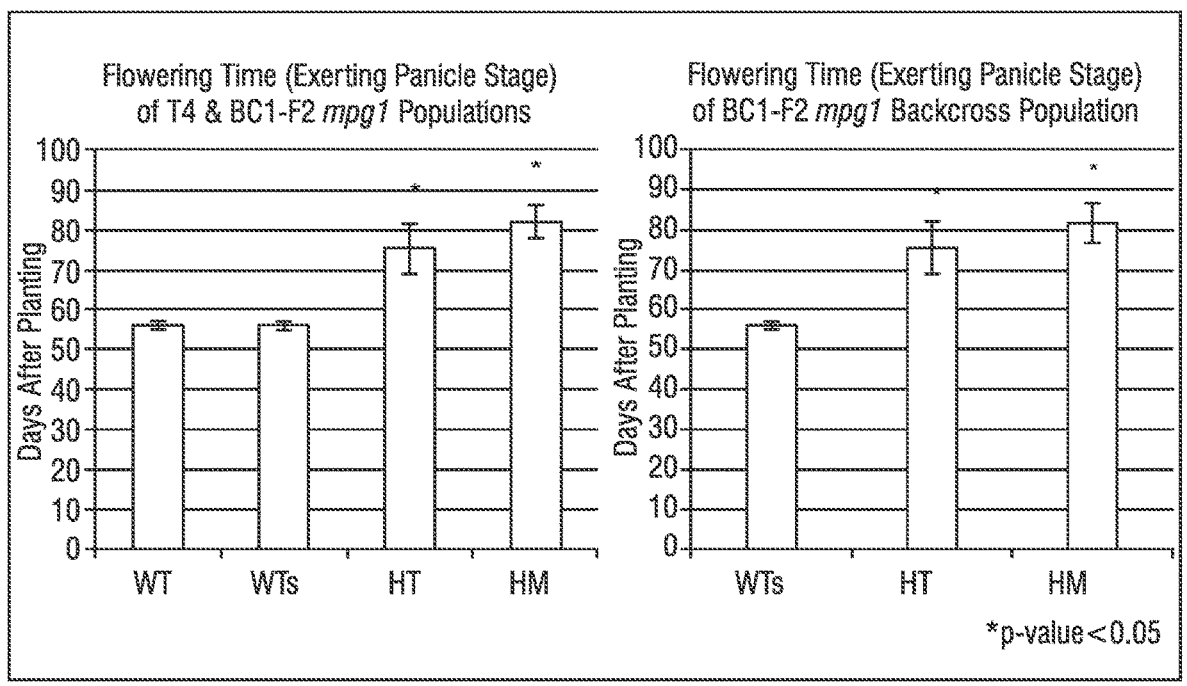
FIG. 25 shows that mpg1 plants have a delay in flowering time compared to wildtype segregants in non-optimal conditions.
Figure 26:
FIG. 26 is a photograph demonstrated that mpg1 plants have increased biomass.
Figure 27:
FIG. 27 is a photograph showing that mpg1 plants have increased biomass compared to wildtype segregants in non-optimal conditions.
Figure 28:
FIG. 28 is a photograph showing that mpg1 plants have increased biomass compared to wildtype segregants in drought conditions.
Figure 29:
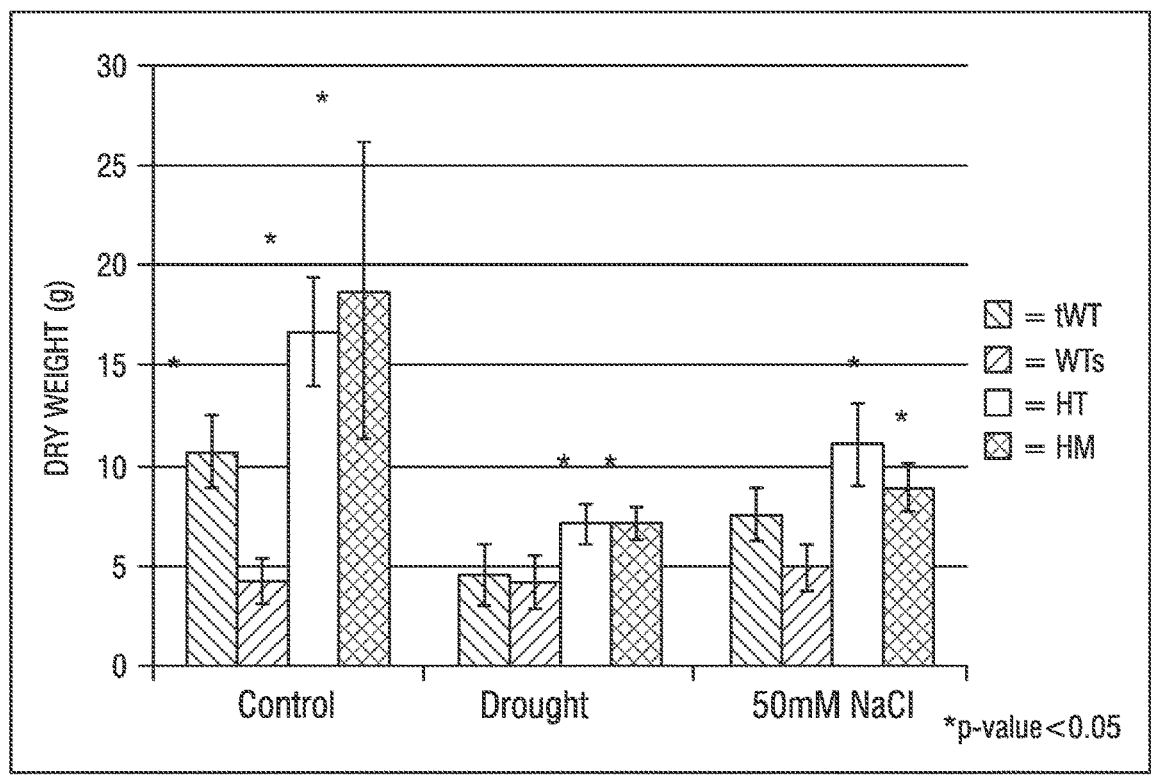
FIG. 29 is a graph showing that mpg1 plants have increased dry weight compared to wildtype segregants in salt stressed conditions (50 mM NaCl).
Figure 30:
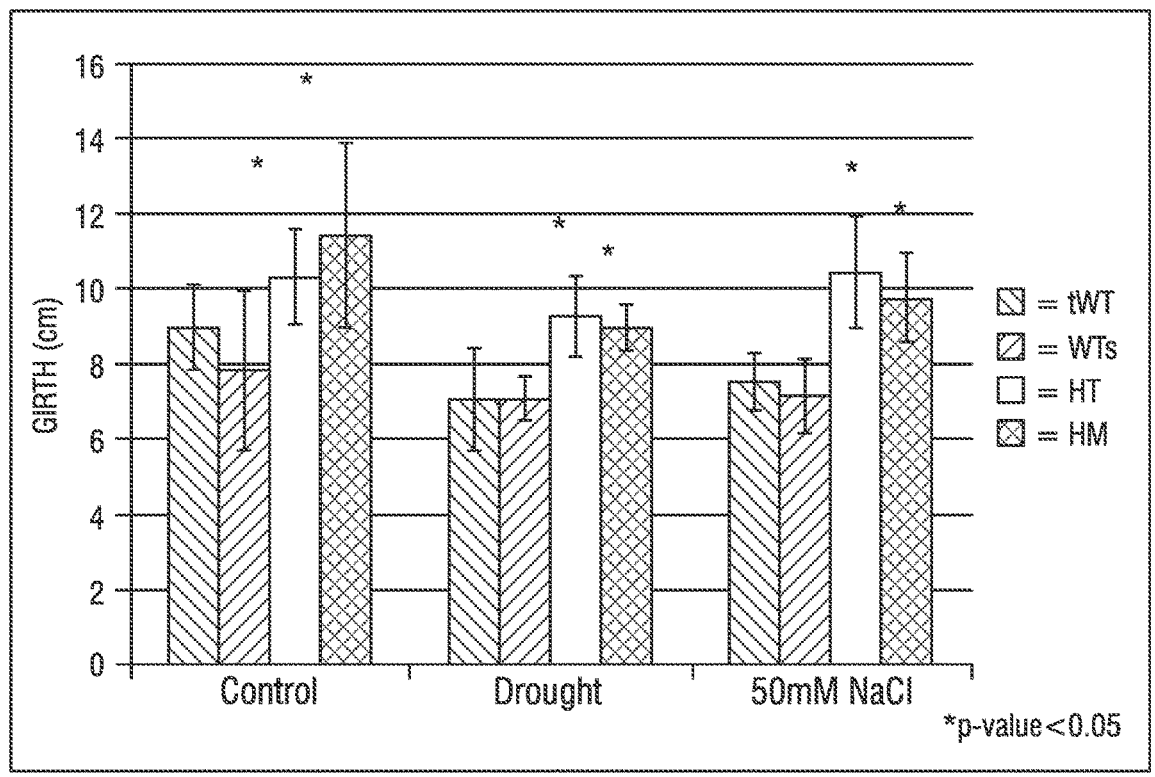
FIG. 30 shows that mpg1 plants have increased girth compared to wildtype segregants in both optimum and stressed conditions.
Figure 31:
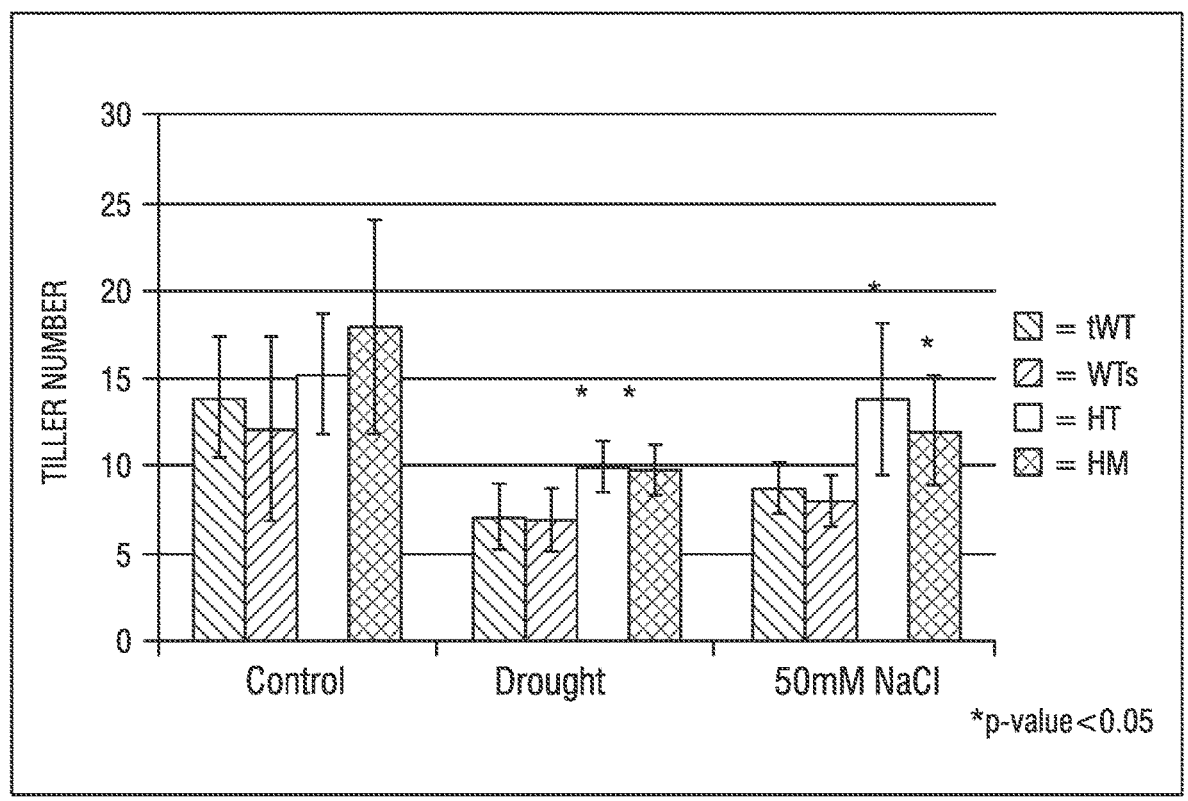
FIG. 31 shows that mpg1 plants have increased tiller number compared to wildtype segregants in both optimum and stressed conditions.
Figure 32:
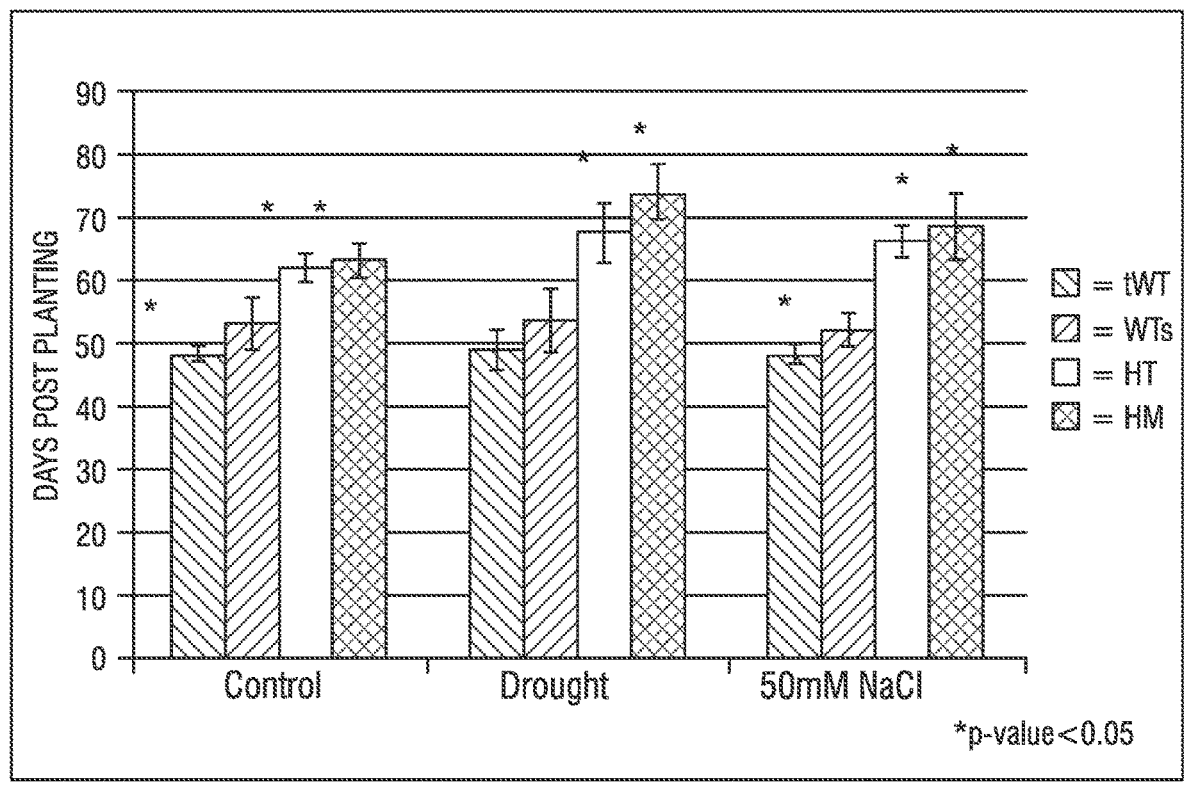
FIG. 32 shows that mpg1 plants have a delay in flowering time increased tiller to size compared to wildtype segregants in both optimum and stressed conditions
Figure 33:
FIG. 33 shows that mpg1 plants have increased biomass compared to wildtype segregants in non-optimal conditions.
Figure 34:
FIG. 34 shows that mpg1 plants have increased biomass size compared to wildtype segregants in non-optimal conditions.
Figure 35:
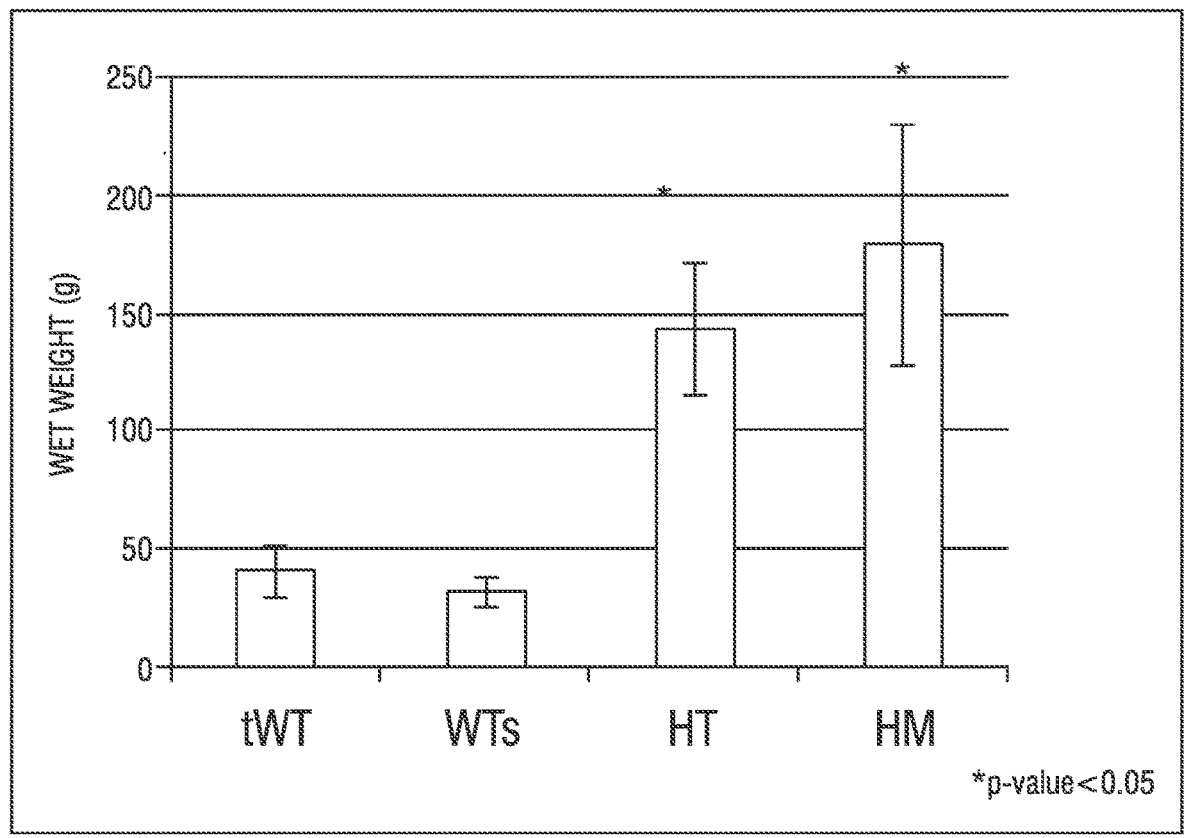
FIG. 35 shows that mpg1 plants have increased wet weight compared to wildtype segregants in non-optimal conditions.
Figure 36:
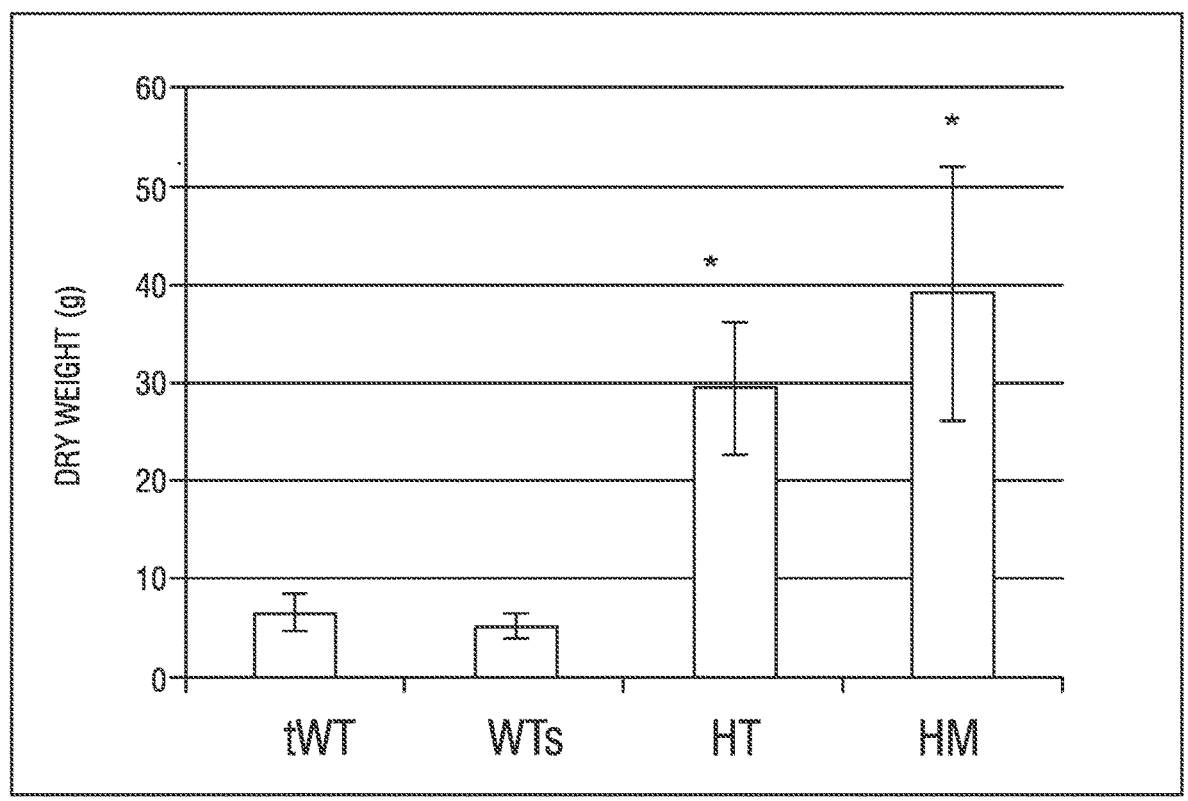
FIG. 36 shows that mpg1 plants have increased dry weight compared to wildtype segregants in non-optimal conditions.
Figure 37:
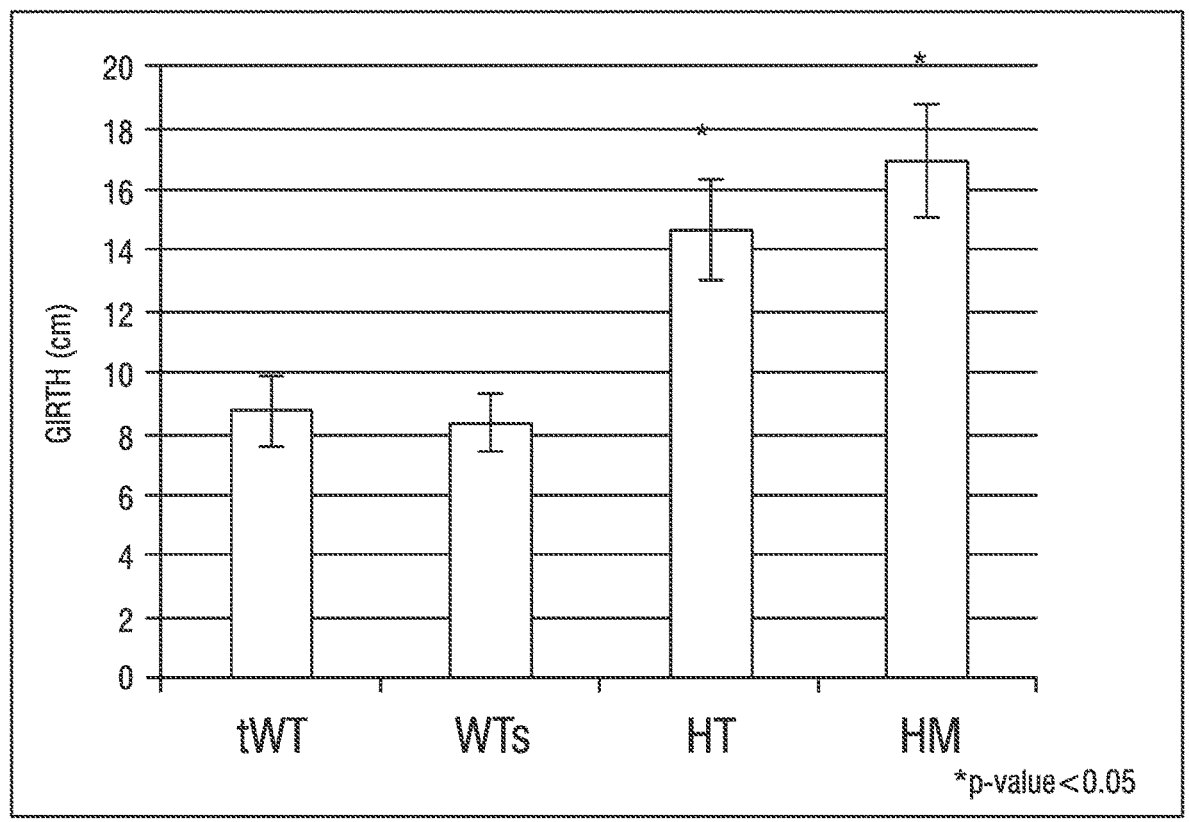
FIG. 37 shows that mpg1 plants have increased girth compared to wildtype segregants in non-optimal conditions.
Figure 38:
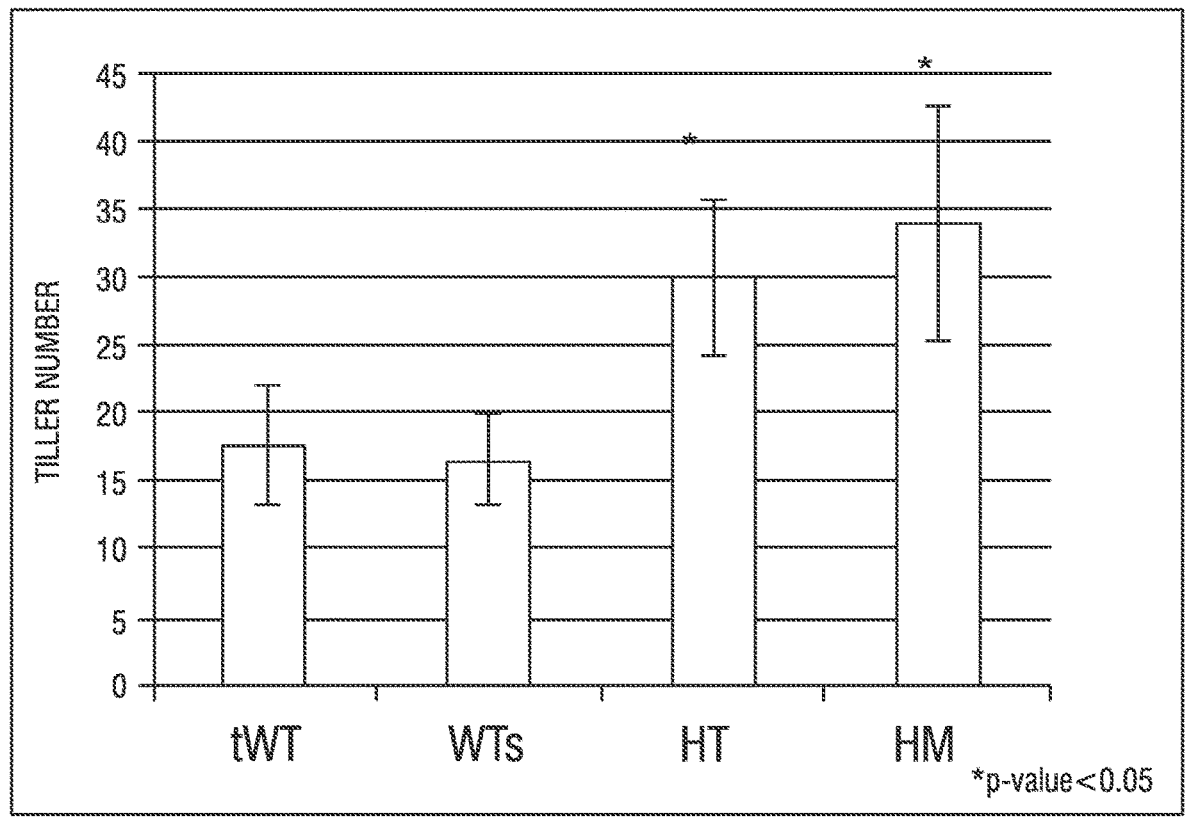
FIG. 38 shows that mpg1 plants have increased tiller number compared to wildtype segregants in non-optimal conditions.
Figure 39:
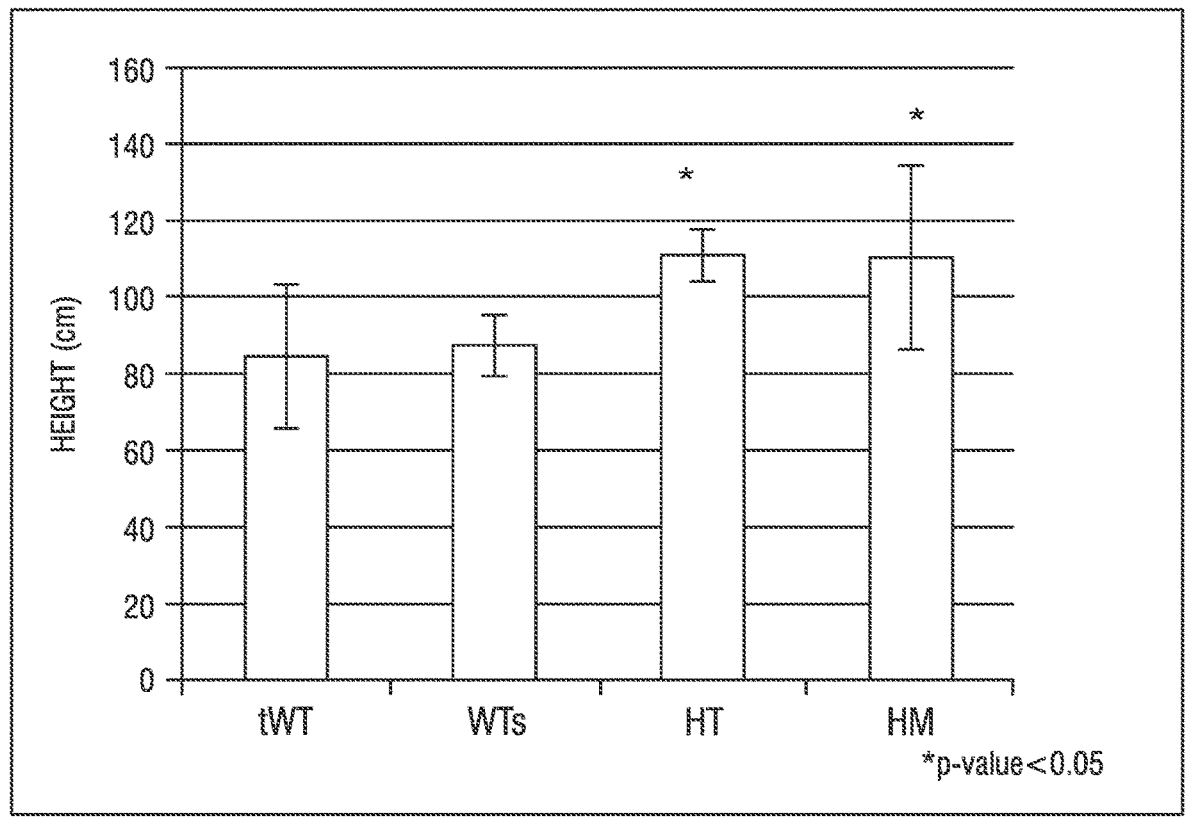
FIG. 39 shows that mpg1 plants have increased height compared to wildtype segregants in non-optimal conditions.
Figure 40:
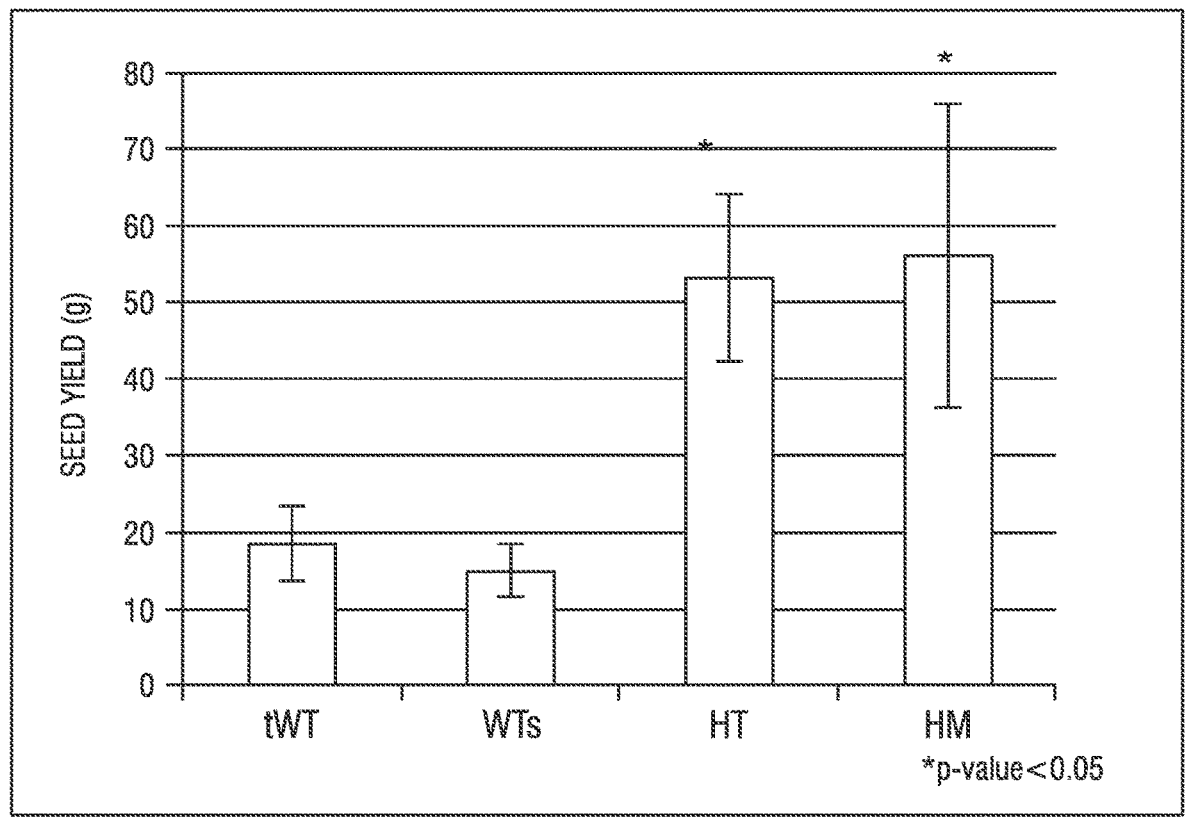
FIG. 40 shows that mpg1 plants have increased seed yield compared to wildtype segregants in non-optimal conditions.
Figure 41:
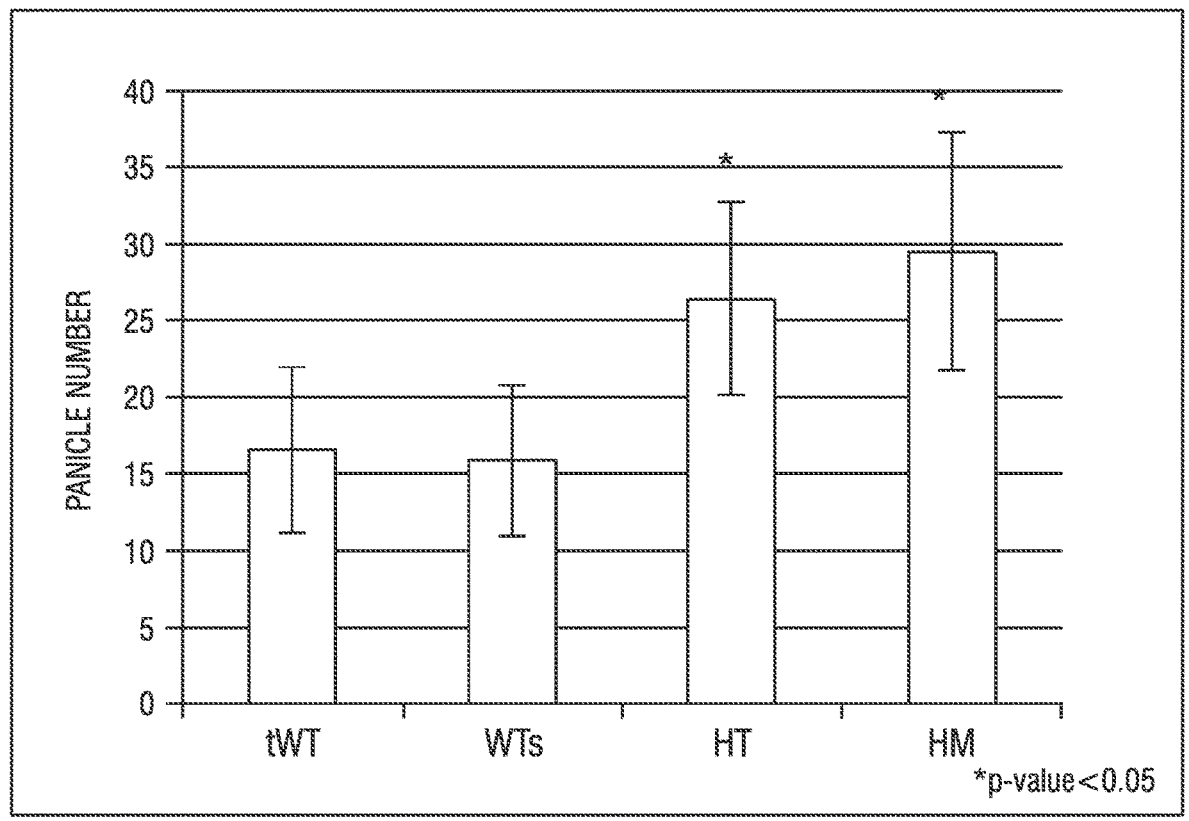
FIG. 41 shows that mpg1 plants have increased panicle number compared to wildtype segregants in non-optimal conditions.
Figure 42:
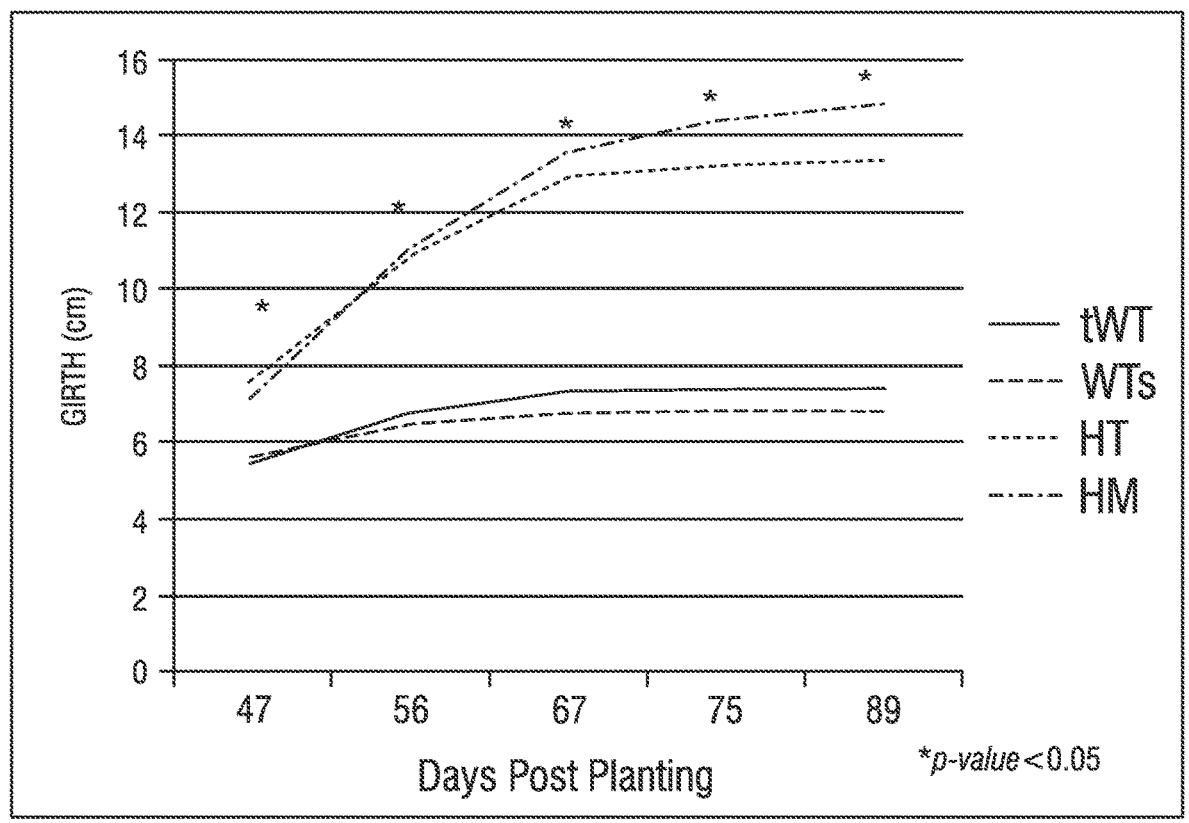
FIG. 42 shows that mpg1 plants have increased girth compared to wildtype plants prior to flowering.
Figure 43:
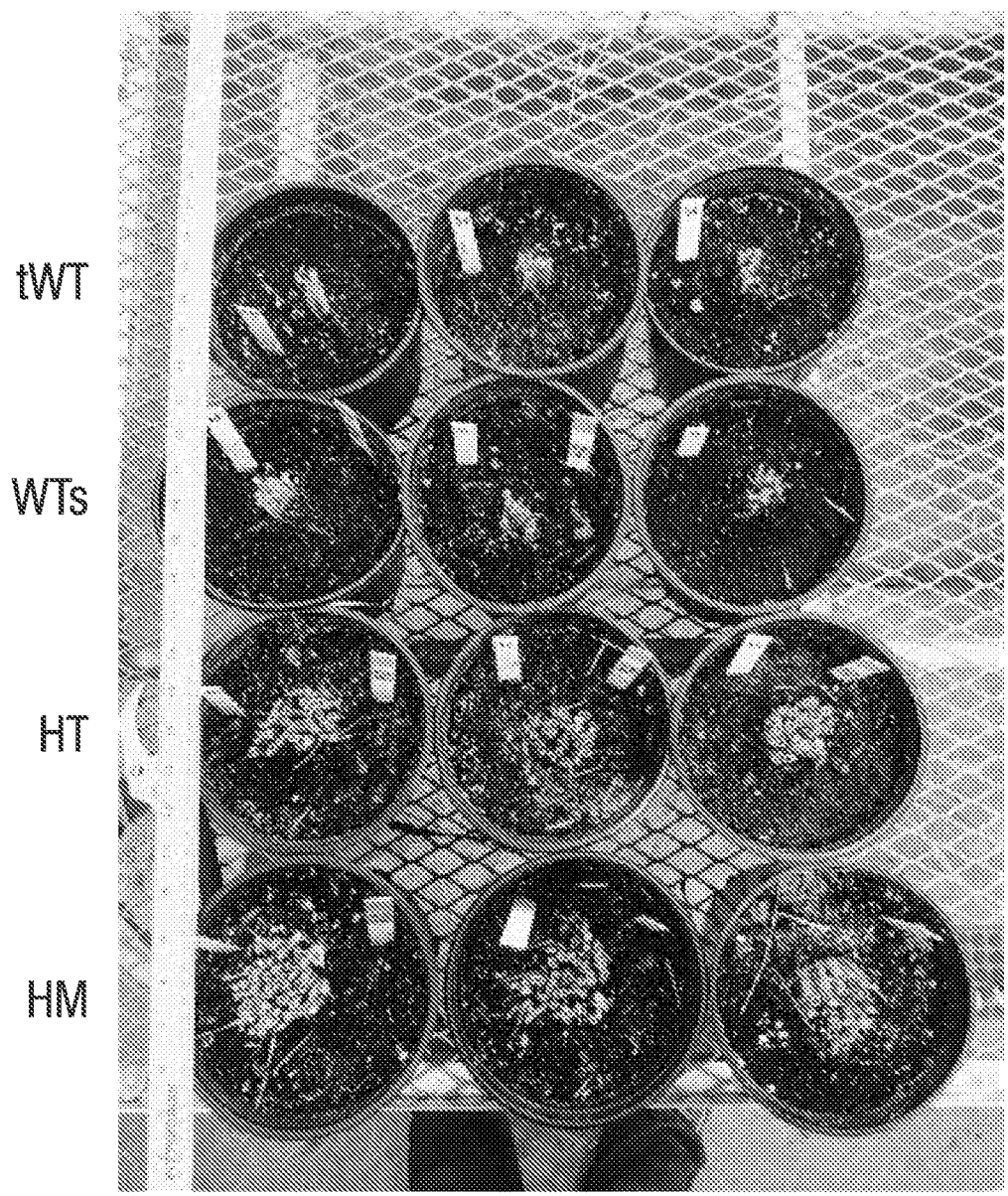
FIG. 43 shows that mpg1 plants have increased girth and tiller number compared to wildtype plants prior to flowering.
Figure 44:
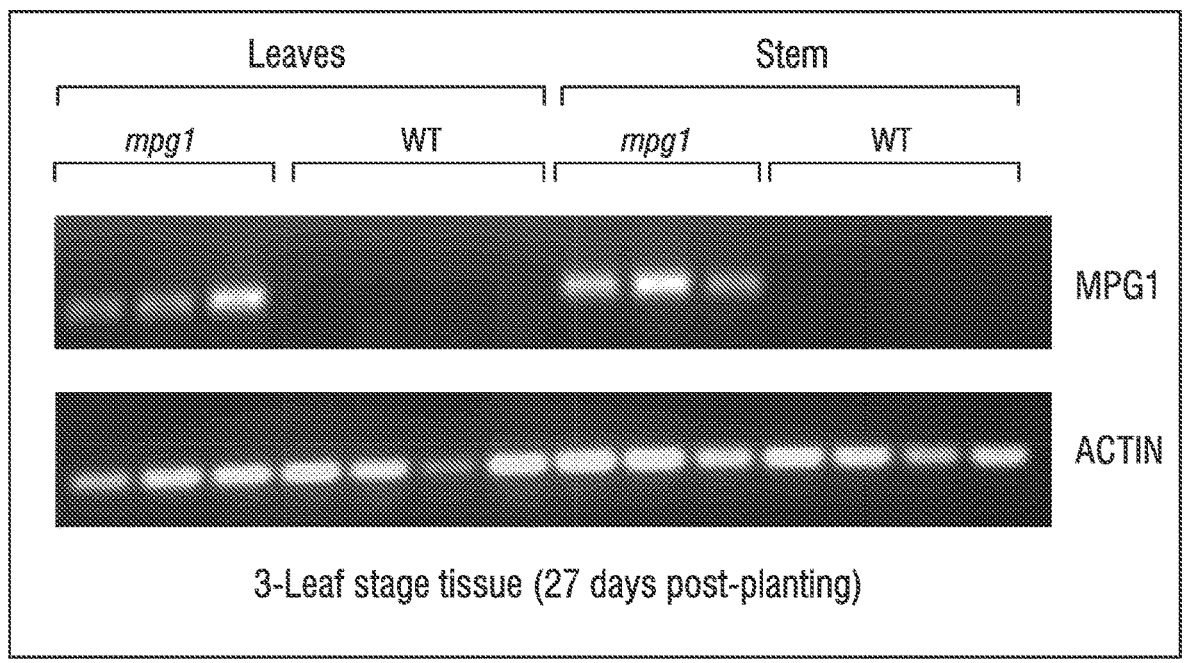
FIG. 44 is a molecular analysis of pmg1 gene expression in the mpg1 mutant.

Homozygous Segregants (HM)—Offsapring from the T-DNA mpg1 transgenic plants that arose form e a segregating population, containing two copies of the T DNA insertion See FIG. 6 showing improvements in tiller number, flowering time and height for the F2BC1 population. FIG. 7 shows the 3.8 fold dry weight increase and 1.6 fold increase of the mutant T4 and F2BC1 populations. FIG. 8 shows the increase in presence and length of awns on spikelets from the F2BC1 and T4 generation. FIG. 9 shows the location of the insertion. FIG. 10 shows that the mpg1 gene (AP2 transcription factor) is overexpression in both stems and leaves at the three leaf stage in the mutant plants. FIG. 10 shows the increase in tiller number, dry weight, height, and seed yield in the growth population of a non-stressed environment. FIG. 11 shows the phenotypic effects of new soil and fertilizer treatment of T3 generation. FIG. 12 shows the differences in dry weight of wildtype and mutant plants in healthy and stressed environments.

Example 2

It was decided to change the soil medium and fertilizer to create more optimal growth conditions for the rice plants, due to the possible salt accumulation and pH instability. This would allow for growth of plants in (non-stressed) environments. An additional T3 generation was grown in a growth chamber to try and reduce any potential influences on the plants.

The HM and WTs alike were noticeably healthier in appearance and were much larger than preceding populations.

When assessing the average biomass accumulation amongst the first few experiments where we now believe the plants were under stressful growth conditions and that of the plants grown in optimal conditions, it would suggest that stress-resistance of the mutant plays a role in the degree of the phenotype. The plants grown in optimal conditions were able to produce significantly more dry biomass then those stressed, however the differences in biomass and yield between WT and HM mpg1 plants were greater in stress plants. Growing conditions for greenhouse and growth chamber (TO-T4 & F2/BC1 populations). Non-optimal conditions containing a possible unknown stress Planting Media For both greenhouse and growth chamber environments the following media was to used: 1 part play sand, 4 parts Canadian sphagnum peat moss, 4 parts BX Promix Mycorise. The contents were mixed and transferred to pots. Pots were placed in a flat and watered until media was fully saturated.

Growing Conditions

Growing flats were filled with water, to the point of medium saturation throughout the entirety of the plant growth cycle. Plants were fertilized twice a week once they reached the 3-leaf stage of growth using Scotts Peters Excel 15-5-15 Cal-Mag granular fertilizer (0.75 tsp fertilizer per 1.9 L water). Plant chlorosis was monitored and treated at roughly 1 month post planting using iron chelator Sprint 330 at ⅛ tsp per 1 L of water. The growth chamber was set at 6:30 am 24° C., 80% RH, 3 fluorescent lights, 3 incandescent lights for 30 minutes, then shifting to 26° C., 80% RH, 6 fluorescent lights, 6 incandescent lights for 30 minutes, then shifting to 28° C., 80% RH, 8 fluorescent lights, 8 incandescent lights for 11 hours, then shifting to 28° C., 80% RH, 6 fluorescent lights, 6 incandescent lights for 30 minutes, then shifting to 26° C., 80% RH, 3 fluorescent lights, 3 incandescent lights for 30 minutes, and finally shifting to 24° C., 80% RH, 0 fluorescent lights, 0 incandescent lights for 11 hours. The growth parameters for the greenhouse were kept the same as the growth chamber, with the exception of naturally occurring photoperiods.

Experimental Populations

The T1 population consisted of five homozygous individuals for the MPG1 insertion, in a random block population containing an additional 85 individual plants from various other mutant lines. The plants were surrounded by a border of wild-type plants to account for edging light variability and spacing due to canopy growth effects within the population The T2 population consisted of two lines of the MPG1 insertion labeled (line 5 and line 6). The experiment contained 27 segregating individuals from line 5, and 22 segregating individuals from line 6. The experiment also contained 29 wild-type individuals. The population was set up in a random block format with an entire border of wild-type plants within the greenhouse. The T3 population contained 74 segregating individuals from line 6.21, 70 segregating individuals form line 5.56, 11 homozygous for the MPG1 insertion from line 5.6, 8 homozygous for the MPG1 insertion form line 6.44, and 15 individuals that are F1 backcrosses from line 5.44, all of which were in random block formation with a wild-type border within the greenhouse. T4&F2/BC1 Populations consisted of 34 individuals from F2/BC1 segregating line 5.44-1, 40 individuals from T4 homozygous line 5.44-7, 12 individuals from T3 F1 parent line 5.44, and 7 wild-type individuals. The population was set up in a random block format with an entire border of wild-type plants within the greenhouse. Growing conditions for greenhouse and growth chamber (T3-F2BC1 populations). Plants grown under optimal conditions.

Planting Media

For both greenhouse and growth chamber environments the following media was used: 1 part Profile Greens Grade, and 1 part BX Promix Mycorise. The contents were mixed to homogeneity, and transferred to pots. Pots were placed in a flat and watered until media was fully saturated.

Growing Conditions

Growing flats were filled with water, to the point of medium saturation throughout the entirety of the plant growth cycle. Plants were fertilized twice a week once they reached the 3-leaf stage of growth using granulized Technigro 15-5-15+ Cal-Mag at 37 g/5 ga. of hater. Plant chlorosis was monitored and treated at roughly 1 month post planting using iron chelator Sprint 330 at ⅛ tsp per 1 L of water. The growth chamber were set at 6:30 am 24° C., 80% RH, 3 fluorescent lights, 3 incandescent lights for 30 minutes, then shifting to 26° C., 80% RH, 6 fluorescent lights, 6 incandescent lights for 30 minutes, then shifting to 28° C., 80% RH, 8 fluorescent lights, 8 incandescent lights for 11 hours, then shifting to 28° C., 80% RH, 6 fluorescent lights, 6 incandescent lights for 30 minutes, then shifting to 26° C., 80% RH, 3 fluorescent lights, 3 incandescent lights for 30 minutes, and finally shifting to 24° C., 80% RH, 0 fluorescent lights, 0 incandescent lights for 11 hours. The growth parameters for the greenhouse were kept the same as the growth chamber, with the exception of naturally occurring photoperiods.

Experimental Populations

The T3 population consisted of 7 segregating individuals (line 5.56), 5 segregating individuals (line 6.13), 6 segregating individuals (line 6.21), and 6 segregating individuals to (line 6.41). The population was set up in a random block format with an within the growth chamber. The T3&F2/BC1 populations consisted of 34 T3 segregating individuals (line 5.44), 50 T3 segregating individuals (line 6.21), and 12 wild-type individuals. The population was set up in a random block format with an entire border of wild-type plants within the greenhouse.

Assessing the progeny of an mpg1 mutant crossed with a wild-type plant increases the confidence in the claim that constitutive overexpression of gene 0508g41030 is responsible for the pleiotropic phenotype visualized in the mpg1 mutant plant rather than another genetic event possibly present in the mpg1 mutant plants. The results consistently show the insertion co-seggregates 100% with the phenotype.

Backcrossing of MPG1

Rice panicles were assessed during the emerging stage of flowering. Green-seed spikelets from one individual were cut in half just prior to the milk stage, and de-masculinated by removing all interior pollen. Pollen was then taken from an alternate individual intended for crossing. Further developed spikelets from this plant with functional mature pollen that have sprung from spikelets were then taken and applied via shaking to the de-masculinated spikelets, and were bagged for the remainder of panicle development and seed filling stages. HM MPG1 (T2 line 5.44) mutant female (tissue)×true WT male (tissue) were used to perform the backcross.

Figure 45:
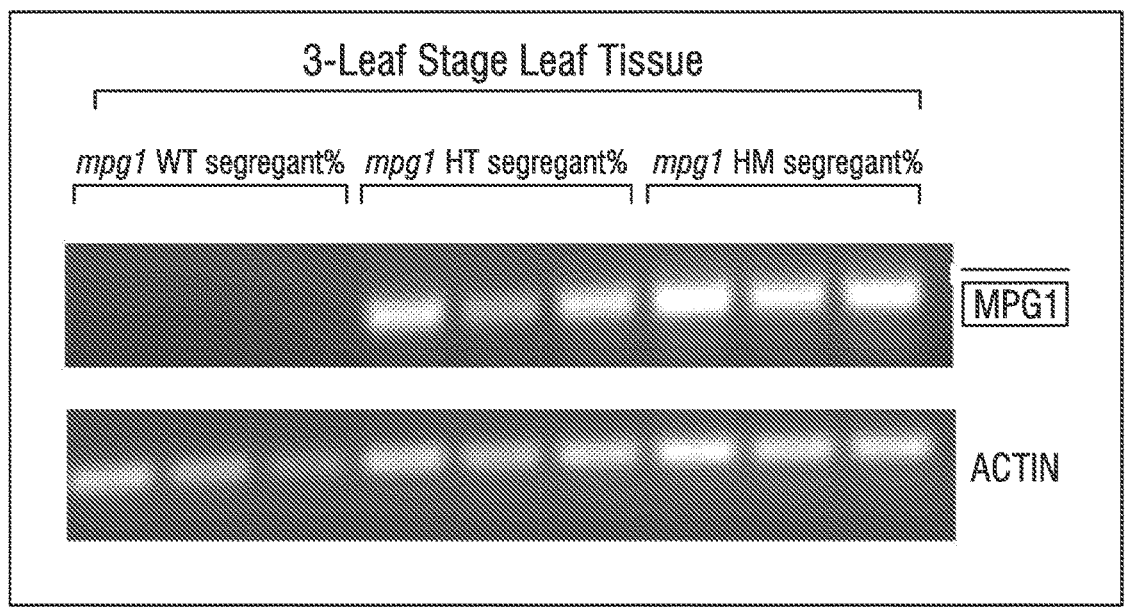
FIG. 45 demonstrates that mpg1 is a dominant trait in mpg 1.
Figure 46:
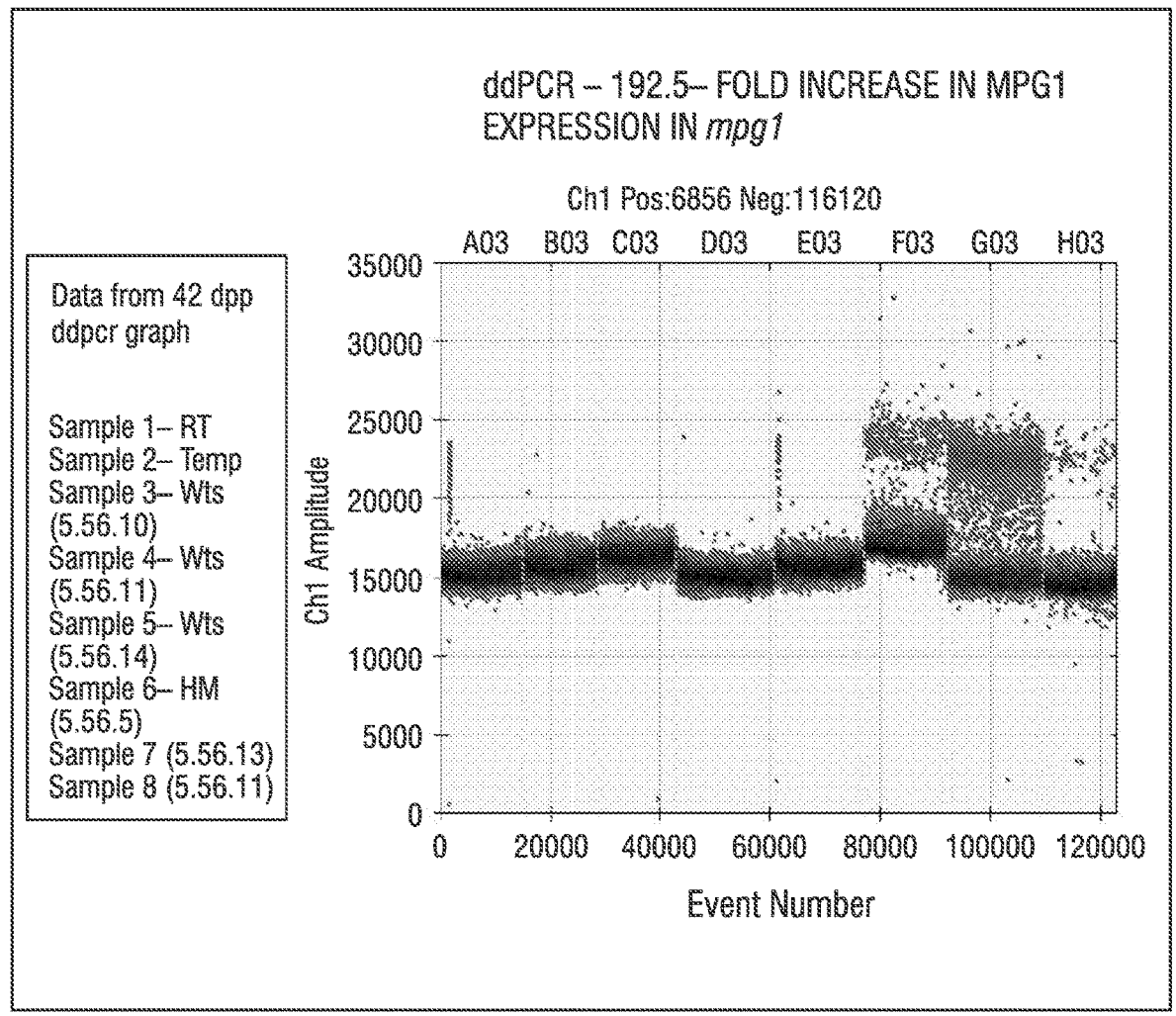
FIG. 46 is a ddPCR showing 192.5 fold increase in mpg1 expression in mpg1.
Figure 47:
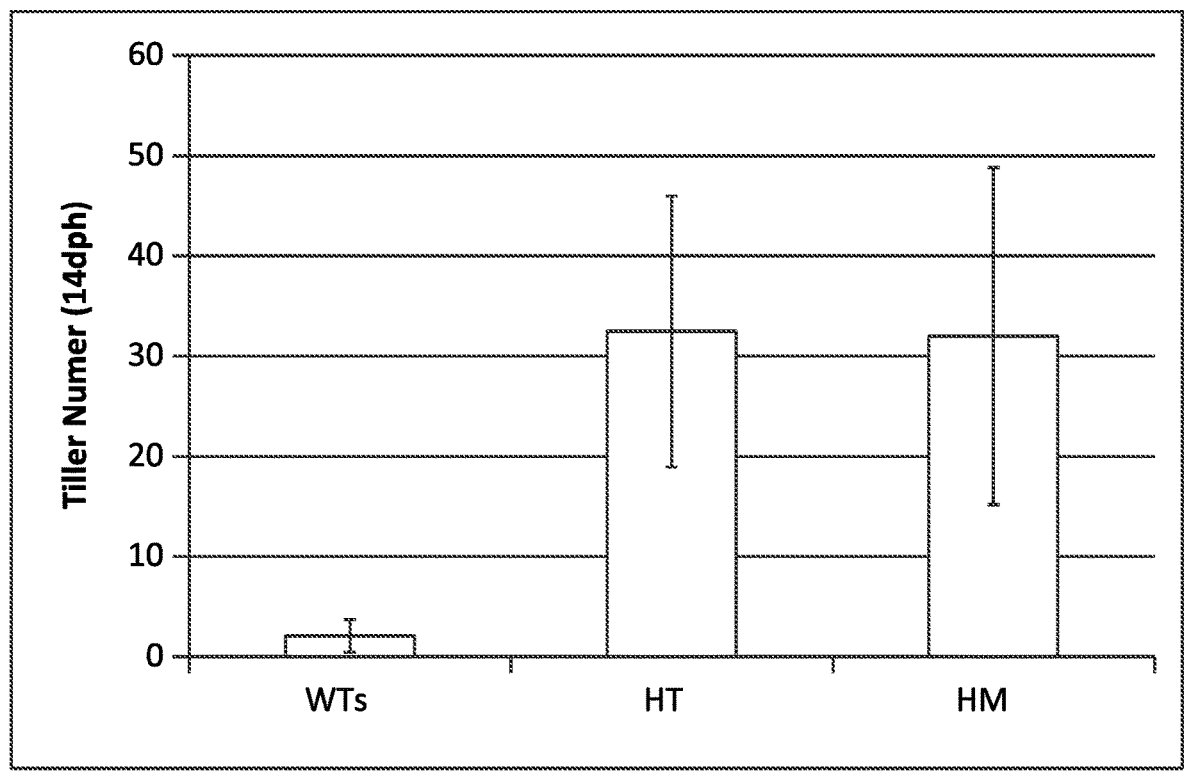
FIG. 47 is a graph of tiller accumulation at 41 days post harvesting (ratooning) of mpg1 plants compared to wildtype null segregants.

The gene OS08G41030 (MPG1) has been shown to be overexpressed in mpg1 plants across multiple generations and multiple tissue types. The gene also appears to be dominant. FIGS. 45-47 represent gene expression levels. 45 and 46 are RT-PCR gels that sow MPG1 overexpression in mpg1 plants where wildtype plants have no expression. FIG. 47 is a reading form DD PCR a highly quantifiable means of measuring gene expression. There one can see that the expression pattern continues (overexpression of Os08G41030 in mpg1 plants). When the gene is overexpressed the plants exhibit increased biomass accumulation, seed yield accumulation, and tolerance to stress compared to wild-type plants.

Example 3 Ratooning

Ratooning is the ability for a plant to regenerate new panicle-bearing tillers after a harvest (cutting of culms at the base of the plant). Ratooning is important for strategic crop management of rice procuction allwoing for fundamental increases in productivity. Benefits include shorter growth duration, multiple harvests per season, works well with late season tempeature and irrigation practices, and lower production csots (less labor intensive). Ratooned tiller develop form basal axillary bids. These remain within the stubbl of the harvested crop plant. (at crown).

MPG1 plants have increased ratooning ability. Data was accumulated on a population of mpg1 plants (population size 11 WT, 34 HT, 25 HM). The results showed that mpg1 plants had incdesased tiller accumulation post harvest, increased plant height, increased plant girth post harvest and incrased palnicles post harvest.

Figure 48:
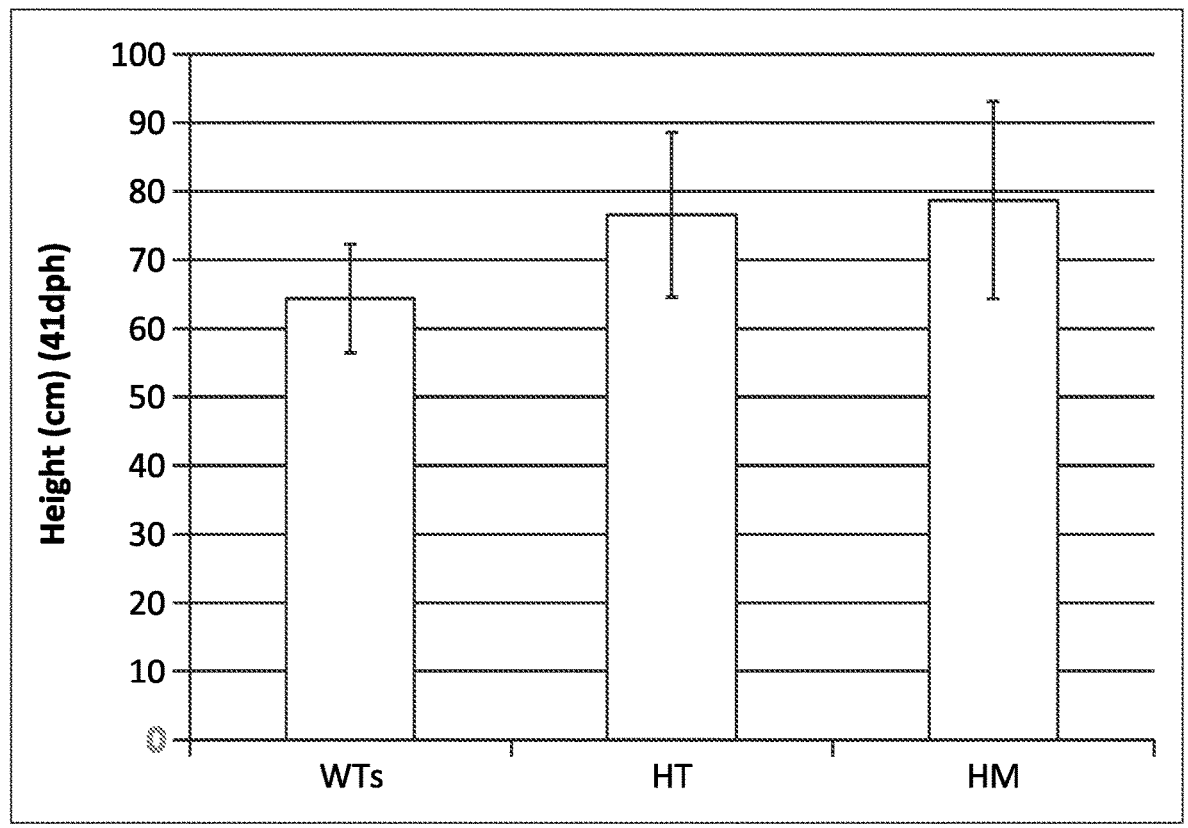
FIG. 48 is a graph of plant height at 41 days post harvesting (ratooning) of mpg1 plants compared to wildtype null segregants.
Figure 49:
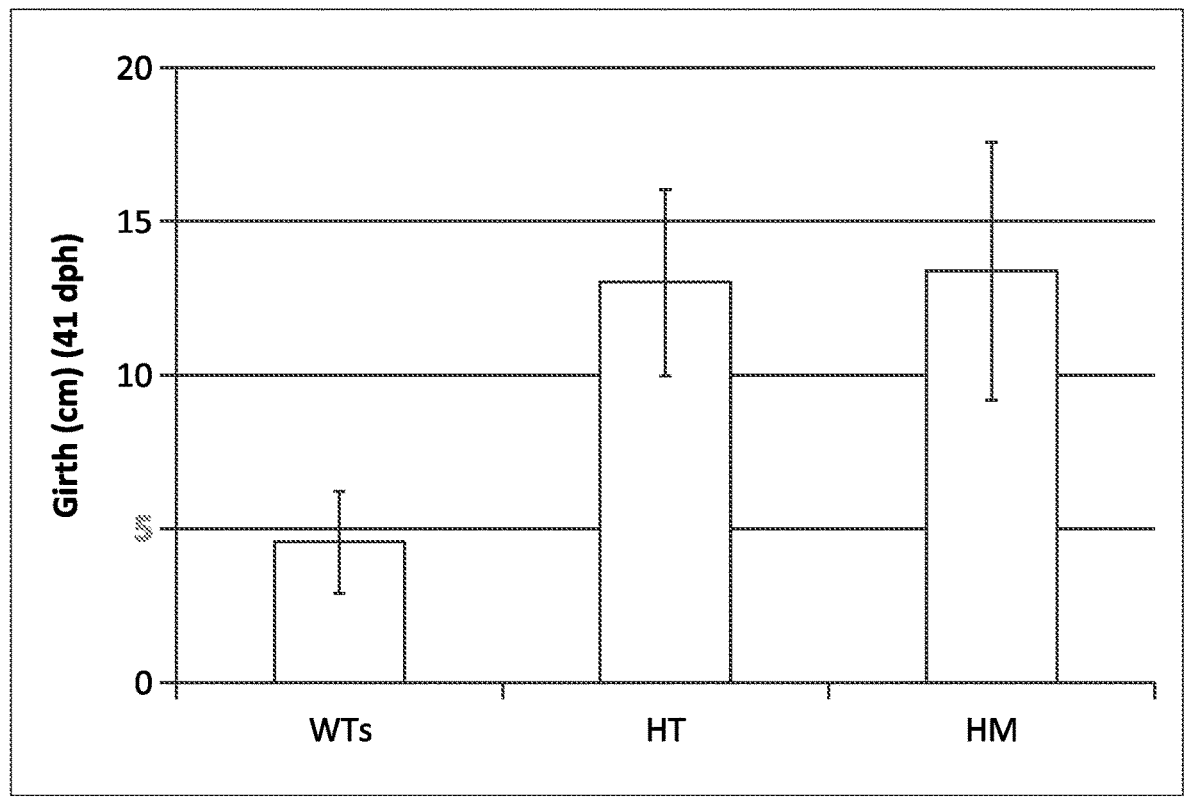
FIG. 49 is a graph showing plant girth at 41 days post harvesting (ratooning) of mpg1 plants compared to wildtype null segregants.
Figure 50:
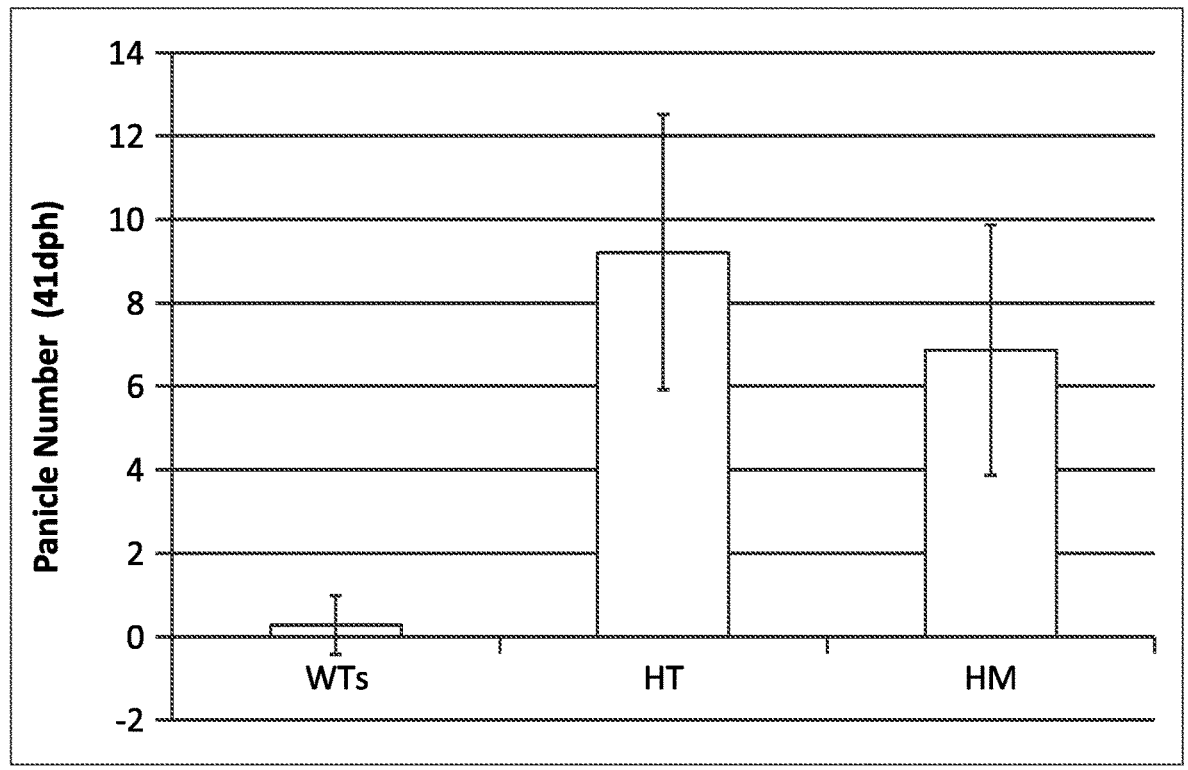
FIG. 50 is a graph of number of panicles at 41 days post harvesting (ratooning) of mpg1 plants compared to wildtype null segregants.

FIG. 47 shows that mpg1 plants have increased tiller accumulation at 41 days post harvesting (ratooning) compared to wild-type null segregants. FIG. 48 shows that mpg1 plants have increased height at 41 days post harvesting (ratooning) compared to wild-type null segregants. FIG. 49 shows that mpg1 plants have increased girth at 41 days post harvesting (ratooning) compared to wild-type null segregants. FIG. 50 shows that mpg1 plants have increased number of panicles at 41 days post harvesting (ratooning) compared to wild-type null segregants. (only 1/11) WTs Flowered at around 40 dph, all (59/59) mpg1 flowered at around 28 dph.

Example 4

MPG1 gene
LOC_Os08g41030 sequence information Genomic sequence length: 909 nucleotides
CDS length: 570 nucleotides
Protein length: 189 amino acids
Putative Function: AP2 domain containing protein, expressed

```
Genomic Sequence
>LOC_Os08g41030
                                                    SEQ ID NO: 3
ACCATCTCCTCCTCGTCATCGTCATCGTCTTCCTCCTCGCGTCGCCGATC

ACCTCGCCATGGTGCCGCCGGCGGCGCACGCGCCGAAGAACCTGGGGCTG

AGGGGGGTGCGGCGCCGGCTGTGGGGCAGGTGGGCGGCGGAGATCCGCGT

GCCGCGGGGCCACCGCGCGGCCGCGAGGCTGTGGATCGGCACGTTCCCGT

CCCCGGCGGCGGCGGCGCTCGCCTACGACGCCGCGCTCTACTGCTTCCAC

GGCGGCGCGCCGCCGGGGAACCGCGCCTTCAACTTCCCGCACGCGCCGCG

CCTCCGCATCGACGACCGCCGCCGCCACGCGCTCACGCCGGGCCACGTCA

GGGCCATCGCCGAGAGGTACGCCCACGACGTCGGCTCCGTCCTGTTCCGC

CCGCTCCCTCCGCCGCCGCCGCCCGTCGCCGCCGCCGCCGTCCCCGTGTT

CGCCGCACCTGCACCGCCCATGGCGCCGGCGCCGGCCAACCATGCTGCCG

ATCCTTACTACTGCAACGAGCCTGACACCACCACAGACGAGGACGTCATG

GCTGCGGCTGACCGCCTCCTCTCCATGGACATCGAAGAGGTCGCCGCTTT

GATCGCCATTGTTCAGCAAGGAGAGTGACCATATCTACAACTTCTTAGCT

AGCTAGTTACACCTTCTATGTAGCATGTGTACTATGCACTTTTGTGGTTG

TGTTGTGCTGTCCTAATGGTGTAACTAGCCATATCAAGGAAGACATGCAT

GATCTAGAGTCTAGAGTACTCTAGCCATGGAATAAATTAACTTAGTCTGT

ACTTGGTCATGCACCTTGTGTATGATCCTTGTGTAAGAGAAGTGTAATAA
```

```
                                    -continued
TCGGTTCTTGAAAAGGAACTGTTGTTATATATGAGATGGATGTTGTCATG

AAATGGAAA

CDS
>LOC_Os08g41030.1
                                                    SEQ ID NO: 1
ATGGTGCCGCCGGCGGCGCACGCGCCGAAGAACCTGGGGCTGAGGGGGT

GCGGCGCCGGCTGTGGGGCAGGTGGGCGGCGGAGATCCGCGTGCCGCGG

GCCACCGCGCGGCCGCGAGGCTGTGGATCGGCACGTTCCCGTCCCCGGCG

GCGGCGGCGCTCGCCTACGACGCCGCGCTCTACTGCTTCCACGGCGGCGC

GCCGCCGGGGAACCGCGCCTTCAACTTCCCGCACGCGCCGCGCCTCCGCA

TCGACGACCGCCGCCGCCACGCGCTCACGCCGGGCCACGTCAGGGCCATC

GCCGAGAGGTACGCCCACGACGTCGGCTCCGTCCTGTTCCGCCCGCTCCC

TCCGCCGCCGCCGCCCGTCGCCGCCGCCGCCGTCCCCGTGTTCGCCGCAC

CTGCACCGCCCATGGCGCCGGCGCCGGCCAACCATGCTGCCGATCCTTAC

TACTGCAACGAGCCTGACACCACCACAGACGAGGACGTCATGGCTGCGGC

TGACCGCCTCCTCTCCATGGACATCGAAGAGGTCGCCGCTTTGATCGCCA

TTGTTCAGCAAGGAGAGTGA

Protein
>LOC_Os08g41030.1
                                                    SEQ ID NO: 2
MVPPAAHAPKNLGLRGVRRRLWGRWAAEIRVPRGHRAAARLWIGTFPSPA

AAALAYDAALYCFHGGAPPGNRAFNFPHAPRLRIDDRRRHALTPGHVRAI

AERYAHDVGSVLFRPLPPPPPVAAAAVPVFAAPAPPMAPAPANHAADPY

YCNEPDTTTDEDVMAAADRLLSMDIEEVAALIAIVQQGE*
```

Example 5

The following is a list of publications showing several AP family genes from monocots also work in dicot plants. Thus it is expected that the over expression phenotype of mpg1 will work in all higher plants.

Literature—Examples of a Monocot AP2 Showing Function in a Dicot

Examples Specific to Rice AP2's in Dicots

1) Julian M P, et al, Expression of rice SUB1A and SUB1C transcription factors in *Arabidopsis* uncovers flowering inhibition as a submergence tolerance mechanism. The Plant Journal. (2011); 67(3):434-446
2) Yifei C, et al, Overexpression of the rice EREBP-like gene OsBIERF3 enhances disease resistance and salt tolerance in transgenic tobacco. Physiological and Molecular Plant Pathology. (2005-2006) 67(3-5):202-211
3) Xiaofeng J, et al, Transcription factor OsAP21 gene increases salt/drought tolerance in transgenic *Arabidopsis thaliana*. Molecular Biology Reports. (2013) 40(2):1743
4) Yibing H., et al., Overexpression of OsERF1, a novel rice ERF gene, up-regulates ethylene-responsive genes expression besides affects growth and development in *Arabidopsis*. *Journal of Plant Physiology* (2008) 165(16): 1717-1725
5) Zhang Y., et al., Expression of a rice DREB1 gene, OsDREB1D, enhances cold and high-salt tolerance in transgenic *Arabidopsis*. BMB Reports. (2009) 42(8):486-492
6) Gutha L R, Reddy A R. Rice DREB1B promoter shows distinct stress-specific responses, and the overexpression of cDNA in tobacco confers improved abiotic and biotic stress tolerance. Plant Molecular Biology. (2008) 68:533. doi:10.1007/s11103-008-9391-8
7) Wang Q., et al., Overexpression of a rice OsDREB1F gene increases salt, drought, and low temperature tolerance in both *Arabidopsis* and rice. Plant Molecular Biology. (2008) 67(6):589-602

Examples Specific of Non-Rice Monocot AP2 in Dicot

1) RuHao S, et al., Characterization and ectopic expression of CoWRI1, AP2/EREBP domain-containing transcription factor from coconut (*Cocos nucifera* L.) endosperm, changes the seeds oil content in transgenic *Arabidopsis thaliana* and rice (*Oryza sativa* L.) Frontiers in Plant Science. (2017) 8:63. doi: 10.3389/fpls.2017.00063
2) Qin F, et al, Cloning and functional analysis of a novel DREB1/CBF transcription factor involved in cold-responsive gene expression in *Zea mays* L. Plant Cell Physiol. (2004). 45(8):1042-1052
3) HongXia L, et al., A novel activator-type ERF of *Thinopyrum intermedium*, TiERF1, positively regulates defense responses. *Journal of Experimental Botany*. (2008) 59(11):3111-3120
4) Trujillo L E, et al., SodERF3, a novel sugarcane ethylene responsive factor (ERF), enhances salt and drought tolerance when overexpressed in tobacco plants. *Plant* Cell Physiol. (2008) 49(4):512-525

Example 6

The following is a list of wheat genes that align with mpg1 suggesting the over-expression of these will yield the same phenotype in wheat. Applicants are confident, based upon precedence that over-expression in wheat will replicate the phenotype.

BLASTP 2.2.29+

"Reference: Stephen F. Altschul, Thomas L. Madden, Alejandro A." "Schaffer, Jinghui Zhang, Zheng Zhang, Webb Miller, and David J." "Lipman (1997)," "Gapped BLAST and PSI-BLAST: a new generation of "protein database search programs", *Nucleic Acids Res.* 25:3389-3402." "Reference for composition-based statistics: Alejandro A. Schaffer,"

"L. Aravind, Thomas L. Madden, Sergei Shavirin, John L. Spouge, Yuri" "I. Wolf, Eugene V. Koonin, and Stephen F. Altschul (2001)," "Improving the accuracy of PSI-BLAST protein database searches with composition-based statistics and other refinements, Nucleic Acids" Res. 29:2994-3005.

Database: *Triticum_aestivum*.TGACv1.pep.all

"154,140 sequences; 70,022,883 total letters"

Query=EMBOSS_001

Length=189

Score E

| Sequences producing significant alignments: | (Bits) | Value |
| --- | --- | --- |
| lcl\|EG:TRIAE_CS42_7BS_TGACv1_591920_AA1925640.1 pep scaffold:TGA . . . | 45.3 | 2e−04 |
| lcl\|EG:TRIAE_CS42_7AS_TGACv1_570405_AA1835200.1 pep scaffold:TGA . . . | 44.4 | 4e−04 |

-continued

| Sequences producing significant alignments: | (Bits) | Value |
|---|---|---|
| lcl\|EG:TRIAE_CS42_7AS_TGACv1_569305_AA1813080.1 pep scaffold:TGA . . . | 43.9 | 5e-04 |
| lcl\|EG:TRIAE_CS42_7DS_TGACv1_621657_AA2022340.1 pep scaffold:TGA . . . | 43.4 | 7e-04 |
| lcl\|EG:TRIAE_CS42_7DS_TGACv1_621657_AA2022350.1 pep scaffold:TGA . . . | 42.5 | 0.001 |
| lcl\|EG:TRIAE_CS42_7AS_TGACv1_570405_AA1835190.1 pep scaffold:TGA . . . | 39.2 | 0.014 |
| lcl\|EG:TRIAE_CS42_7BS_TGACv1_591920_AA1925630.1 pep scaffold:TGA . . . | 38.3 | 0.026 |
| lcl\|EG:TRIAE_CS42_5AL_TGACv1_375472_AA1222340.1 pep scaffold:TGA . . . | 36.4 | 0.095 |
| lcl\|EG:TRIAE_CS42_5DL_TGACv1_433263_AA1407500.1 pep scaffold:TGA . . . | 36.4 | 0.095 |

Example 7

The following is a list of 250 genes from both monocot and dicot plants with various levels of protein sequence similarity that suggests over-expression of these will likely yield the same phenotype as mpg1.

BLASTP 2.6.1+

"Reference: Stephen F. Altschul, Thomas L. Madden, Alejandro" "A. Schaffer, Jinghui Zhang, Zheng Zhang, Webb Miller, and" "David J. Lipman (1997)," "Gapped BLAST and PSI-BLAST: a new" "generation of protein database search programs", Nucleic" Acids Res. 25:3389-3402.

Reference for compositional score matrix adjustment: Stephen "F. Altschul, John C. Wootton, E. Michael Gertz, Richa" "Agarwala, Aleksandr Morgulis, Alejandro A. Schaffer, and" "Yi-Kuo Yu (2005)" "Protein database searches using ""compositionally adjusted substitution matrices"", *FEBS J."* 272:5101-5109.

RID: MSGS16R1014

Database: All non-redundant GenBank CDS translations+PDB+SwissProt+PIR+PRF excluding environmental samples from WGS projects "125,068,878 sequences; 45,873,948,431 total letters"

Query=mpg1 protein sequence

Length=189

Score E

| Sequences producing significant alignments: | (Bits) | Value |
|---|---|---|
| XP_015649451.1 PREDICTED: ethylene-responsive transcription f . . . | 370 | 1e–129 |
| EAZ43372.1 hypothetical protein OsJ_27975 [*Oryza sativa* Japon . . . | 186 | 1e–56 |
| XP_006660297.1 PREDICTED: ethylene-responsive transcription f . . . | 143 | 4e–40 |
| XP_020154174.1 ethylene-responsive transcription factor ERF01 . . . | 126 | 4e–33 |
| XP_020154175.1 ethylene-responsive transcription factor ERF01 . . . | 125 | 6e–33 |
| KQJ98978.1 hypothetical protein BRADI_3g40343 [*Brachypodium* d . . . | 104 | 1e–24 |
| XP_008666483.1 ethylene-responsive transcription factor ERF01 . . . | 103 | 2e–24 |
| XP_010236752.1 PREDICTED: ethylene-responsive transcription f . . . | 99.4 | 1e–23 |
| XP_002444750.1 ethylene-responsive transcription factor ERF01 . . . | 101 | 3e–23 |
| AIB05005.1 AP2-EREBP transcription factor [*Zea mays*] | 101 | 3e–23 |
| XP_008666485.1 ethylene-responsive transcription factor ERF01 . . . | 101 | 4e–23 |
| XP_002444752.1 ethylene-responsive transcription factor ERF01 . . . | 96.3 | 3e–21 |
| OQU80890.1 hypothetical protein SORBI_3007G205400 [*Sorghum bi* . . . | 91.3 | 5e–20 |
| KQL02490.1 hypothetical protein SETIT_015435mg [*Setaria italica*] | 91.7 | 5e–20 |
| XP_002444753.1 ethylene-responsive transcription factor ERF01 . . . | 91.3 | 5e–20 |
| XP_004974846.1 PREDICTED: ethylene-responsive transcription f . . . | 91.7 | 8e–20 |
| XP_004974850.1 PREDICTED: ethylene-responsive transcription f . . . | 92.4 | 1e–19 |
| OEL30104.1 hypothetical protein BAE44_0008879 [*Dichanthelium* . . . | 92.8 | 1e–19 |
| KQL02491.1 hypothetical protein SETIT_014944mg [*Setaria italica*] | 88.2 | 4e–19 |
| XP_004974847.1 PREDICTED: ethylene-responsive transcription f . . . | 89.0 | 5e–19 |
| XP_008666482.1 ethylene-responsive transcription factor ERF01 . . . | 89.4 | 7e–19 |
| XP_018466374.1 PREDICTED: ethylene-responsive transcription f . . . | 86.3 | 9e–18 |
| XP_006284912.1 hypothetical protein CARUB_v10006208mg [Capsel . . . | 85.1 | 3e–17 |
| XP_013678940.1 PREDICTED: ethylene-responsive transcription f . . . | 84.7 | 3e–17 |
| XP_013678836.1 PREDICTED: ethylene-responsive transcription f . . . | 84.3 | 7e–17 |
| XP_018449536.1 PREDICTED: ethylene-responsive transcription f . . . | 83.6 | 9e–17 |
| AAT44951.1 putative AP2/EREBP transcription factor [*Arabidops* . . . | 83.2 | 1e–16 |
| NP_567867.1 Integrase-type DNA-binding superfamily protein [A . . . | 82.8 | 2e–16 |
| XP_012077166.1 ethylene-responsive transcription factor ERF01 . . . | 82.4 | 5e–16 |
| XP_006345254.1 PREDICTED: ethylene-responsive transcription f . . . | 82.8 | 6e–16 |
| XP_015060745.1 PREDICTED: ethylene-responsive transcription f . . . | 82.4 | 6e–16 |
| CDY28240.1 BnaA01g06090D [*Brassica napus*] | 84.7 | 7e–16 |
| XP_008801457.1 PREDICTED: ethylene-responsive transcription f . . . | 81.3 | 9e–16 |
| XP_002444751.1 ethylene-responsive transcription factor ERF01 . . . | 80.5 | 1e–15 |
| CAA18187.1 putative protein [*Arabidopsis thaliana*] | 82.0 | 1e–15 |
| XP_013669838.1 PREDICTED: ethylene-responsive transcription f . . . | 80.5 | 1e–15 |
| XP_009127267.1 PREDICTED: ethylene-responsive transcription f . . . | 80.5 | 1e–15 |
| XP_010436316.1 PREDICTED: ethylene-responsive transcription f . . . | 80.5 | 1e–15 |
| XP_013585531.1 PREDICTED: ethylene-responsive transcription f . . . | 80.5 | 1e–15 |
| XP_004251702.1 PREDICTED: ethylene-responsive transcription f . . . | 81.6 | 2e–15 |
| XP_002869347.1 ethylene-responsive transcription factor ERF01 . . . | 80.1 | 2e–15 |
| OAO6568.1 hypothetical protein AXX17_AT4G35600 [*Arabidopsis* . . . | 80.9 | 2e–15 |
| XP_010451100.1 PREDICTED: ethylene-responsive transcription f . . . | 79.7 | 3e–15 |
| XP_010445038.1 PREDICTED: ethylene-responsive transcription f . . . | 79.3 | 3e–15 |
| XP_009108952.1 PREDICTED: ethylene-responsive transcription f . . . | 79.3 | 3e–15 |
| XP_010496785.1 PREDICTED: ethylene-responsive transcription f . . . | 80.1 | 4e–15 |
| APQ47403.1 AP2/ERF domain-containing transcription factor [Ve . . . | 79.0 | 4e–15 |
| XP_016540315.1 PREDICTED: uncharacterized protein LOC10784088 . . . | 81.6 | 6e–15 |

| Sequences producing significant alignments: | (Bits) | Value |
|---|---|---|
| XP_013628133.1 PREDICTED: ethylene-responsive transcription f . . . | 78.2 | 8e-15 |
| OAY69209.1 Ethylene-responsive transcription factor ERF018 [A . . . | 78.2 | 1e-14 |
| XP_020083384.1 ethylene-responsive transcription factor ERF01 . . . | 77.4 | 1e-14 |
| CDY23275.1 BnaA08g12710D [*Brassica napus*] | 79.0 | 1e-14 |
| OAY23940.1 hypothetical protein MANES_18G119500 [*Manihot escu* . . . | 77.4 | 1e-14 |
| CDX68719.1 BnaC01g07340D [*Brassica napus*] | 80.9 | 2e-14 |
| XP_018455497.1 PREDICTED: ethylene-responsive transcription f . . . | 76.6 | 2e-14 |
| OVA19328.1 AP2/ERF domain [*Macleaya cordata*] | 77.4 | 2e-14 |
| XP_013649493.1 PREDICTED: ethylene-responsive transcription f . . . | 76.3 | 2e-14 |
| XP_019193989.1 PREDICTED: ethylene-responsive transcription f . . . | 78.2 | 2e-14 |
| KZV57112.1 hypothetical protein F511_05986 [*Dorcoceras hygrom* . . . | 76.3 | 2e-14 |
| XP_015884426.1 PREDICTED: ethylene-responsive transcription f . . . | 77.8 | 2e-14 |
| XP_013676405.1 PREDICTED: ethylene-responsive transcription f . . . | 75.9 | 3e-14 |
| XP_015945523.1 ethylene-responsive transcription factor ERF01 . . . | 78.2 | 3e-14 |
| XP_009127864.1 PREDICTED: ethylene-responsive transcription f . . . | 75.9 | 3e-14 |
| XP_002308508.1 hypothetical protein POPTR_0006s23480g [*Populu* . . . | 77.4 | 3e-14 |
| XP_011019312.1 PREDICTED: ethylene-responsive transcription f . . . | 77.0 | 4e-14 |
| XP_010420984.1 PREDICTED: ethylene-responsive transcription f . . . | 77.4 | 4e-14 |
| OAP14363.1 hypothetical protein AXX17_AT1G65720 [*Arabidopsis* . . . | 75.5 | 4e-14 |
| XP_011093871.1 ethylene-responsive transcription factor ERF01 . . . | 77.4 | 5e-14 |
| NP_177307.1 Integrase-type DNA-binding superfamily protein [A . . . | 75.1 | 5e-14 |
| XP_003610945.1 AP2 domain class transcription factor [*Medicag* . . . | 75.9 | 5e-14 |
| XP_010471164.1 PREDICTED: ethylene-responsive transcription f . . . | 75.5 | 5e-14 |
| KYP42896.1 Ethylene-responsive transcription factor ERF017 fa . . . | 76.3 | 5e-14 |
| XP_017625830.1 PREDICTED: ethylene-responsive transcription f . . . | 75.1 | 6e-14 |
| OMO91831.1 hypothetical protein COLO4_18058 [*Corchorus olitor* . . . | 76.6 | 6e-14 |
| XP_013591784.1 PREDICTED: ethylene-responsive transcription f . . . | 75.1 | 6e-14 |
| XP_006474529.1 PREDICTED: ethylene-responsive transcription f . . . | 77.0 | 6e-14 |
| XP_006301935.1 hypothetical protein CARUB_v10022408mg [Capsel . . . | 75.1 | 6e-14 |
| XP_010427986.1 PREDICTED: ethylene-responsive transcription f . . . | 75.1 | 8e-14 |
| XP_006412635.1 hypothetical protein EUTSA_v10026328mg [Eutrem . . . | 75.5 | 9e-14 |
| XP_003527767.1 PREDICTED: ethylene-responsive transcription f . . . | 77.4 | 1e-13 |
| XP_004287662.1 PREDICTED: ethylene-responsive transcription f . . . | 75.9 | 1e-13 |
| XP_020239081.1 ethylene-responsive transcription factor ERF01 . . . | 76.3 | 1e-13 |
| XP_013465862.1 ethylene-responsive transcription factor ERF01 . . . | 75.9 | 1e-13 |
| XP_002893033.1 ethylene-responsive transcription factor ERF01 . . . | 75.1 | 1e-13 |
| EOY30203.1 AP2/ERF domain-containing transcription factor [Th . . . | 75.5 | 1e-13 |
| XP_006452945.1 hypothetical protein CICLE_v10010348mg [*Citrus* . . . | 75.9 | 1e-13 |
| XP_009105818.1 PREDICTED: ethylene-responsive transcription f . . . | 73.9 | 2e-13 |
| XP_013465860.1 ethylene-responsive transcription factor ERF01 . . . | 75.9 | 2e-13 |
| XP_006288608.1 hypothetical protein CARUB_v10001903mg [Capsel . . . | 75.5 | 2e-13 |
| XP_002887377.1 ethylene-responsive transcription factor ERF02 . . . | 73.9 | 2e-13 |
| XP_006390762.1 hypothetical protein EUTSA_v10019510mg [Eutrem . . . | 73.9 | 2e-13 |
| XP_021276867.1 LOW QUALITY PROTEIN: ethylene-responsive trans . . . | 75.5 | 2e-13 |
| XP_002280370.1 PREDICTED: ethylene-responsive transcription f . . . | 74.7 | 2e-13 |
| XP_016720463.1 PREDICTED: ethylene-responsive transcription f . . . | 75.1 | 2e-13 |
| "EOY30093.1 Integrase-type DNA-binding superfamily protein, pu . . . | 75.5 | 2e-13" |
| XP_004488105.1 PREDICTED: ethylene-responsive transcription f . . . | 74.7 | 2e-13 |
| XP_013465861.1 ethylene-responsive transcription factor ERF01 . . . | 75.9 | 3e-13 |
| GAU17659.1 hypothetical protein TSUD_07200 [*Trifolium subterr* . . . | 75.5 | 3e-13 |
| CDY03696.1 BnaA02g15410D [*Brassica napus*] | 73.6 | 3e-13 |
| XP_007012474.2 PREDICTED: ethylene-responsive transcription f . . . | 75.1 | 3e-13 |

All publications and patent applications in this specification are indicative of the level of ordinary skill in the art to which this invention pertains. All publications and patent applications are herein incorporated by reference to the same extent as if each individual publication or patent application was specifically and individually indicated by reference.

The invention has been described with reference to various specific and preferred embodiments and techniques. However, it should be understood that many variations and modifications may be made while remaining within the spirit and scope of the invention as described in the appended claims.

What is claimed is:

1. A method of increasing biomass or seed yield in a plant comprising:
    introducing in said plant a polynucleotide encoding a MPG1 transcription factor polypeptide, wherein said MPG1 transcription factor polypeptide has MPG1 transcription factor protein activity and is a polypeptide comprising an amino acid sequence having at least 90% sequence identity to the sequence set forth in SEQ ID NO:2; and
selecting for a plant with increased biomass or seed yield under non-stress conditions relative to a control plant without the polynucleotide encoding the MPG1 transcription factor polypeptide.

2. The method of claim 1, wherein said polypeptide comprises an amino acid sequence having at least 95% sequence identity with the sequence set forth in SEQ ID NO: 2.

3. The method of claim 1, wherein said polypeptide comprises the amino acid sequence set forth in SEQ ID NO: 2.

4. The method of claim 1, comprising introducing into said plant an expression cassette comprising the polynucleotide encoding the MPG1 transcription factor polypeptide operably linked to a promoter that drives expression in a plant cell, wherein said polynucleotide comprises:
    (a) the nucleotide sequence set forth in SEQ ID NO: 1 or 3;
    (b) a nucleotide sequence encoding the polypeptide of SEQ ID NO: 2;
    (c) a nucleotide sequence comprising at least 95% sequence identity to the sequence set forth in SEQ ID NO: 1 or 3; or
    (d) a nucleotide sequence encoding a polypeptide comprising the amino acid sequence set forth in SEQ ID NO: 2.

5. The method of claim 4, comprising: (a) transforming a plant cell with said expression cassette; and (b) regenerating a transformed plant from the transformed plant cell of step (a).

6. The method of claim 4, wherein said expression cassette is stably incorporated into the genome of the plant.

7. The method of claim 4, wherein said promoter is a constitutive, tissue specific, or developmentally regulated promoter.

8. The method of claim 1, wherein the polynucleotide encoding the MPG1 transcription factor polypeptide comprises the nucleotide sequence set forth in SEQ ID NO: 1 or 3; or a nucleotide sequence having at least 95% sequence identity to the sequence set forth in SEQ ID NO: 1 or 3.

9. A method of producing a plant with increased biomass or seed yield, the method comprising:
    introducing in a plant cell a polynucleotide encoding a MPG1 transcription factor, wherein the MPG1 transcription factor comprises an amino acid sequence having at least 90% sequence identity to the sequence set forth in SEQ ID NO:2;
    regenerating a plant from the plant cell; and
    selecting for a plant with increased biomass or seed yield under non-stress conditions relative to a control plant without the polynucleotide encoding the MPG1 transcription factor polypeptide.

* * * * *